United States Patent
Lindsay et al.

(10) Patent No.: US 10,444,220 B2
(45) Date of Patent: **\*Oct. 15, 2019**

(54) CONTROLLED TUNNEL GAP DEVICE FOR SEQUENCING POLYMERS

(71) Applicant: Arizona Board of Regents on behalf of Arizona State University, Scottsdale, AZ (US)

(72) Inventors: Stuart Lindsay, Phoenix, AZ (US); Shuai Chang, Tempe, AZ (US); Jin He, Mesa, AZ (US); Peiming Zhang, Gilbert, AZ (US); Shuo Huang, Tempe, AZ (US)

(73) Assignee: Arizona Board of Regents on behalf of Arizona State University, Scottsdale, AZ (US)

(\*) Notice: Subject to any disclaimer, the term of this patent is extended or adjusted under 35 U.S.C. 154(b) by 169 days.

This patent is subject to a terminal disclaimer.

(21) Appl. No.: 15/712,552

(22) Filed: Sep. 22, 2017

(65) Prior Publication Data

US 2018/0224422 A1 Aug. 9, 2018

Related U.S. Application Data

(63) Continuation of application No. 14/851,933, filed on Sep. 11, 2015, now Pat. No. 9,810,681, which is a (Continued)

(51) Int. Cl.
- *G01N 33/487* (2006.01)
- *C12Q 1/6869* (2018.01)
- *G01N 27/327* (2006.01)

(52) U.S. Cl.
CPC ..... *G01N 33/48721* (2013.01); *C12Q 1/6869* (2013.01); *G01N 27/3275* (2013.01); *Y10T 436/143333* (2015.01)

(58) Field of Classification Search
None
See application file for complete search history.

(56) References Cited

U.S. PATENT DOCUMENTS

| 6,905,586 B2 | 6/2005 | Lee et al. |
| 8,628,649 B2 | 1/2014 | Lindsay et al. |
| (Continued) | | |

FOREIGN PATENT DOCUMENTS

| JP | 2002-522748 A | 7/2002 |
| JP | 2008-536124 A | 9/2008 |
| (Continued) | | |

OTHER PUBLICATIONS

Akeson et al. "Microsecond Time-Scale Discrimination Among Polycytidylic Acid, Polyadenylic Acid, and Polyuridylic Acid as Homopolymers or as Segments Within Single RNA Molecules." Biophys. J. 77.6(1999):3227-3233.

(Continued)

*Primary Examiner* — Xiaoyun R Xu
(74) *Attorney, Agent, or Firm* — Schwabe Williamson & Wyatt, P.C.

(57) ABSTRACT

The invention includes compositions, devices, and methods for analyzing a polymer and/or polymer unit. The polymer may be a homo or hetero-polymer such as DNA, RNA, a polysaccharide, or a peptide. The device includes electrodes that form a tunnel gap through which the polymer can pass. The electrodes are functionalized with a reagent attached thereto, and the reagent is capable of forming a transient bond to a polymer unit. When the transient bond forms between the reagent and the unit, a detectable signal is generated and used to analyze the polymer.

14 Claims, 82 Drawing Sheets

Related U.S. Application Data continuation of application No. 13/395,956, filed as application No. PCT/US2011/023185 on Jan. 31, 2011, now Pat. No. 9,140,682.

(60) Provisional application No. 61/300,678, filed on Feb. 2, 2010, provisional application No. 61/378,838, filed on Aug. 31, 2010.

(56) References Cited

U.S. PATENT DOCUMENTS

| | | | |
|---|---|---|---|
| 8,961,757 | B2 | 2/2015 | Nuckolls et al. |
| 8,968,540 | B2 | 3/2015 | Reinhart et al. |
| 9,140,682 | B2 | 9/2015 | Lindsay et al. |
| 9,274,430 | B2 | 3/2016 | Gyarfas et al. |
| 9,395,352 | B2 | 7/2016 | Lindsay et al. |
| 9,766,248 | B2 | 9/2017 | Lindsay et al. |
| 9,810,681 | B2 | 11/2017 | Lindsay et al. |
| 2002/0033345 | A1 | 3/2002 | Meade |
| 2005/0202444 | A1 | 9/2005 | Zhu |
| 2006/0194228 | A1 | 8/2006 | Rakitin et al. |
| 2006/0211016 | A1 | 9/2006 | Kayyem et al. |
| 2009/0198117 | A1 | 8/2009 | Cooper et al. |
| 2013/0186757 | A1 | 7/2013 | Reinhart et al. |
| 2015/0010935 | A1 | 1/2015 | Lindsay et al. |
| 2015/0142327 | A1 | 5/2015 | Ashcroft et al. |
| 2015/0144506 | A1 | 5/2015 | Lindsay et al. |
| 2016/0018384 | A1 | 1/2016 | Lindsay et al. |
| 2016/0177383 | A1 | 6/2016 | Ashcroft et al. |
| 2016/0194698 | A1 | 7/2016 | Lindsay |
| 2016/0258925 | A1 | 9/2016 | Gyarfas et al. |
| 2016/0280723 | A1 | 9/2016 | Zhang et al. |
| 2017/0003245 | A1 | 1/2017 | Lindsay et al. |
| 2017/0016852 | A1 | 1/2017 | Lindsay et al. |
| 2017/0038369 | A1 | 2/2017 | Lindsay et al. |
| 2017/0067902 | A1 | 3/2017 | Zhang et al. |
| 2017/0137389 | A1 | 5/2017 | Zhang et al. |
| 2017/0204066 | A1 | 7/2017 | Lindsay et al. |
| 2017/0343558 | A1 | 11/2017 | Lindsay et al. |

FOREIGN PATENT DOCUMENTS

| | | |
|---|---|---|
| WO | WO 99/57550 A1 | 11/1999 |
| WO | WO 2007/084163 A2 | 7/2007 |
| WO | WO 2008/071982 A2 | 6/2008 |
| WO | WO 2008124706 A2 | 10/2008 |

OTHER PUBLICATIONS

Aksimentiev et al. "Microscopic Kinetics of DNA Translocation through Synthetic Nanopores." Biophys. J. 87.3(2004):2086-2097.
Ashcroft et al. "An AFM/Rotaxane Molecular Reading Head for Sequence-Dependent DNA Structure" Small 4, 1468-1475 (2008).
Ashkenasy et al. "Recognizing a Single Base in an Individual DNA Strand: A Step Toward DNA Sequencing in Nanopores." Angew. Chem. Int. Ed. Engl. 44.9(2005):1401-1404.
Barawkar et al. "Effect of C5-Amino Substituent on 2'-Deoxyuridine Base Pairing with 2'-Deoxyadenosine: Investigation by 1H and 13C NMR Spectroscopy." Tetrahedron. 48.39(1992):8505-8514.
Branton et al. "The Potential and Challenges of Nanopore Sequencing." Nat. Biotechnol. 26.10(2008):1146-1153.
Chang et al., "Tunnel Conductance of Watson-Crick Nucleoside-Base Pairs from Telegraph Noise," Nanotechnol. 20(18):185102 (2009).
Chang et al. "Electronic Signatures of all Four DNA Nucleosides in a Tunneling Gap." Nano Lett. 10.3(2010):1070-1075.
Chang et al. "Tunneling Readout of Hydrogen-Bonding-Based Recognition" Nat. Nanotechnol. 4.5(2009):297-301.
Chowdhury, S. et al., "Novel oxorhenium(V) '3+1' mixed ligand complexes with 3-thiapentane-1,5-dithiolate and functional mercaptobenzoyl amino acid ethyl ester," Inorganica Chimica Acata 361 (2008): 145-152.

Clarke et al. Continuous base identification for single-molecule nanopore DNA sequencing. Nature Nanotechnology 4, 265-270 (2009).
Creager et al. "Conformational Rigidity in a Self-Assembled Monolayer of 4-Mercaptobenzoic Acid on Gold." Langmuir. 11.6(1995):1852-1854.
Cui et al. "Reproducible Measurement of Single-Molecule Conductivity." Science. 294.5542(2001):571-574.
Derose et al. "Gold Grown Epitaxially on Mica: Conditions for Large Area Flat Faces." Surface Sci. 256.1-2(1991):102-108.
Feldman et al. "Molecular Electronic Devices Based on Single-Walled Carbon Nanotube Electrodes." Acc. Chem. Res. 41.12(2008):1731-1741.
Fuhrmann et al. "Refined procedure of evaluating experimental single-molecule force spectroscopy data" Phys Rev. E 77, 03912-03922 (2008).
Fuhrmann, "Force Spectroscopy, from Single Molecules to Whole Cells: Refined Procedures of Data Analysis." Dissertation, Arizona State University. Proquest/UMI 3410536. May 2010.
Getfert et al. "Optimal evaluation of single-molecule force spectroscopy experiments" Phys Rev E 76, 052901-052905 (2007).
Goldsmith et al. "Monitoring single-molecule reactivity on a carbon nanotube" Nano Letters 8(1), 189-194 (2008).
Gross, L. et al. "The Chemical Structure of a Molecule Resolved by Atomic Force Microscopy" Science 325, 1110-1114 (2009).
He et al. "A Hydrogen-Bonded Electron-Tunneling Circuit Reads the Base Composition of Unmodified DNA." Nantechnol. 20.7(2009):75102.
He et al. "Identification of DNA Basepairing via Tunnel-Current Delay." Nano Lett. 7.12(2007):3854-3858.
Holt et al. "Fast Mass Transport Through Sub-2-Nanometer Carbon Nanotubes." Science. 312.5776(2006):1034-1037.
Huang et al. "Identifying Single Bases in a DNA Oligomer with Electron Tunnelling." Nat. Nanotechnol. 5.12(2010):868-873.
Keyser et al. "Direct force measurements on DNA in a solid-state nanopore" Nature Physics 2, 473-477 (2006).
Krstic, P. S. Toward Electronic Conductance Characterization of DNA Nucleotide Bases. Solid State Phenomena 121-123, 1387-1390 (2007).
Lagerqvist et al. "Influence of the Environment and Probes on Rapid DNA Sequencing via Transverse Electronic Transport." Biophys. J. 93.7(2007):2384-2390.
Lee et al. "Theory of Tunneling Across Hydrogen-Bonded Base Pairs for DNA Recognition and Sequencing." Phys. Rev. E. Stat Nonlin. Soft Matter Phys. 79.5(2009):051911.
Lee et al. "Insights into electron tunneling across hydrogen-bonded base-pairs in complete molecular circuits for single-stranded DNA sequencing" Journal of Physics: Condensed Matter, Institute of Physics Publishing, Bristol, GB, vol. 21, No. 3, Jan. 21, 2009, p. 35110-3511011.
Lindsay et al. "Molecular Transport Junctions: Clearing Mists" Advanced Materials 19, 23-31 (2007).
Lindsay et al. "Recognition Tunneling" Nanotechnology 21, 262001-262013 (2010).
Liu et al. "Translocation of Single-Stranded DNA Through Single-Walled Carbon Nanotubes." Science. 327.5961(2010):64-67.
Meller et al. "Rapid Nanopore Discrimination Between Single Polynucleotide Molecules." PNAS. 97.3 (2000):1079-1084.
Meller et al. "Voltage-Driven DNA Translocations Through a Nanopore." Phys. Rev. Lett. 86.15(2001):3435-3438.
Meunier et al. "Enhancement of the Transverse Conductance in DNA Nucleotides." J. Chem. Phys. 128.4(2008):041103.
Muthukumar et al. "Simulation of Polymer Translocation Through Protein Channels." PNAS. 103.14(2006):5273-5278.
Nagahara et at "Preparation and Characterization of STM Tips for Electrochemical Studies." Rev. Sci. Instrum. 60(1989):3128-3130.
Nishino et al. "Carbon Nanotube Scanning Tunneling Microscopy Tips for Chemically Selective Imaging." Anal. Chem. 74.16(2002):4275-4278.
Ohshiro et al. "Complementary Base-Pair-Facilitated Electron Tunneling for Electrically Pinpointing Complementary Nucleobases." PNAS. 103.1(2006):10-14.

(56) References Cited

OTHER PUBLICATIONS

Ordejón et al. "Self-Consistent Order-N Density-Functional Calculations for Very Large Systems." Phys. Rev. B. Condens. Matter. 53.16(1996):R10441-R10444.

Pennisi, "Breakthrough of the Year. Human Genetic Variation" Science. 318.5858(2007):1842-1843.

Potier et al. "Synthesis and Hybridization Properties of Oligonucleotides Containing Polyamines at the C-2 Position of Purines: A Pre-Synthetic Approach for the Incorporation of Spermine into Oligodeoxynucleotides Containing 2-(4,9,13-Traizatridecyl)-2'-deoxyguanosine." Chem. Eur. J. 6.22(2000):4188-4194.

Ramachandran et al. "A Bond-Fluctuation Mechanism for Stochastic Switching in Wired Molecules" Science 300, 1413-1415 (2003).

Sankey et al. "Ab initio Multicenter Tight-Binding Model for Molecular-Dynamics Simulations and Other Applications in Covalent Systems." Phys. Rev. B. Condens. Matter. 40.6(1989):3979-3995.

Schäfer et al. "STM Investigations of Thiol Self-Assembled Monolayers." Adv. Mater. 10.11(1998):839-842.

Sharp et al. "Structural Variation of the Human Genome." Annu. Rev. Genomics Hum. Genet. 7(2006):407-442.

Tomfohr et al. "Theoretical Analysis of Electron Transport Through Organic Molecules." J. Chem. Phys. 120.3(2004):1542-1554.

Tsutsui et al. Identification of Single Nucleotide via Tunneling Current. Nature Nanotechnology 5, 286-290 (2010).

U.S. Appl. No. 61/037,647, filed Mar. 18, 2008.

U.S. Appl. No. 61/083,001, filed Jul. 23, 2008.

U.S. Appl. No. 61/103,019, filed Oct. 6, 2008.

Vaught et al. "Non-exponential tunneling in water near an electrode" Chemical Physics Letters 236, 306-310 (1995).

Visoly-Fisher et al. Conductance of a biomolecular wire. Proc. Nat. Acad. Sci. 103, 8686-8690 (2006).

Von Wrochem et al. "Efficient Electronic Coupling and Improved Stability with Dithiocarbamate-Based Molecular Junctions." Nat. Nanotechnol. 5.8(2010):618-624.

Zhang et al. "Synthesis of $3,N^4$-Etheno, $3,N^4$-Ethano, and 3-(2-Hydroxyethyl) Derivatives of 2'-Deoxycytidine and Their Incorporation into Oligomeric DNA." Chem. Res. Toxicol. 8.1(1995):148-156.

Zikic et al. "Characterization of the Tunneling Conductance Across DNA Bases." Phys. Rev. E. Stat. Nonlin. Soft Matter Phys. 74.1(2006):011919.

Zwolak et al. "Colloquium: Physical Approaches to DNA Sequencing and Detection" Rev. Mod. Physics. 80.1(2008):141-165.

Zwolak et al. "Electronic Signature of DNA Nucleotides via Transverse Transport." Nano Lett. 5.3 (2005):421-424.

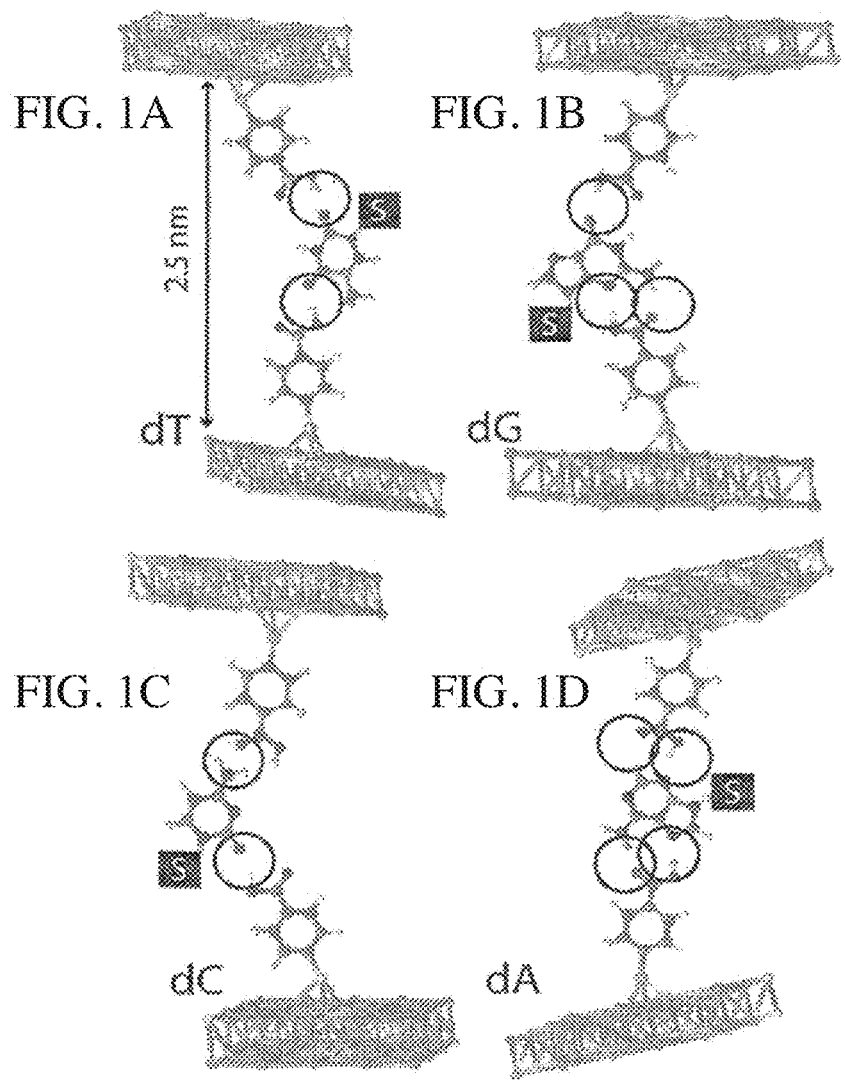

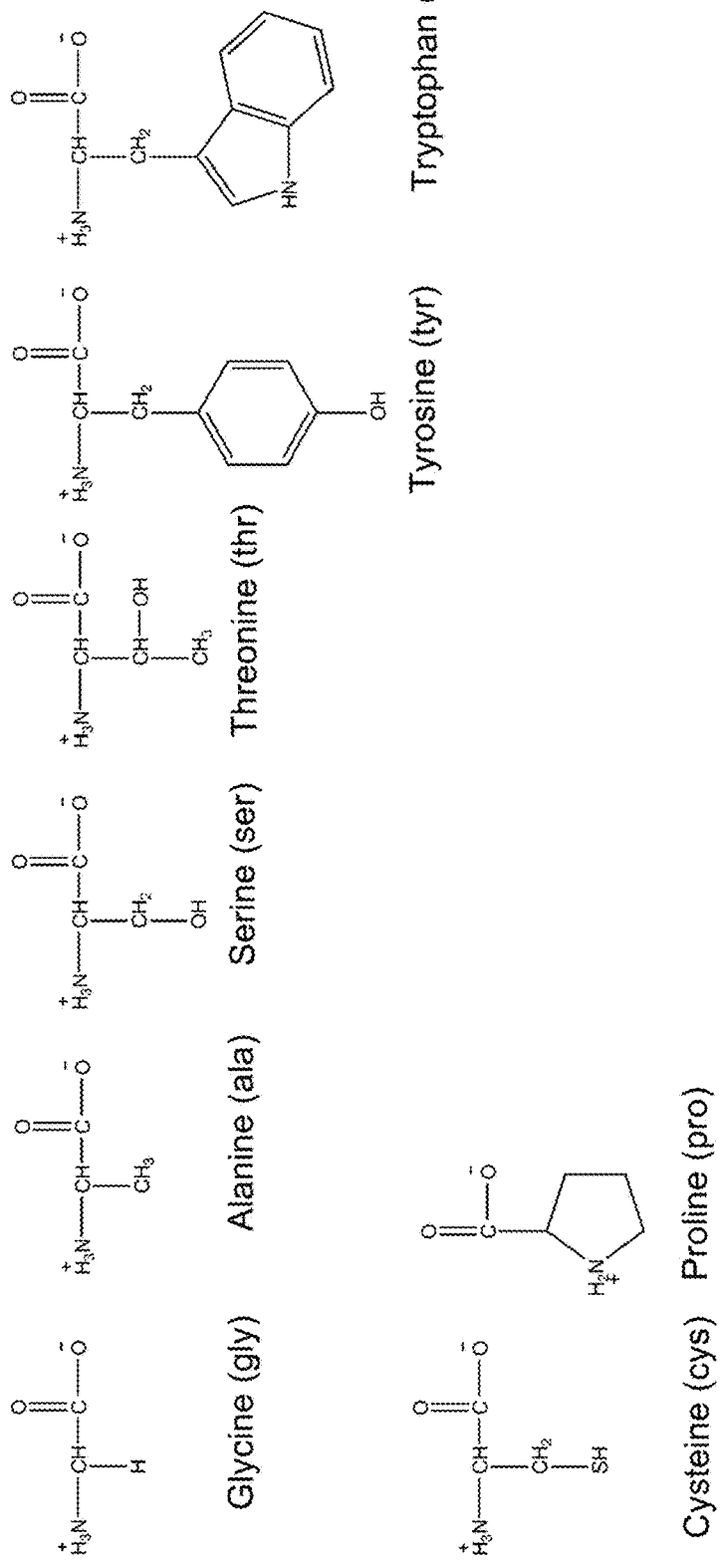
FIG. 13 (contd)

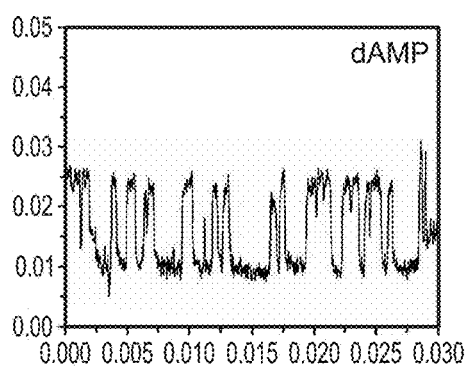
FIG. 56C
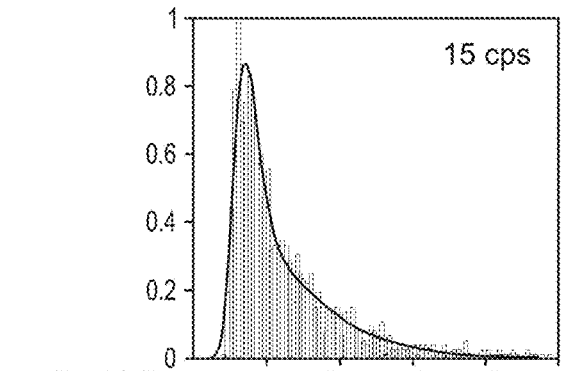
FIG. 56G
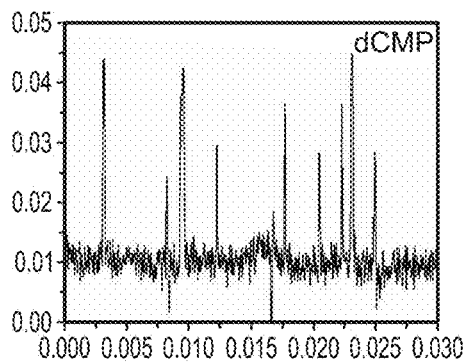
FIG. 56D
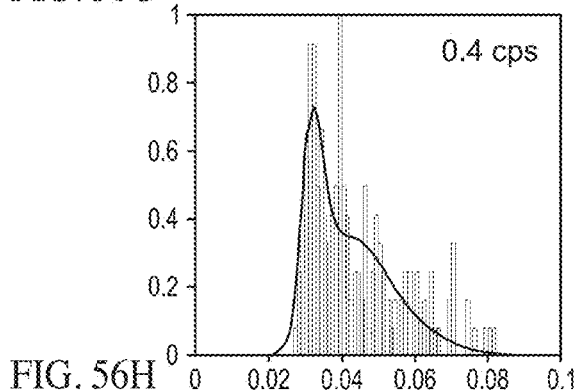
FIG. 56H
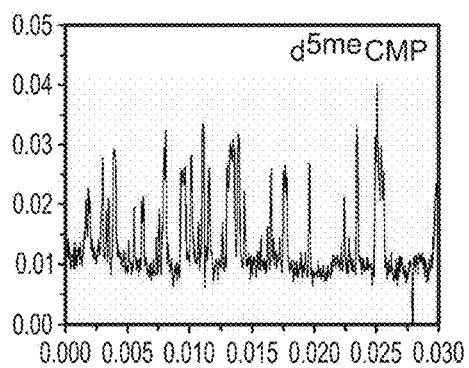
FIG. 56E
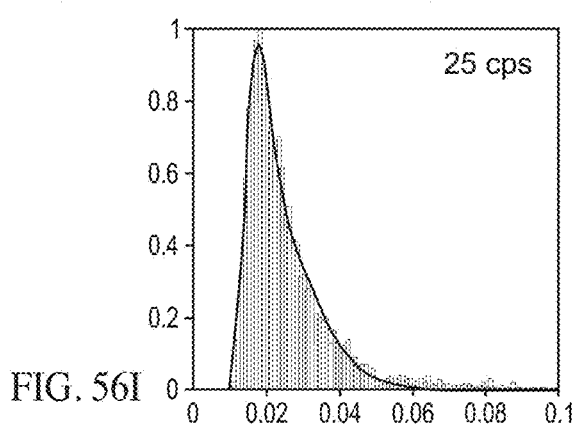
FIG. 56I
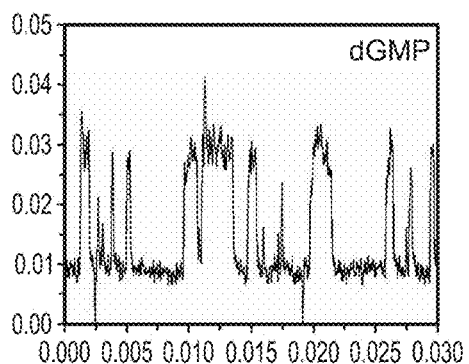
FIG. 56F  Time (s)
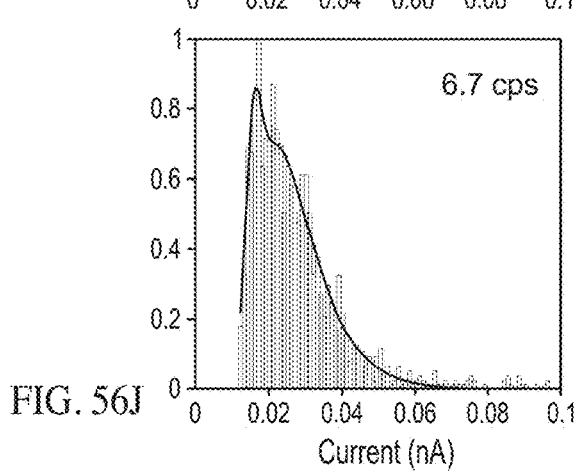
FIG. 56J  Current (nA)

CONTROLLED TUNNEL GAP DEVICE FOR SEQUENCING POLYMERS

REFERENCE TO RELATED APPLICATIONS

This application is a continuation application of U.S. patent application Ser. No. 14/851,933 (allowed), filed on Sep. 11, 2015, which is a continuation application of U.S. patent application Ser. No. 13/395,956, now U.S. Pat. No. 9,140,682, filed on May 22, 2012, which is a US national stage entry of PCT/US2011/023185, filed on Jan. 31, 2011, which claims priority to U.S. Provisional Patent Application No. 61/300,678, filed on Feb. 2, 2010, and to U.S. Provisional Patent Application No. 61/378,838, filed on Aug. 31, 2010, the contents of each of which are incorporated herein by reference in their entireties.

GOVERNMENT RIGHTS

This invention was made with government support under R01 HG006323 awarded by the National Institutes of Health. The government has certain rights in the invention.

BACKGROUND OF THE INVENTION

New approaches to DNA sequencing are required to reduce costs and increase the availability of personalized genomics (M. Zwolak, M. Di Ventra, Reviews of Modern Physics 80, 141 (2008)). In addition, long contiguous reads would help to unravel the long-range structure of the genome (E. Pennish, Science 318, 1842 (2007); A. J. Sharp, et al., Annu. Rev. Genomic Hum. Genet. ARJ, 407 (2006). In contrast to Sanger sequencing and next-generation methods, nanopore sequencing (D. Branton et al., Nature Biotechnology 26, 1146 (2008)) is an enzyme-free technique in which DNA molecules are forced through a tiny aperture using electrophoresis, so that a sequence-reading mechanism could maintain its fidelity over the entire length of a molecule. Ion current that passes through the pore is sensitive to the sequence in the nanopore (M. Akeson, et al., Biophys J. 77, 3227 (1999); A. Meller, et al., Proc. Natl. Acad. Sci. (USA) 97, 1079 (2000); N. Ashkenasy, et al., Angew. Chem. Int. Ed. 44, 1401 (2005)) but all of the bases in the nanopore channel contribute to the current blockade (A. Meller, et al., Phys. Rev. Lett. 86, 3435 (2001)) as well as those in the region of high field beyond the pore (A. Aksimentiev, et al., Biophysical Journal 87, 2086 (September, 2004); M. Muthukumar, et al., Proc. Natl. Acad. Sci. (USA) 103, 5273 (2006)). In consequence, single base resolution has not yet been attained with an ion current readout. Lee and Thundat proposed that electron tunneling across a DNA molecule might be localized enough to sense and identify single nucleotides (J. W. Lee, and T. Thundat. U.S. Pat. No. 6,905,586 (2005)), a conjecture supported by the calculations of Zwolak and Di Ventra (M. Zwolak, M. Di Ventra, Nano Lett. 5, 421 (2005)). Further calculations show that thermal motion of molecules in the gap broadens the distribution of tunnel currents (J. Lagerqvist, et al., Biophys J. 93, 2384 (2007); R. Zikic et al., Phys. Rev. E 74, 011919 1 (2006)), reducing selectivity substantially. The range of orientations of molecules in a tunnel gap can be greatly reduced by using chemical bonds to tether it to the readout electrodes (X. D. Cui et al., Science 294, 571 (200 I)), however, the use of strong bonds is not an option for DNA sequencing where the contact to the electrodes must slide from one nucleotide to the next rapidly. Ohshiro and Umezawa demonstrated that hydrogen bonds can be used to provide chemical contrast in scanning tunneling microscope images (T. Ohshiro, Y. Umezawa, Proc. Nat. Acad. Sci. 103, 10 (2006)) suggesting that these weaker bonds can serve as "sliding contacts" to single molecules.

In applications W02008124706A2 ("Sequencing by Recognition"), 61/037,647 (Nanotube Nanopore for DNA Sequencing"), 61/083,001) ("Tandem Reader for DNA Sequencing.") 61/083,993 ("Carbon Nanotube Based Device for Sequencing Polymers"), 61/103,019 ("A Transbase tunnel Reader for Sequencing"), all of which are incorporated by reference, schemes for contacting target bases in DNA in a tunnel gap with electrodes functionalized with reagents designed to hydrogen bond specifically to one base or another are described. In consequence, a different reader is required for each DNA base, so that a sequence has to be assembled by aligning the output of four separate readers. Furthermore, the reliance on reagents designed to target a specific site means that when two different sites are targeted (one by each electrode) the electrodes have to be functionalized independently, which is difficult to achieve in a nanoscale gap.

SUMMARY OF THE INVENTION

The present invention provides compositions, devices, and methods for analyzing a polymer and/or polymer unit. The polymer may be a homo- or hetero-polymer such as DNA, RNA, a polysaccharide, or a peptide. The device has electrodes that form a tunnel gap through which the polymer can pass. The electrodes are functionalized with a reagent attached thereto, and the reagent is capable of forming a transient bond to a polymer unit. When the transient bond forms between the reagent and the unit, a detectable signal is generated and used-to analyze the polymer. The tunnel gap width is configured or adjusted to optimize selectivity of the signal generated when the electrodes form a transient bond to the unit of the polymer.

BRIEF DESCRIPTION OF THE FIGURES

FIGS. 1A-1D illustrate hydrogen bonding for T (FIG. 1A), G (FIG. 1B), C (FIG. 1C), and A (FIG. 1D) with electrodes functionalized with 4-mercaptobenzamide.

FIG. 2A is at a current of 10 pA and FIG. 2B is at a current of 2 pA.

FIG. 3F shows the distribution for a mixture of dA and dG. The assignment of the higher peak to dA is confirmed by the distribution measured with a reduced concentration of dA (FIG. 3H). The high current tail in FIGS. 3F and 3H is consistent with a small number of two molecule (dA+dG) reads. Distributions of the spike widths are given in FIG. 29.

FIG. 7A shows peak current for dA (filled squares) and dT (filled circles) as a function of the baseline conductance (at V=0.5V). Open squares (dA) and open circles (dT) show how the fraction of two molecule reads increases as the tunnel gap is made smaller. FIG. 7A shows that the measured molecular conductance increases linearly with $G_{b1}$ (black circles dT, black squares dA, error bars are ±HWHH). The number of two molecule reads (open circles, dT, open squares, dA) increases at $G_{b1}$=20 pS, and the read rate is substantially reduced at $G_{b1}$=4 pS. FIG. 7B provides peak currents measured in three independent runs for the four nucleosides (cross hatched bars). FIG. 7B shows that with both electrodes functionalized, a narrow distribution of current peaks is observed at a characteristic current for each nucleoside. Cross-hatched boxes (3 repeated data sets) show peak currents for each nucleoside measured at a baseline current of 6 pA, V=0.5V. The error bars on each box represent the full-width of the measured current distributions. The shaded boxes show the currents measured when only one of the two electrodes is functionalized. Reads for a functionalized surface and a bare Pt (light shaded bars) and bare Au (dark shaded bars) probe are relatively insensitive to the identity of the nucleoside, as shown quantitatively in FIG. 7C where the junction resistance is plotted vs. the molecular resistance determined with two functionalized probes.

FIG. 34A is an optical image of a bare electrode. FIGS. 34B and 34C are TEM images of a bare electrode. FIG. 34D is an optical image of a coated electrode. FIGS. 34E and 34F are TEM images of coated electrodes. The dashed arc in 34 C has a radius of 16 nm. The arrows in 34E and 34F indicate the location of the exposed gold.

Figures 37A, 37B, 37C:
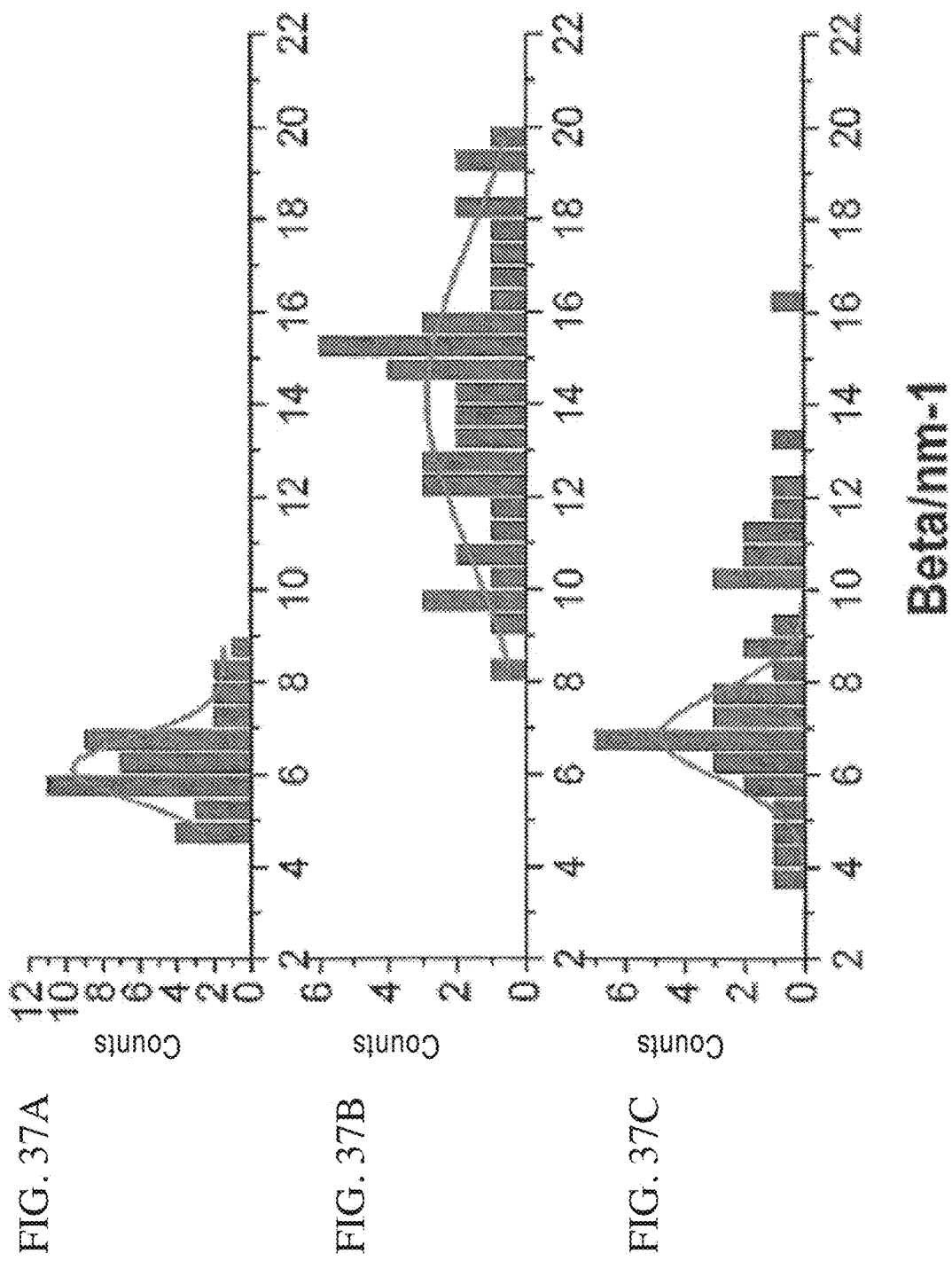
FIGS. 37A-37C show exemplary histograms of beta, the negative of the slope of the logarithmic decay curves $$i - \frac{d\ln(i)}{dz}.$$

Values are obtained in pure water for bare gold electrodes (FIG. 37A), functionalized electrodes with mercaptobenzamide (FIG. 37B), and one bare and one functionalize electrode with mercaptobenzamide (FIG. 37C). Gausian fits (mean±SD) yield: 37A→6.11±0.68 m$^{-1}$, 37B→14.16±3.20 nm$^{-1}$;→and 37C 6.84±0.92 nm$^{-1}$.

Figure 38:
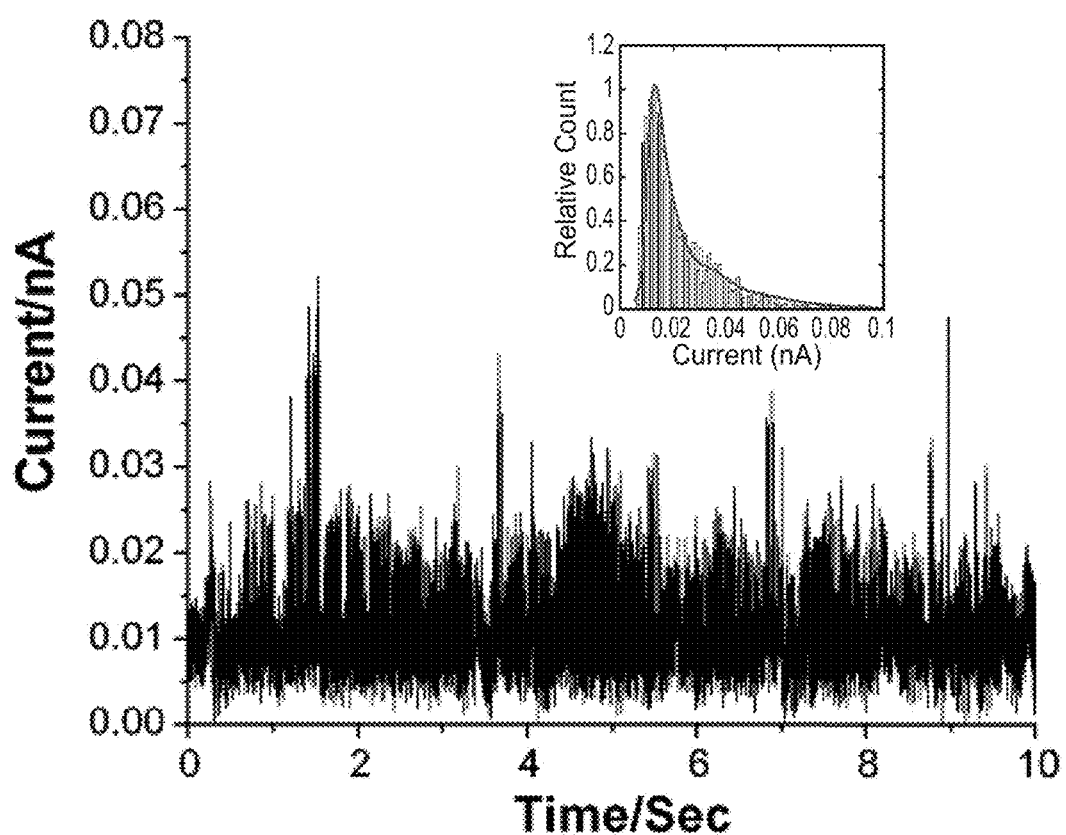
Figure 39A:
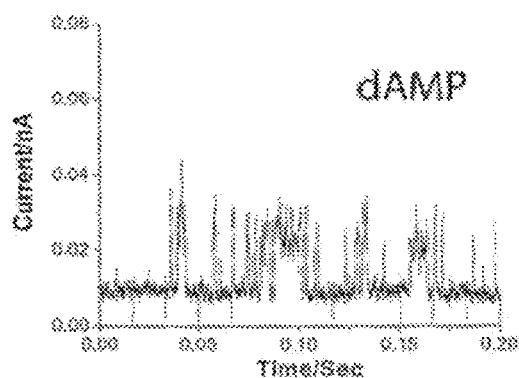
Figure 39B:
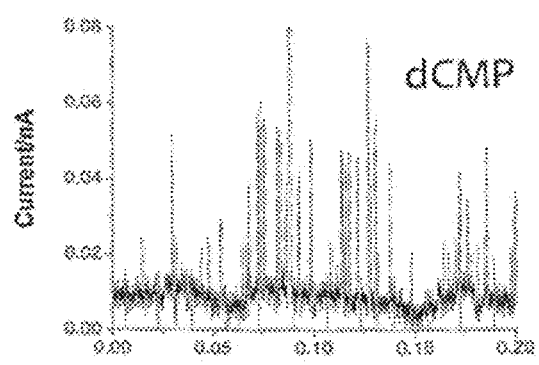
Figure 39C:
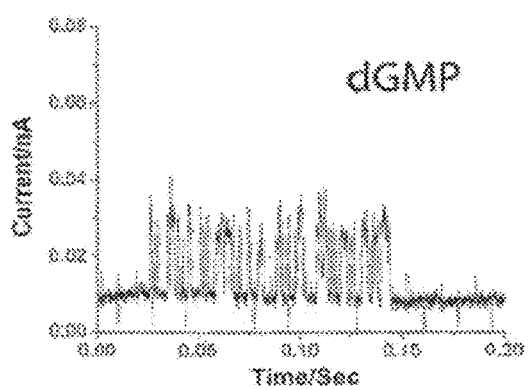
Figure 39D:
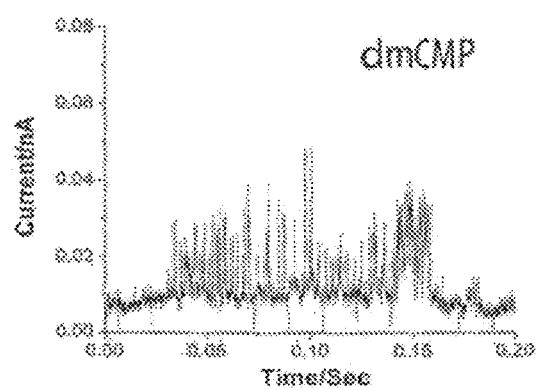

FIG. 38 shows an exemplary 10 s time trace for d(CCACC) taken using 4-mercapto benzamide reader molecules. Note the preponderance of A-signals. The current spike distribution (inset) is almost completely dominated by A-signals with the C component in the fit (black line) being 7% or less. This shows that the probe spends more time bound to the minority of A bases.

FIGS. 39A-39D show exemplary current spike traces over time for the dAMP (FIG. 39A), dCMP (FIG. 39B), dGMP (FIG. 39C), and dmCMP (FIG. 39D) showing exemplary bursts of data. Each of these examples is surrounded by spike-free regions of current.

Figure 40:
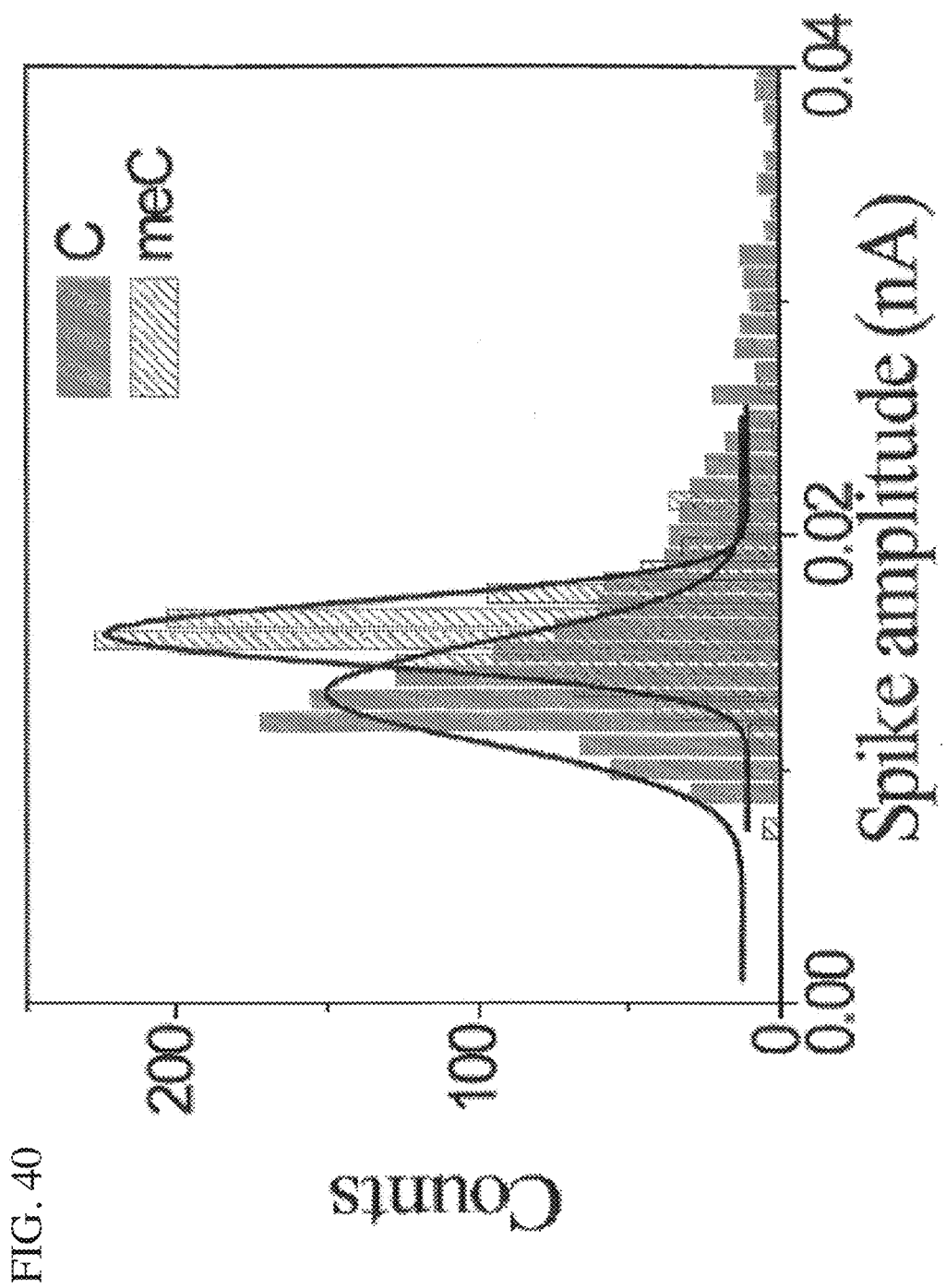

FIG. 40 illustrates exemplary current distributions measured for cytidine (grey) and $^{5me}$cytidine using benzoic acid readers trichlorobenzene solvent.

Figure 41:
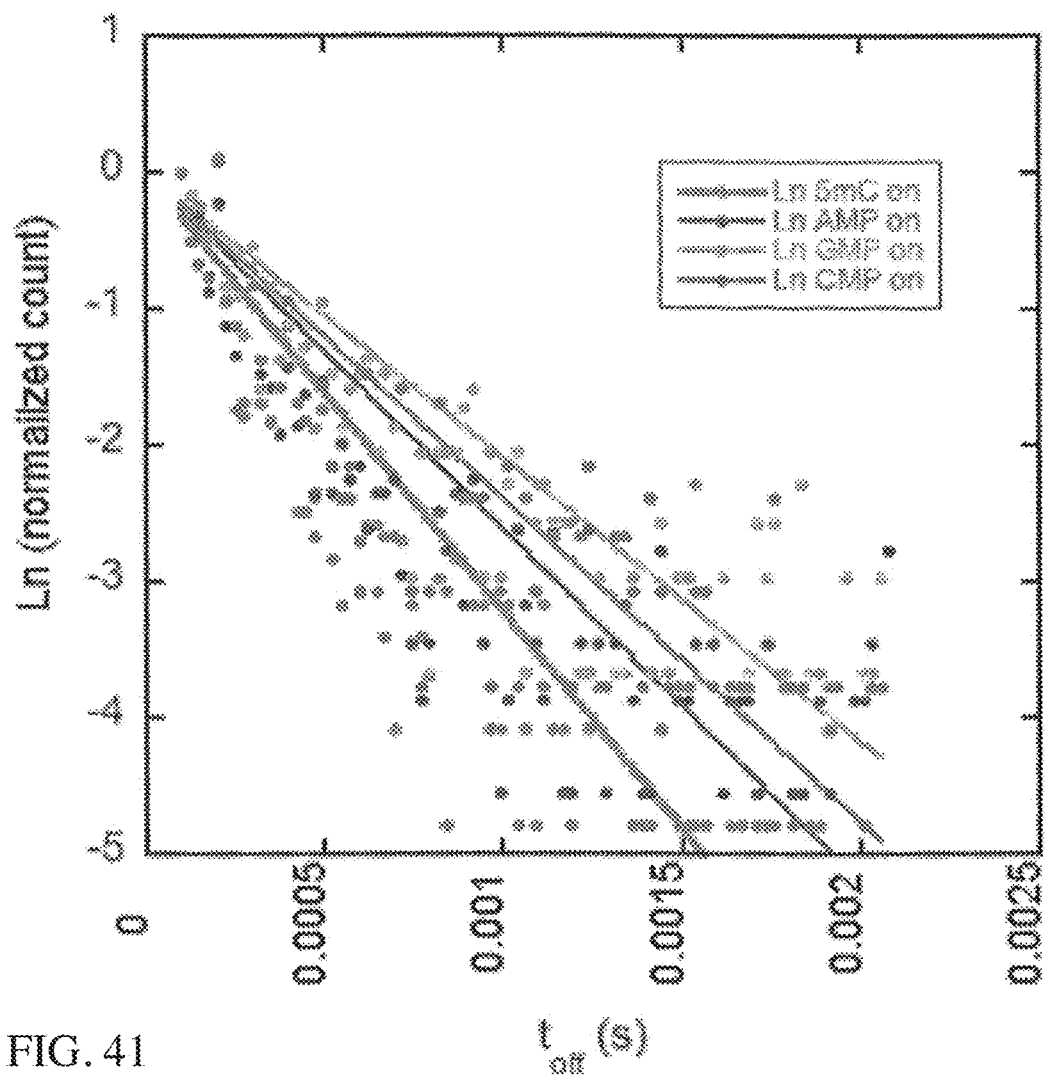

FIG. 41 shows exemplary distribution of "on times" for dGMP, dCMP, dAMP, and d$^m$CMP monomers with the solid lines being exponential fits.

Figure 42:
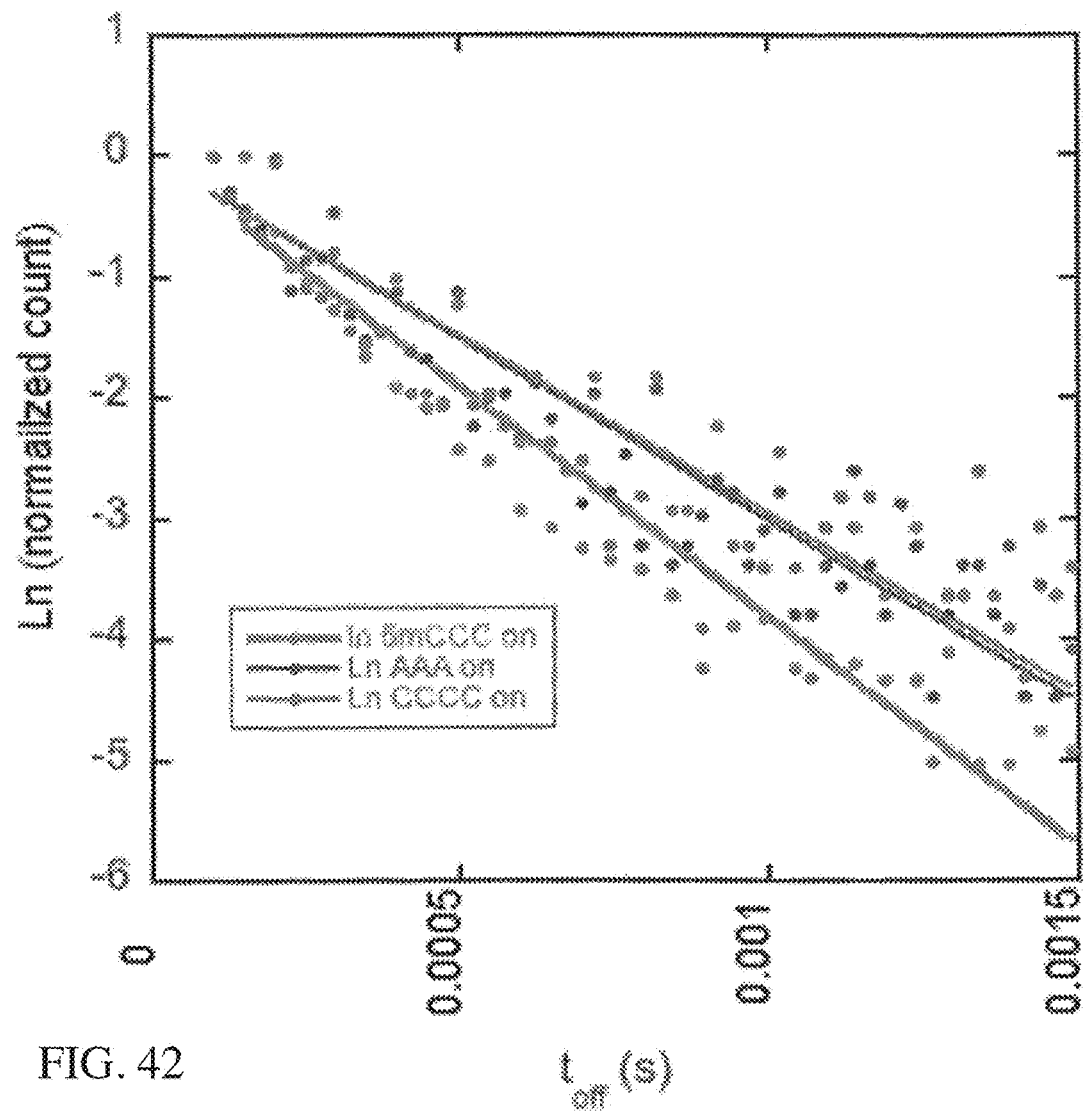

FIG. 42 shows exemplary distribution of "on times" for $d(C)_5$, $d(A)_5$, and $d(^mC)_5$ polymers with the solid lines being exponential fits.

Figure 43:
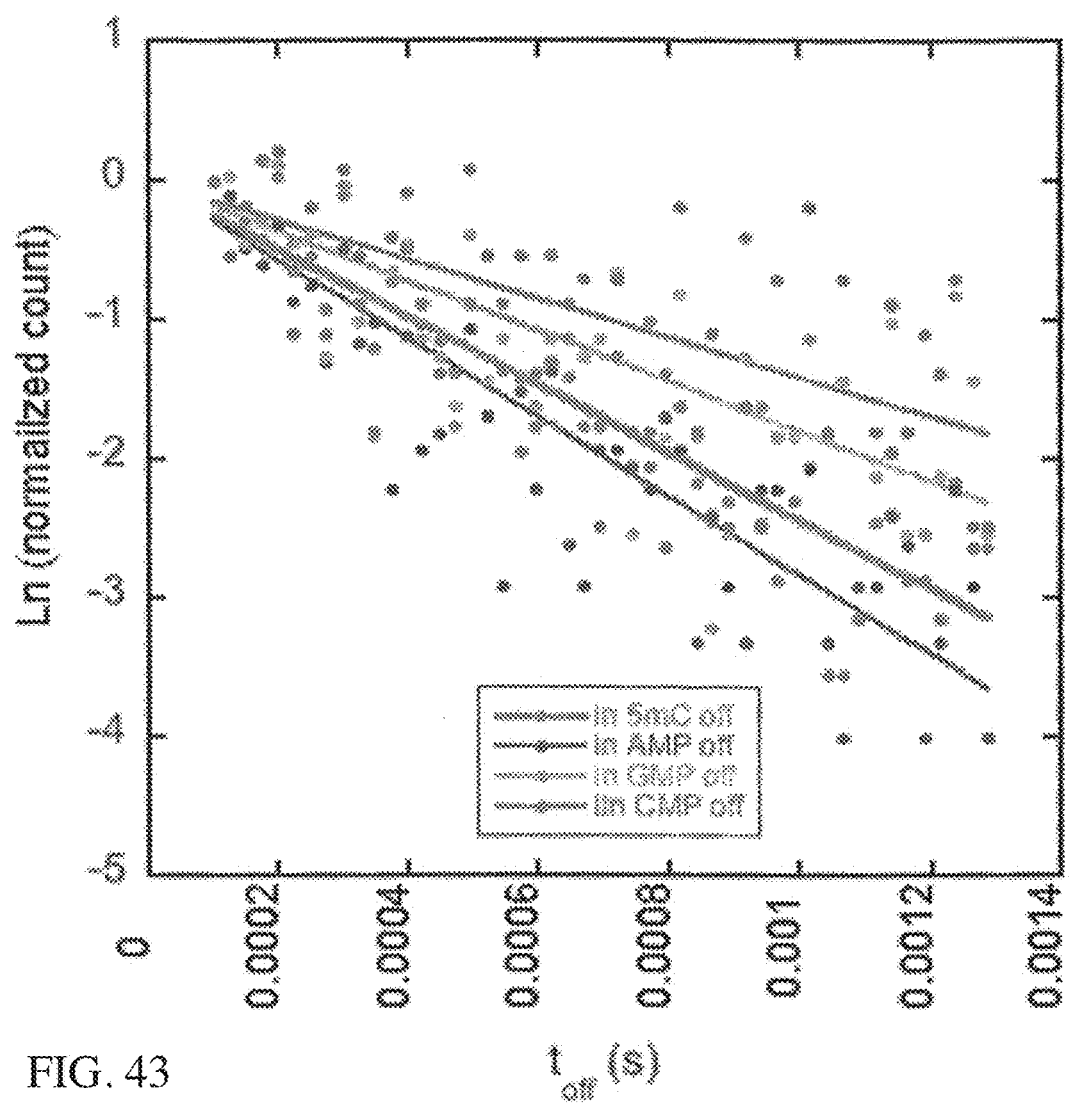

FIG. 43 shows exemplary distribution of "off times" for dGMP, dCMP, dAMP, and d$^m$CMP monomers with the solid lines being exponential fits.

Figure 44:
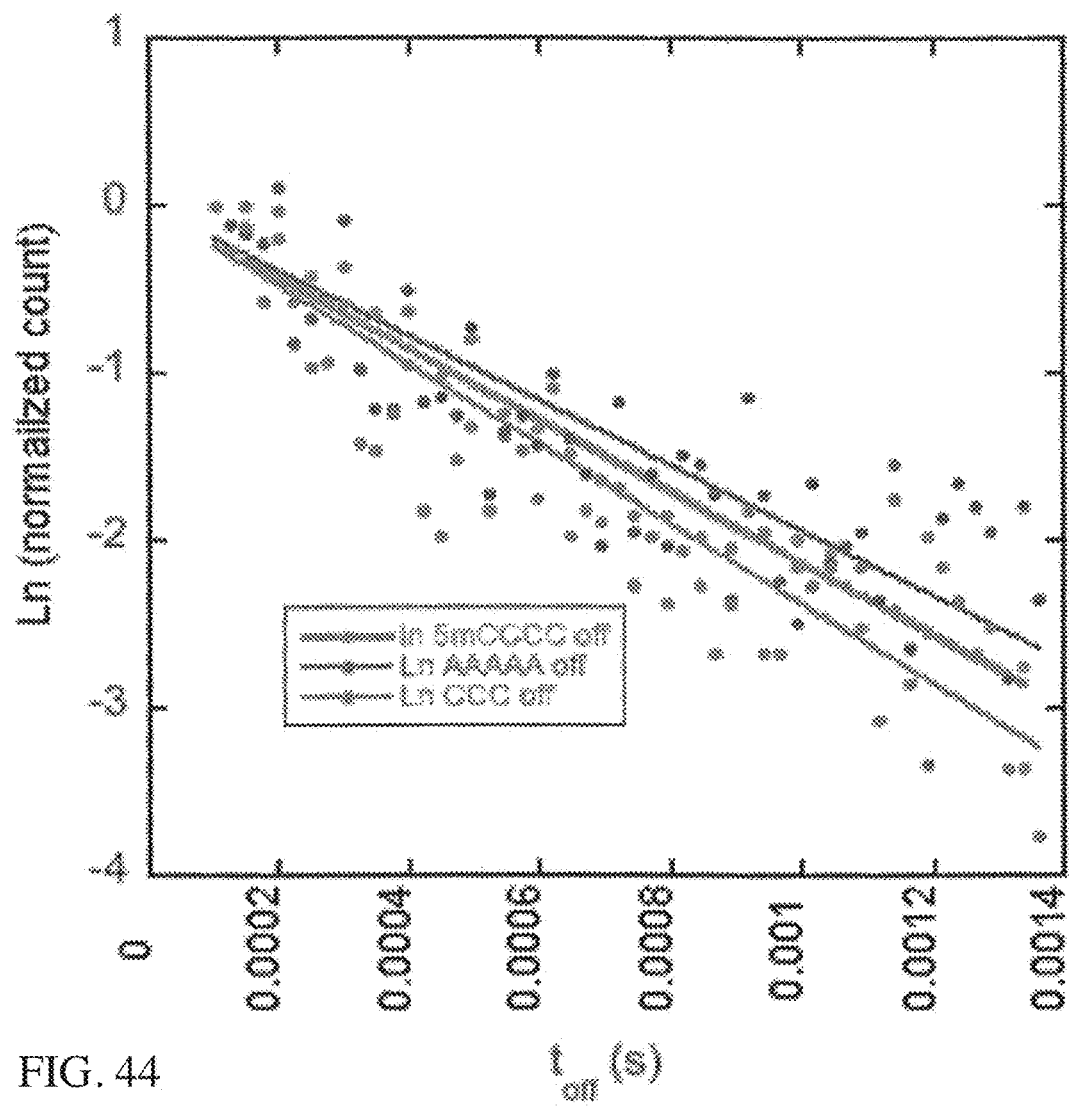

FIG. 44 shows exemplary distribution of "off times" for $d(C)_5$, $d(A)_5$, and $d(^mC)_5$ polymers with the solid lines being exponential fits.

Figure 45:
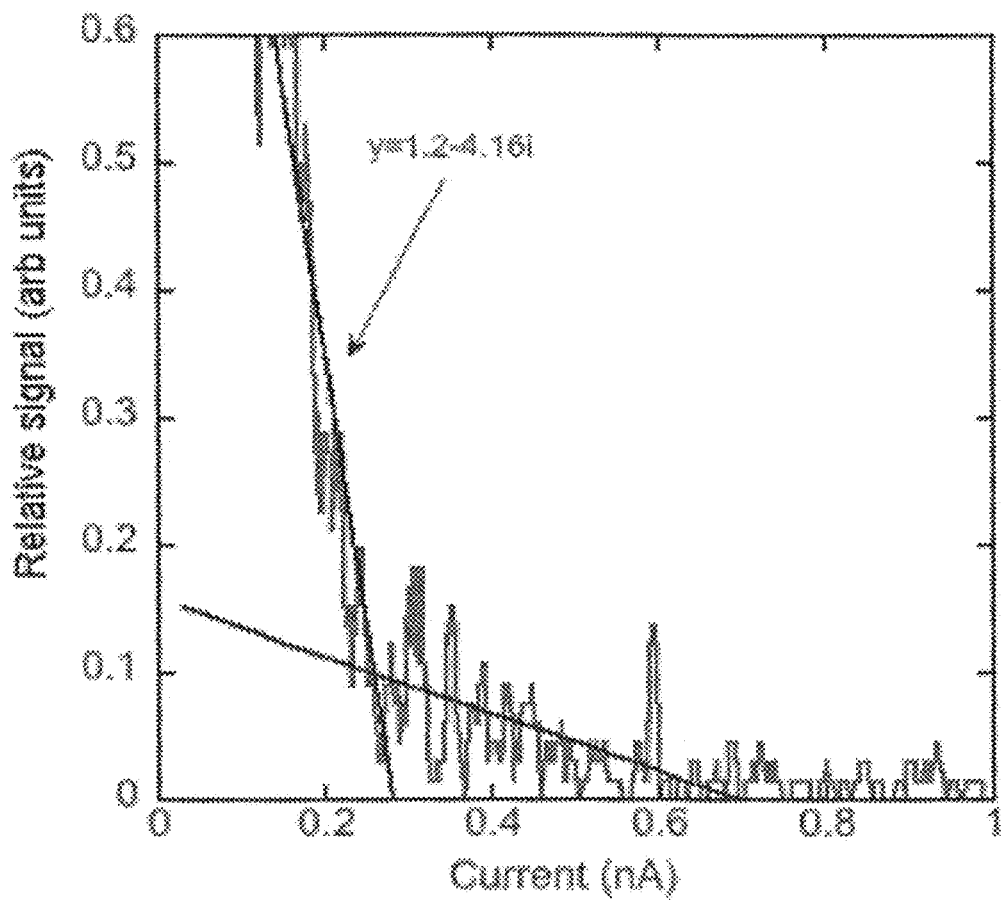

FIG. 45 shows an exemplary distribution of counts for spikes >0.1 nA for d(A)$_5$. These are about 20% of the total and are not observed in dNTPs or d(C)$_5$.

Figure 46:
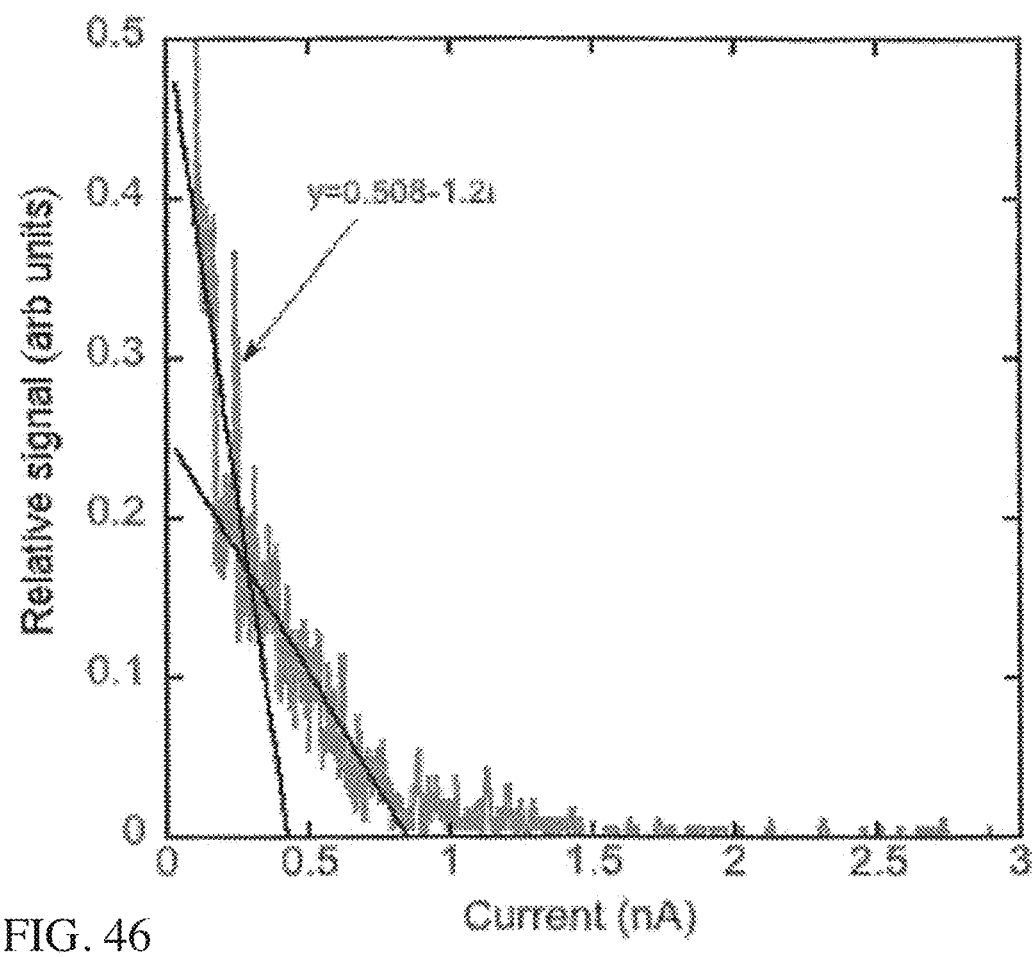

FIG. 46 shows an exemplary distribution of counts for spikes >0.1 nA for d($^m$C)s. These are about 20% of the total and are not observed in dNTPs or d(C)$_5$.

Figure 47:
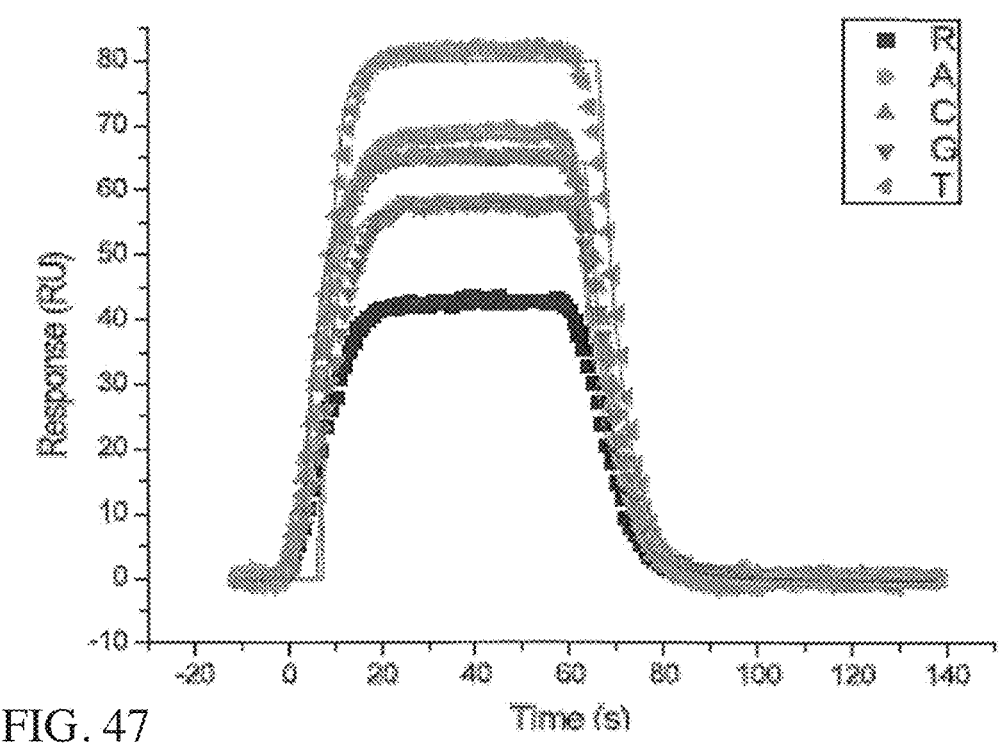

FIG. 47 shows exemplary SPR sensorgrams of nucleoside-5'-monophosphates (A, C, G, T, R) interacting with the benzamide surface (R: 2-Deoxoribose 5-phosphate sodium salt containing no DNA base). The lines are fitted curves modeled to describe a 1:1 binding event.

Figure 48A:
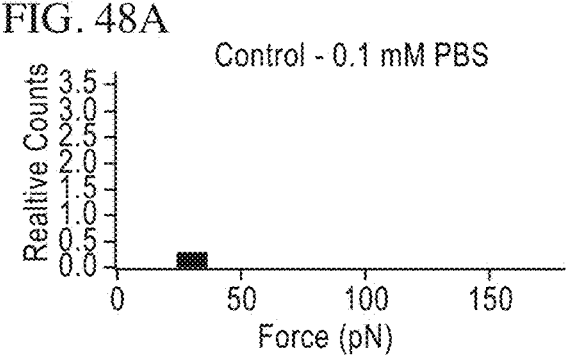
Figure 48B:
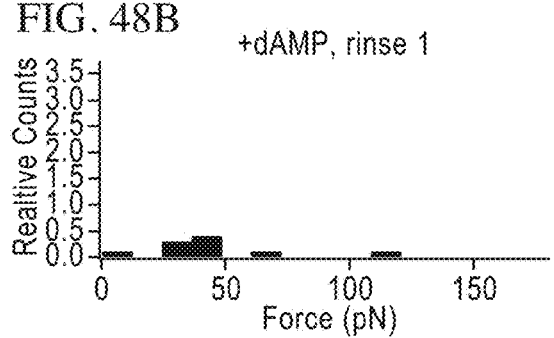
Figure 48C:
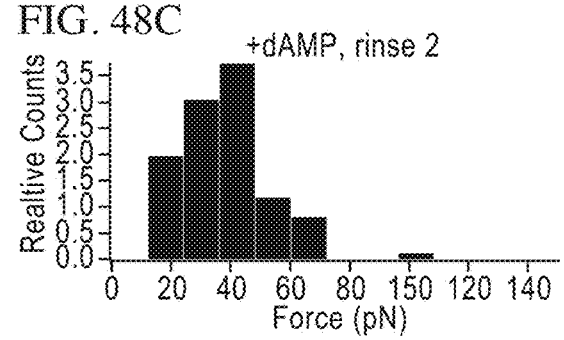
Figure 48D:
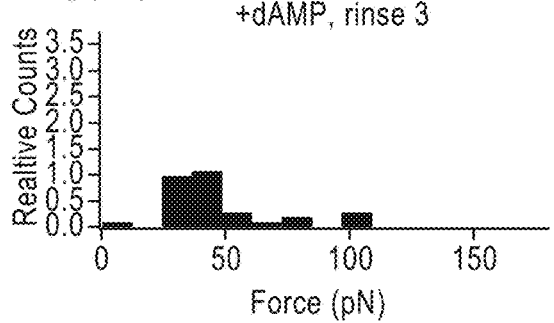
Figure 48E:
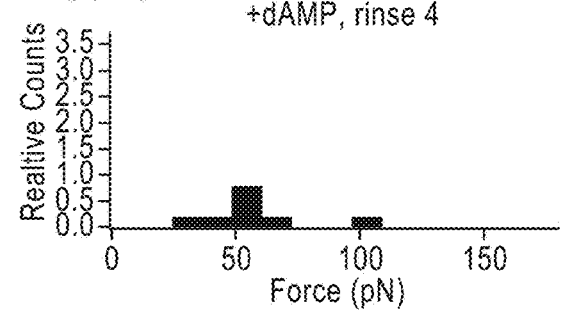

FIGS. 48A-48E show histograms of adhesion events, as recorded with an atomic force microscope, for a pair of 4-mercaptbenzamide reader molecules trapping dAMP. FIG. 48A shows a control taken in the absence of dAMP, which showed almost no adhesion events between the benzamide molecules, presumably because they were blocked by water. FIG. 48B shows the adhesion of dAMP after a first rinse. FIG. 48C shows adhesion of dAMP after a second rinse. FIG. 48D shows adhesion of dAMP after a third rinse. FIG. 48E shows adhesion of dAMP after a fourth rinse. Addition of dAMP led to a number of adhesion events that increase as excess dAMP was rinsed out of the system (FIGS. 48B, 48C) and then decreased as the rinsing continued (FIGS. 48D, 48E).

Figure 49:
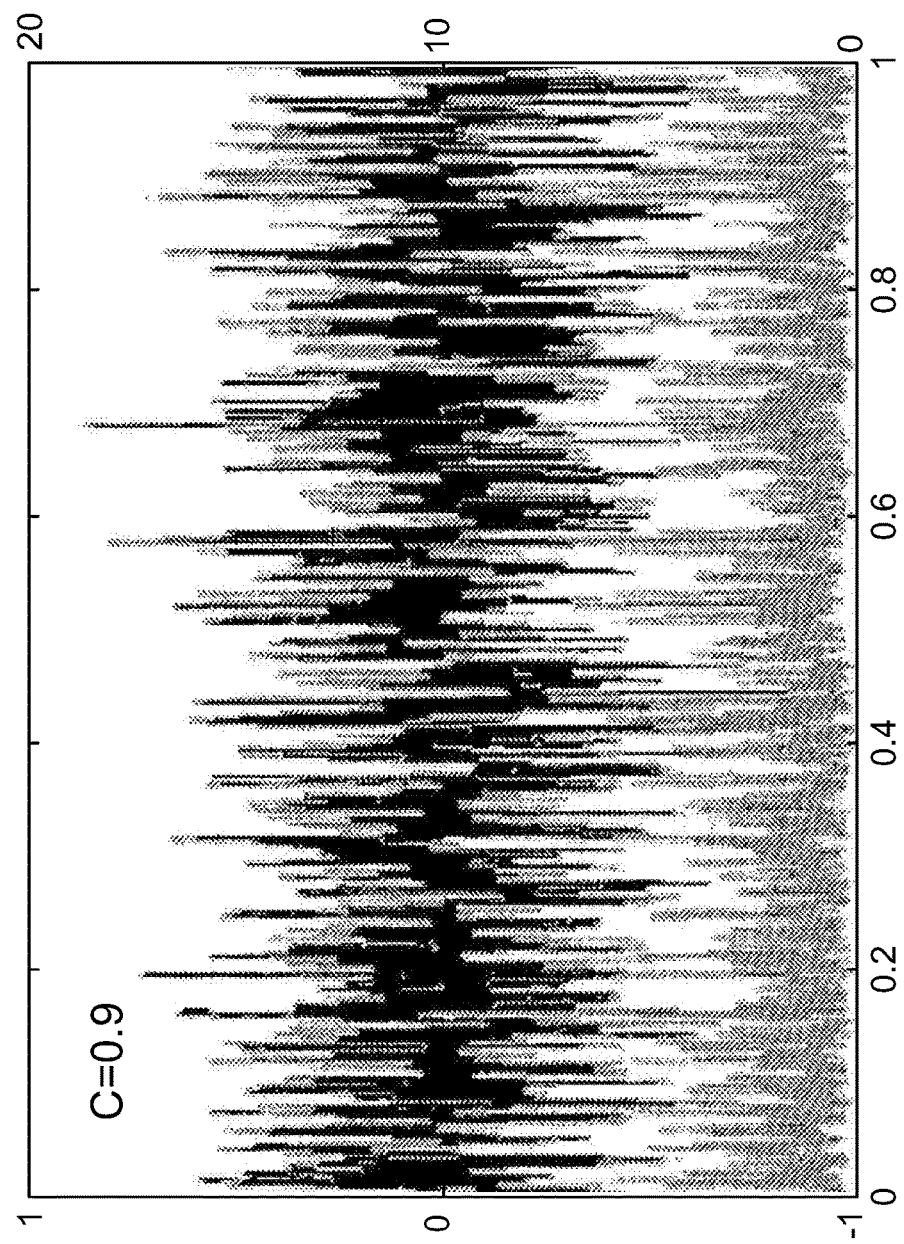

FIG. 49 shows exemplary simulated displacement (top pattern—black) and current (bottom pattern-grey) vs. time-steps where the correlation, C, has a value of 0.9.

Figure 50:
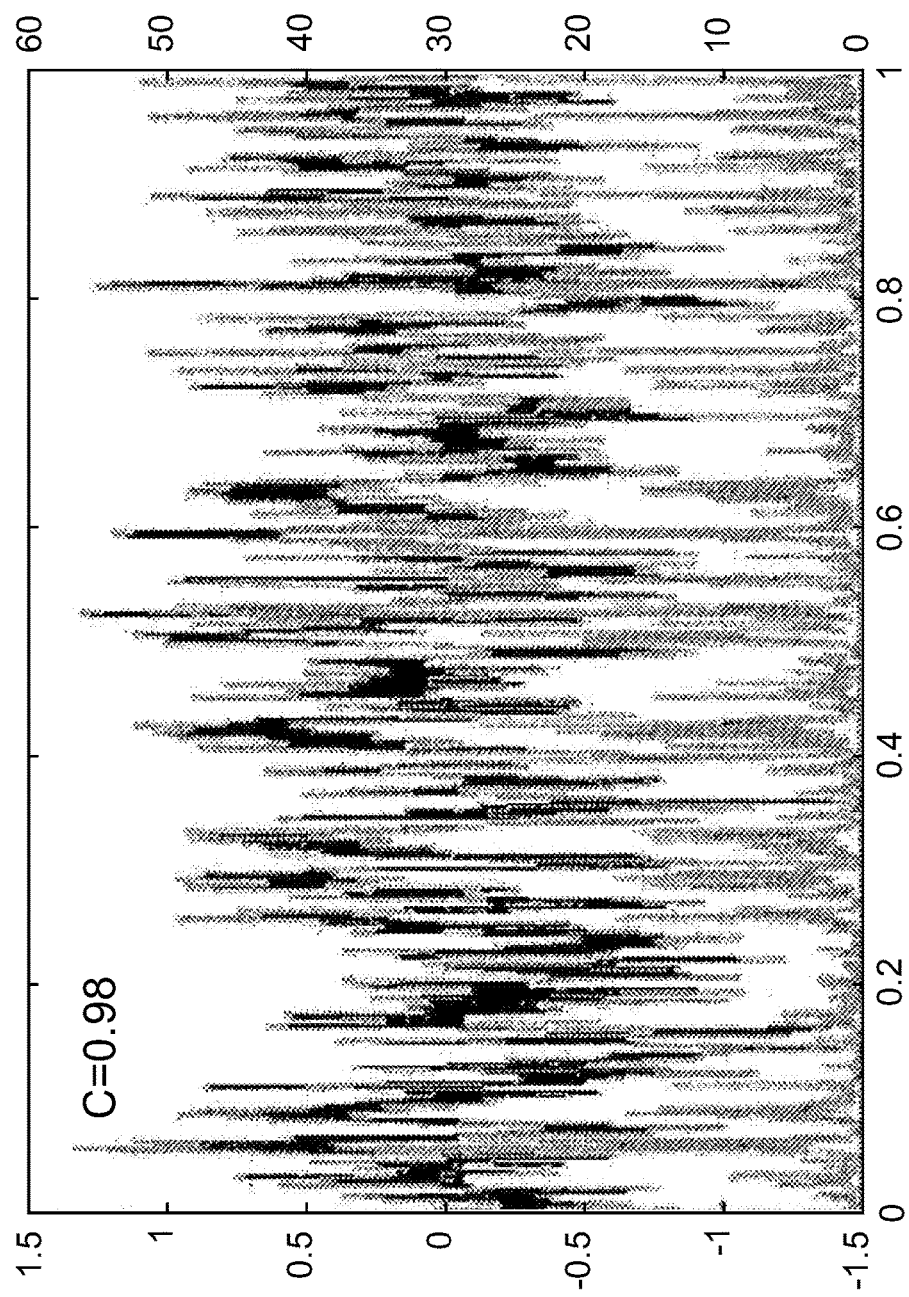

FIG. 50 shows exemplary simulated displacement (top pattern—black) and current (bottom pattern-grey) vs. time-steps where the correlation, C, has a value of 0.98.

Figure 51:
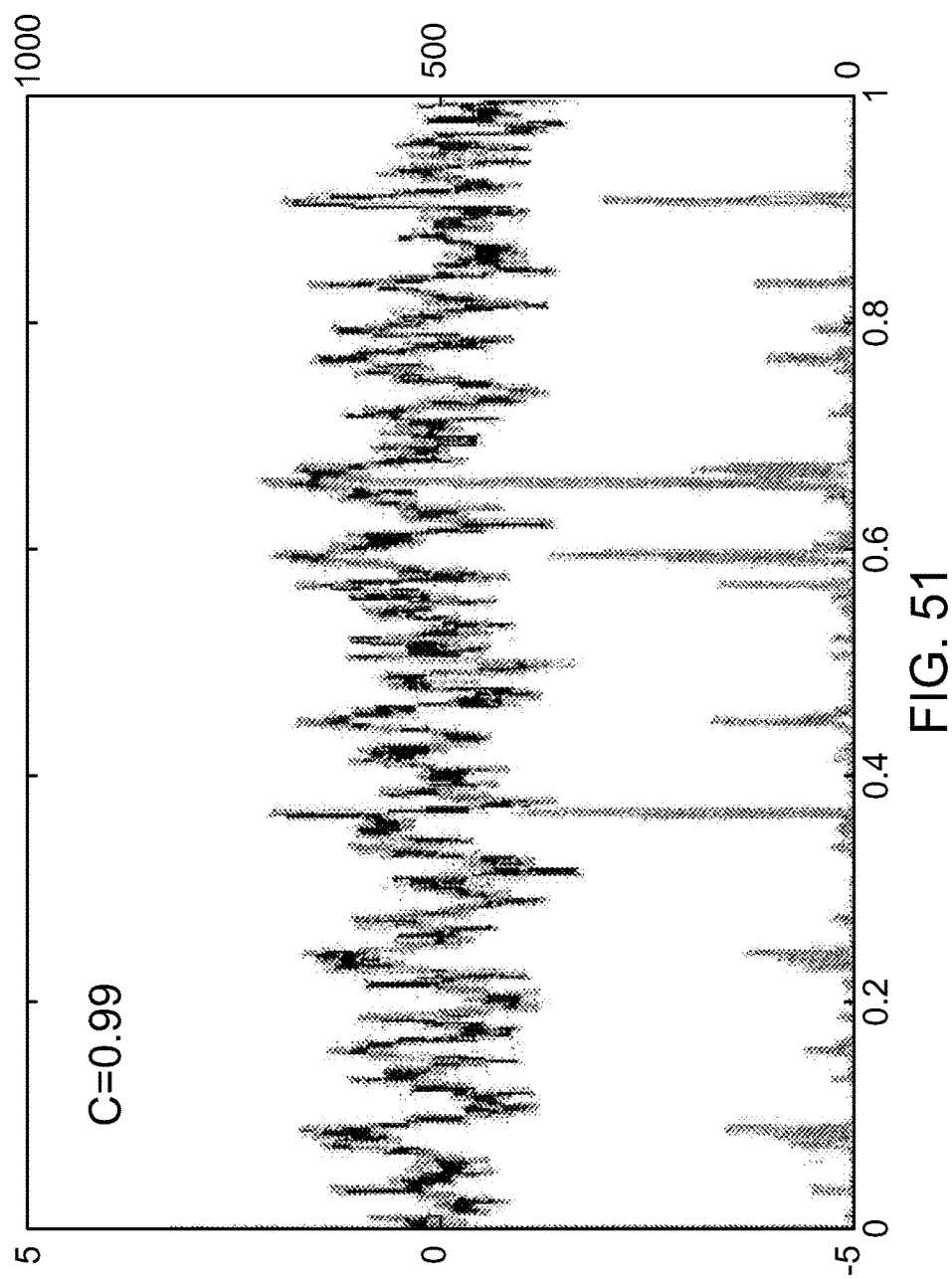

FIG. 51 shows exemplary simulated displacement (top pattern—black) and current (bottom pattern-grey) vs. time-steps where the correlation, C, has a value of 0.99.

FIGS. 52A-52B shows exemplary normalized distributions for signals obtained from homopolymers. FIG. 52A shows fits to normalized current distributions. FIG. 52B shows normalized spike frequencies in a signal burst, fitted with polynomials. The fits to the distributions are used to assign the probability that a particular noise burse originates from an A or a C (if the average currents and frequencies lie above or below the crossover points labeled "$1_{AC}$" and "$f_{AC}$"). Current distributions for C and $^m$C are separated (crossover point labeled "$I_{mC}$") but frequency distributions overlap.

Figure 53:
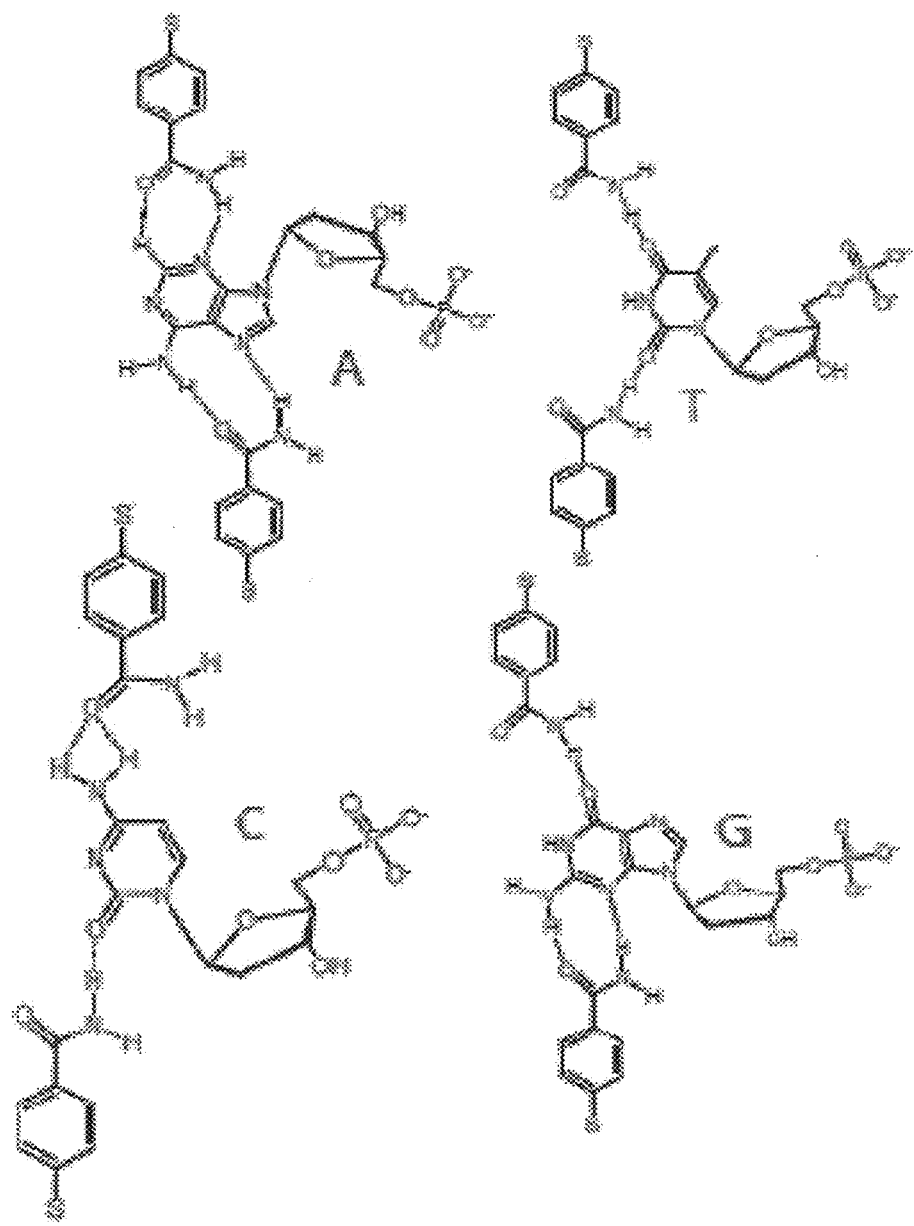

FIG. 53 shows exemplary hydrogen bonding modes of 4-mercaptobenzamide for adenine, thymine, cytosine, and guanine.

Figure 54B:
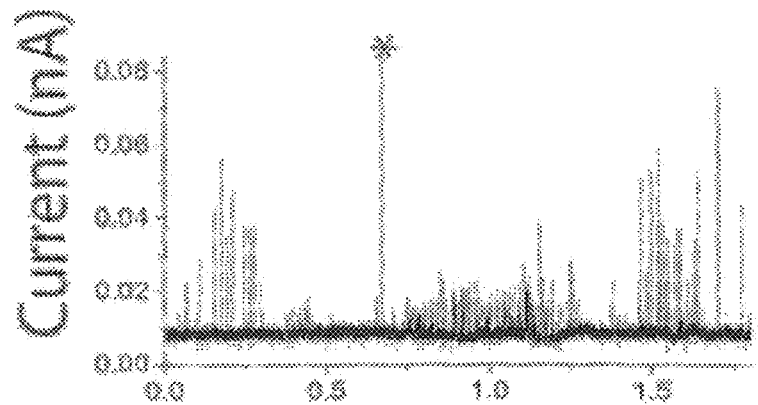
Figure 54C:
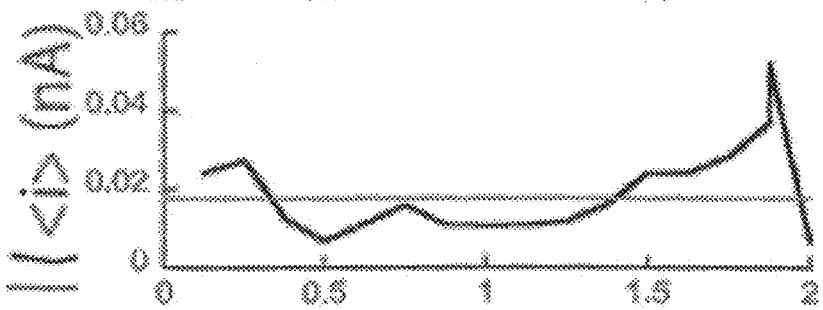
Figure 54D:
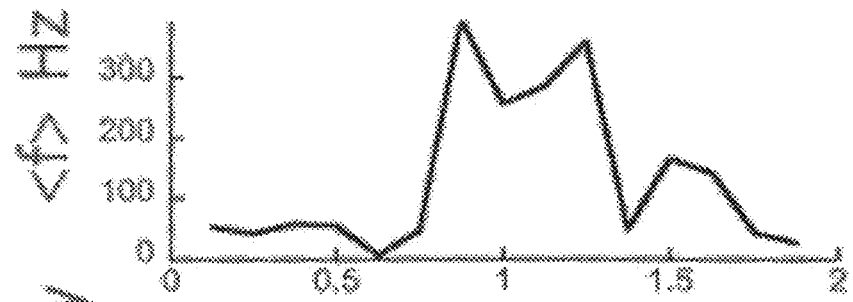
Figure 54E:
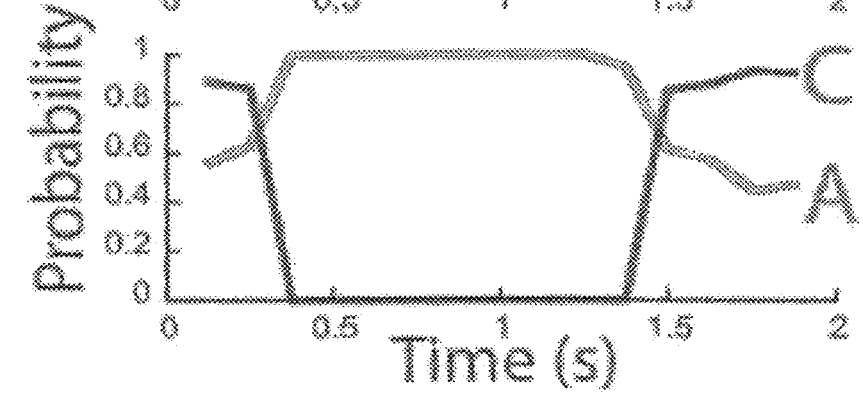

FIGS. 54B-54E shows exemplary data from reading a single base within a heteropolymer. 54B shows exemplary bursts of tunneling noise with large, infrequent spikes signaling C and smaller, more frequent spikes signaling A. The "*" labeled spike is nonspecific. FIG. 54C shows the rolling average of the spike height (0.25 s window, 0.125 s steps). C bases generate a negligible number of spikes below 0.015 nA (straight line). FIG. 54D shows the rolling average of the spike frequency. FIG. 54E shows the probability that the signal comes from an A (shown by the light grey line) or a C (shown by the darker line).

Figure 55:
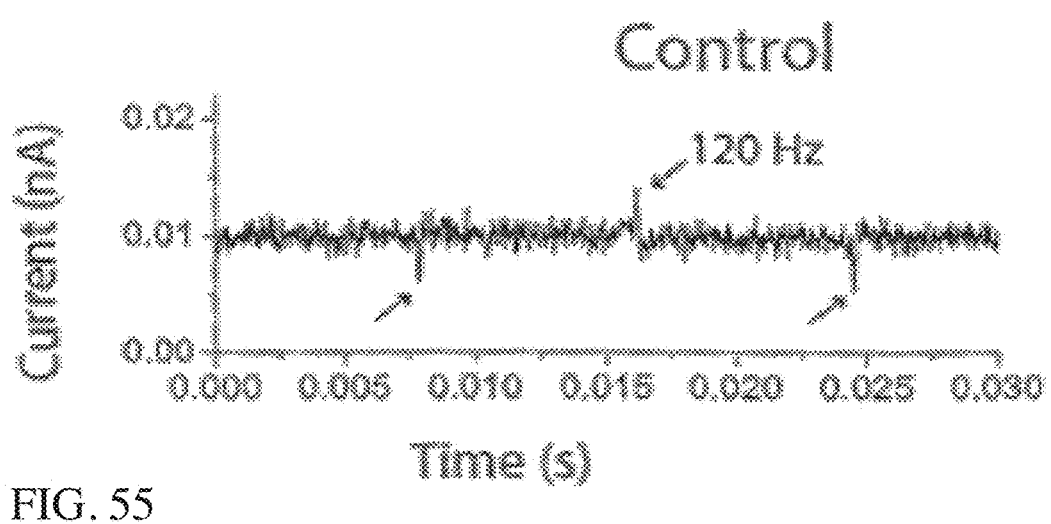

FIG. 55 shows tunneling signals for a functionalized tunnel gap in a phosphate buffered saline, but without analyte, with a 20 pS gap (i=10 pA, V=+0.5V). This example gave a signal free of features, except for some AC coupled line-noise pointed to by arrows.

FIGS. 56C-J show tunneling signals for a functionalized tunnel gap. FIGS. 56C-F show characteristic current spikes produced when nucleotides dAMP (FIG. 56C), dCMP (FIG. 56D), d$^m$CMP (FIG. 56E), and dGMP (FIG. 56F) were introduced (dTMP gave no signals in this example). FIGS. 56G-J show corresponding distribution of pulse heights for dAMP (FIG. 56G), dCMP (FIG. 56H), d$^m$CMP (FIG. 56I), and dGMP (FIG. 56J). The line curves in FIGS. 56G-J are fits to two Gaussian distributions in the logarithm of current.

Figure 57:
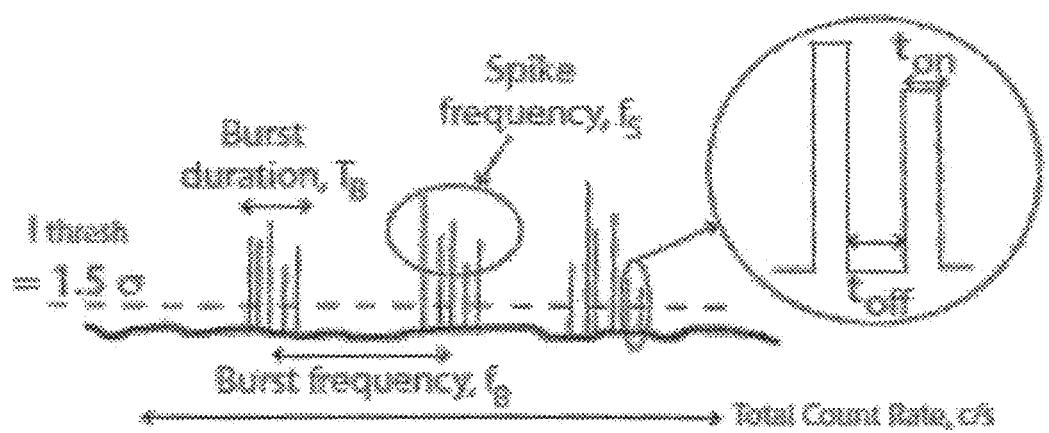

FIG. 57 illustrates parameters used to characterize the tunneling signals. Spikes are counted if they exceed a threshold equal to 1.5× the standard deviation of the noise on the local background. The signals occur in bursts (duration $T_B$, frequency $f_B$) each containing current spikes at a frequency $f_S$. The spikes stay high for a period $t_{on}$ and low for a period $t_{off}$. The total count rate (see FIGS. 56G-J) is the number of spikes in all bursts divided by the measurement time.

Figure 58A:
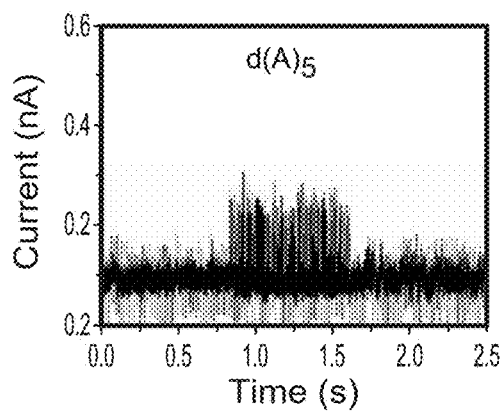
Figure 58B:
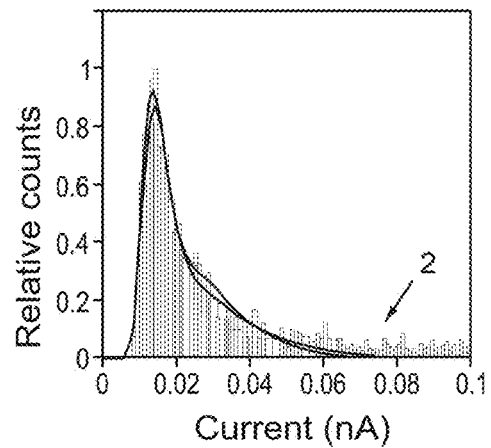
Figure 58C:
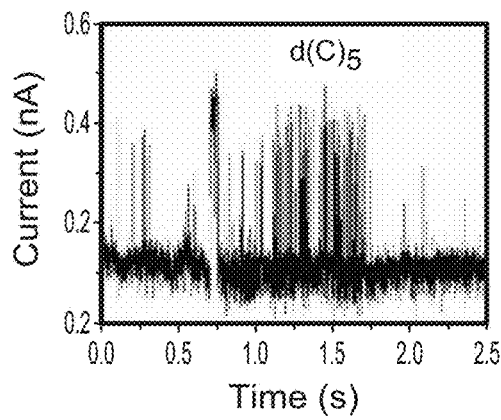
Figure 58D:
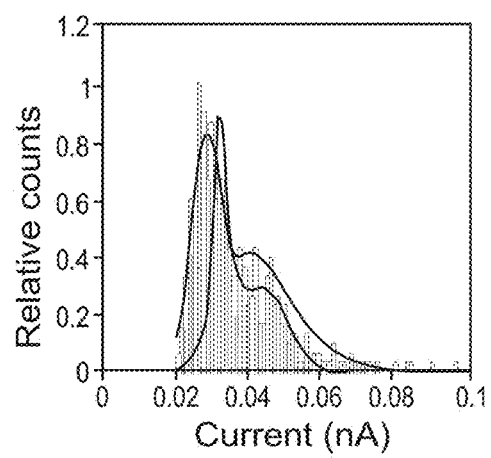
Figure 58E:
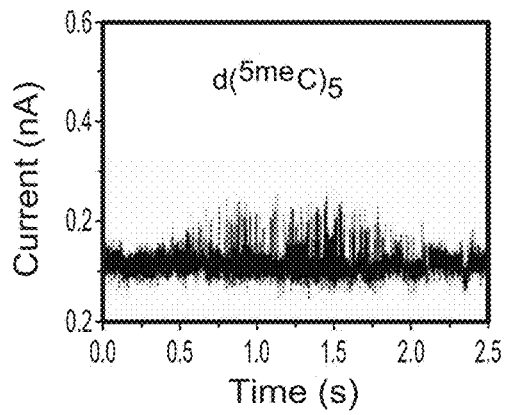
Figure 58F:
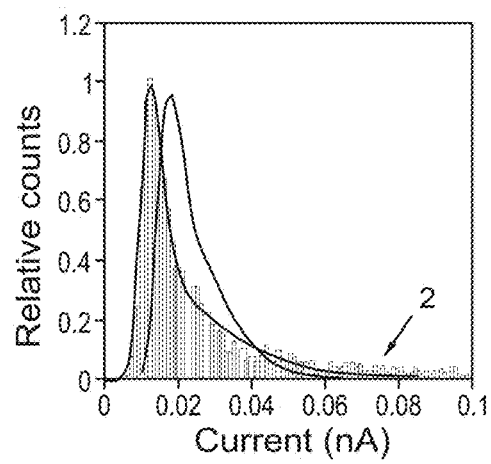
Figure 58G:
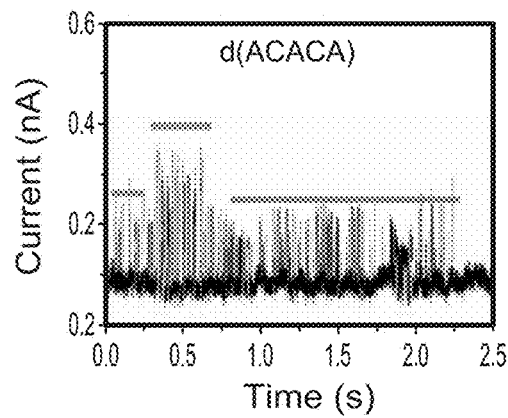
Figure 58H:
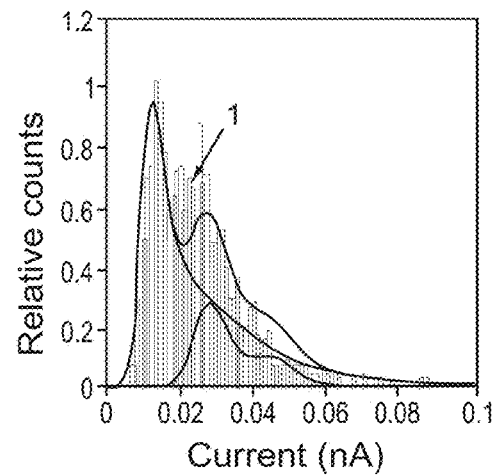
Figure 58I:
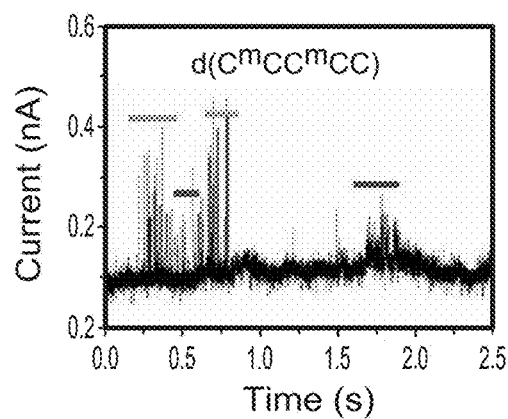
Figure 58J:
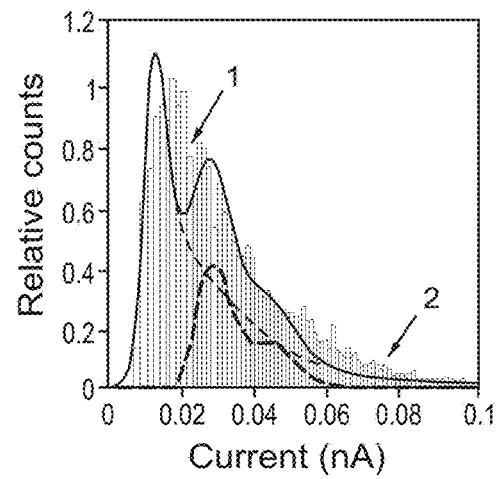

FIGS. 58A-58J illustrates how tunneling signal distributions from oligomers resemble those of the constituent nucleotides. FIGS. 58A, 58C, and 58E show representative current traces from d(A)$_5$, d(C)$_5$, and d($^m$C)$_5$ with the corresponding distributions shown in FIGS. 58B, 58D, and 58F. The line curves in FIGS. 58B, 58D, and 58F show fits for both constituent nucleotides and oligomers nucleotides. The line curves correspond closely with one another. FIG. 58G and is how current traces from mixed oligomers d(ACACA) (FIG. 58G) and d(C$^m$CC$^m$CC) (FIG. 58I) with corresponding current distributions (FIGS. 58H and 58J). The solid line curves in FIGS. 58H and 58J are scaled homopolymer fits. In FIG. 58H, the top dashed curve shows the A contribution and the bottom dashed curve shows the C contribution. In FIG. 58J, the top curve shows the me contribution and the bottom curve (beginning at 0.02 on the Current (nA) axis) shows the C contribution. The data are well described by the homopolymer parameters though some intermediate signals (labeled as "1") and new high current features (labeled as "2") show that the sequence context affects the reads slightly. The upper bar in FIG. 58G marks C-like signals, while the lower bars mark A-like signals. The upper bars in FIG. 58I mark 58C like signals and the lower bars mark $^m$C-like signals.

Figure 59A:
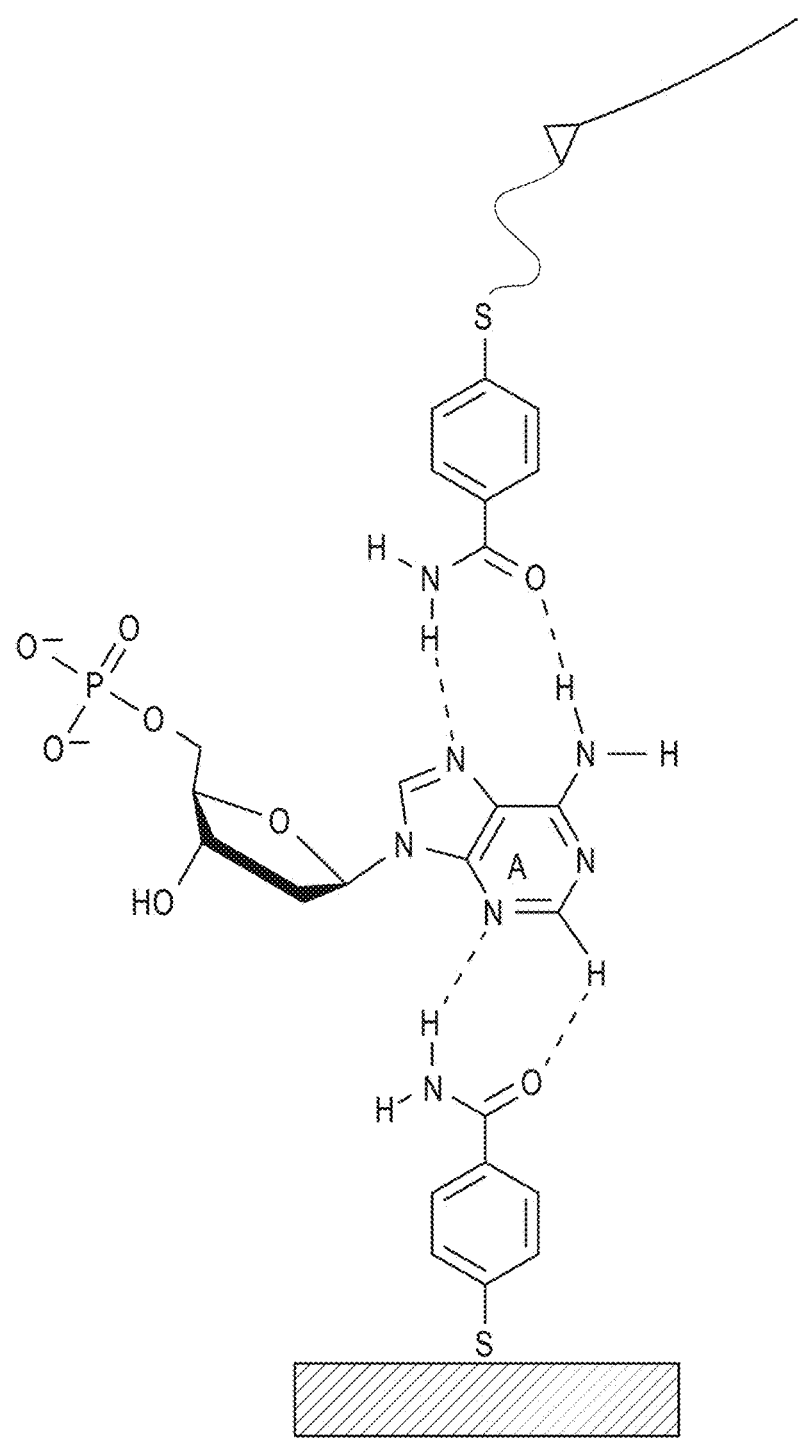
Figure 59B:
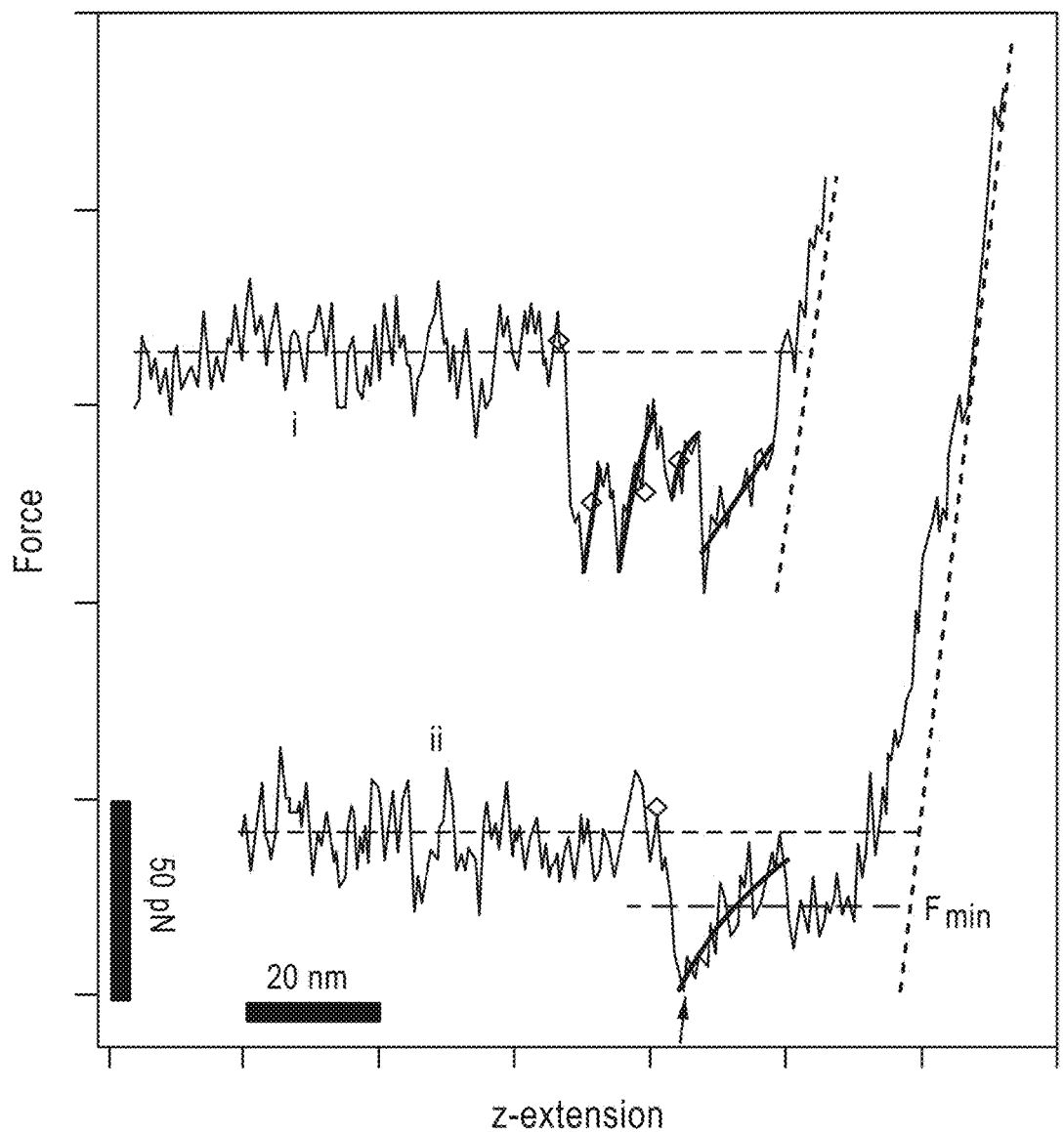
Figure 59C:
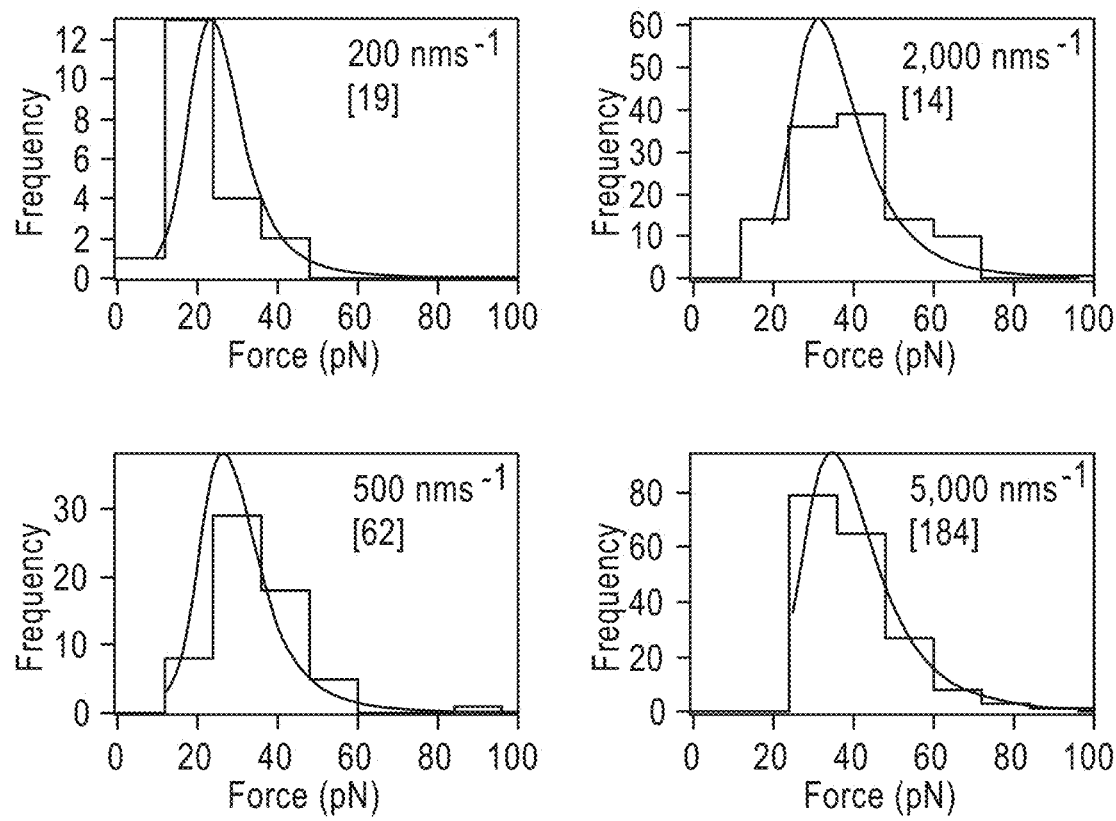
Figure 59D:
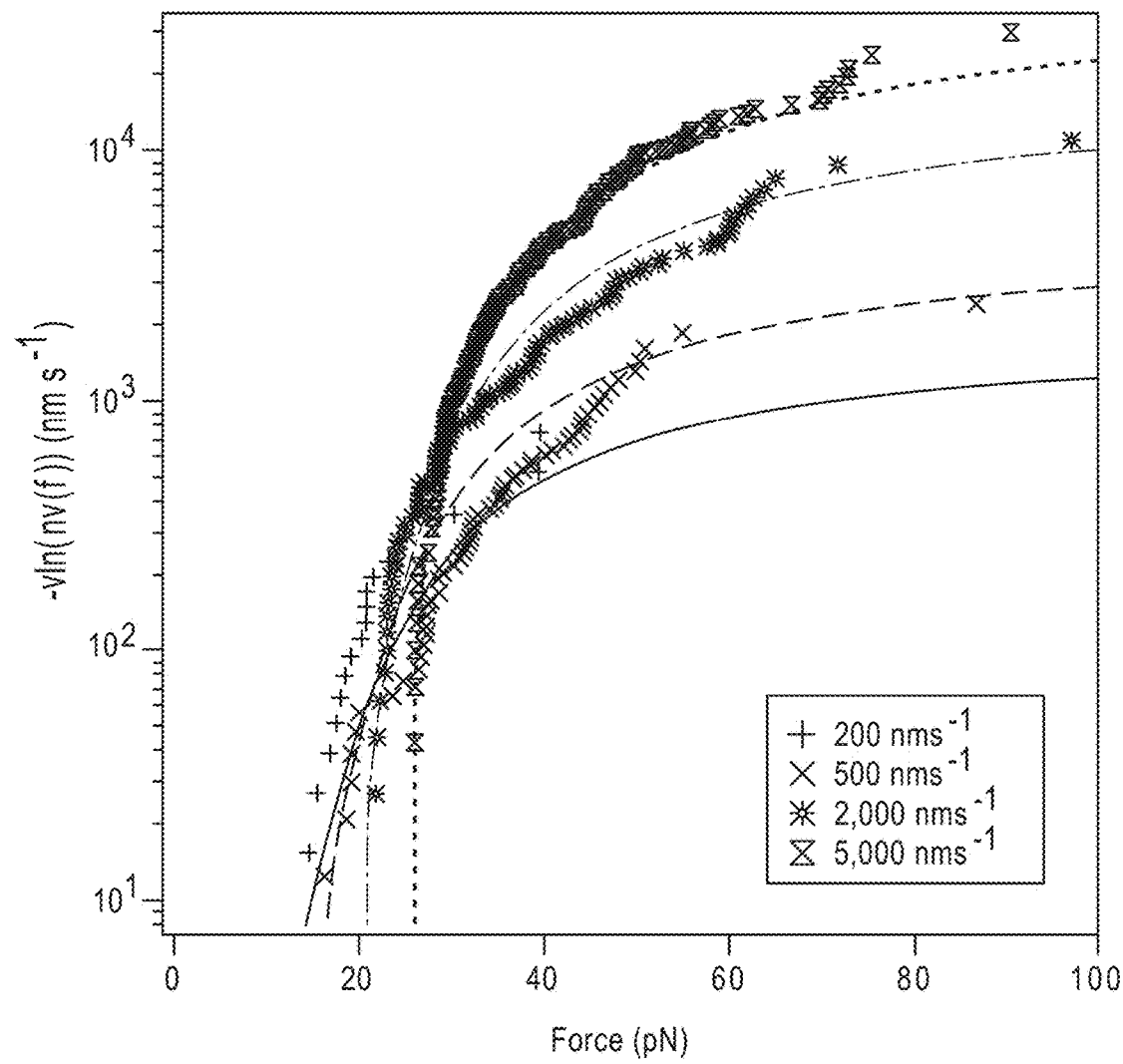

FIGS. 59A-59D shows data regarding the lifetime of the reading complex (the lifetime is on the order of a second at zero force). FIG. 59A shows AFM gap functionalization where the s-shaped line represents a 34 nm PEG linker. FIG. 59B shows representative force curves showing (i) pulling on more than one molecule at a time—the force baseline is not restored after each break and the z-extension (corrected tip displacement) is ~34 nm and (ii) a single molecule curve of the type accepted by exemplary software (as described by A. Fuhrmann, PhD Thesis in Physics, Arizona State University, 2010). The force returns to the baseline after the bond breaks and the corrected extension is ~34 nm. FIG. 59C shows histograms of bond breaking forces at the pulling speeds marked. The curves show exemplary maximum likelihood fits to the heterogeneous bond model. FIG. 59D shows bond survival probability plotted versus bond model parameters (solid lines) which are, from top to bottom 5000 nm/s, 2000 nm/s, 500 nm/s, and 200 nm/s. These fits yield a zero-force off rate of 0.28 s$^{-1}$ implying that the assembly lives for times on the order of seconds in a nanogap, much longer than the lifetime in solution (see FIG. 47 for details of solution binding measurements).

Figure 60:
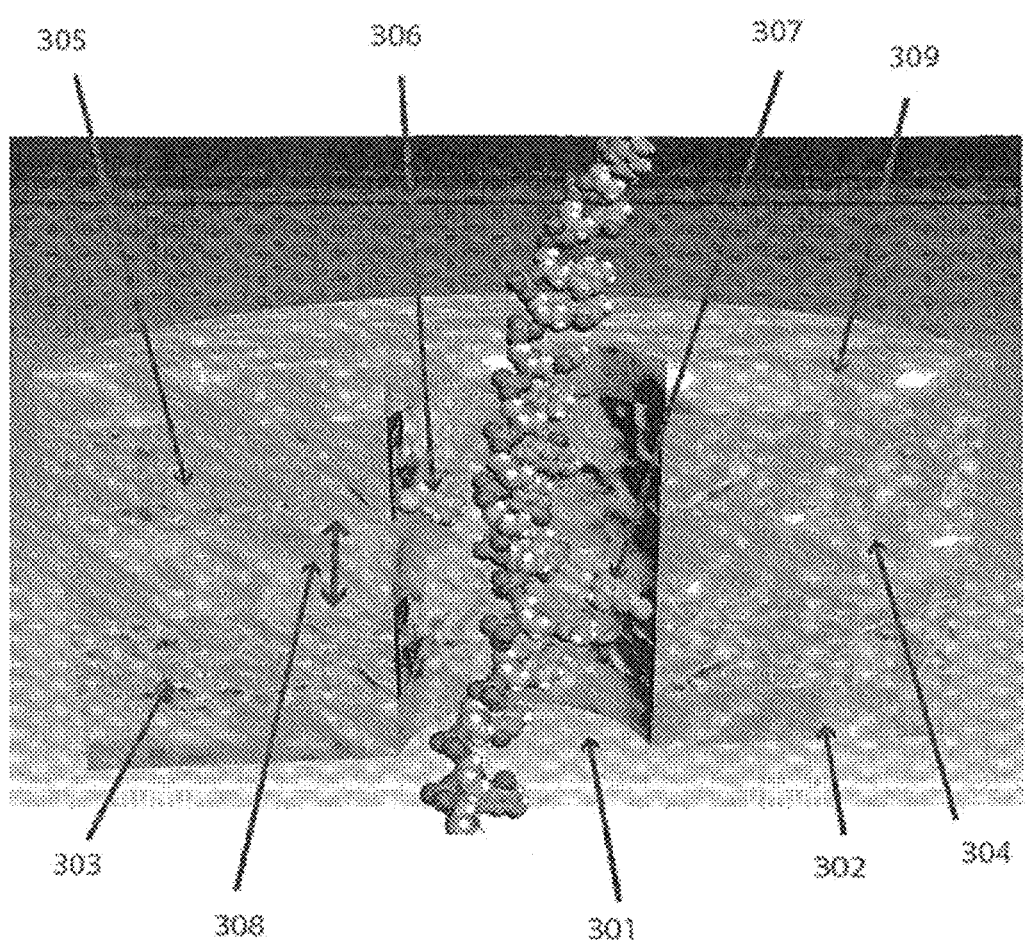

FIG. 60 illustrates a chip according to an embodiment of the invention. In the chip, a pair of reading electrodes are formed by atomic layer deposition of conductors, such as TiN separated by a thin (for example, 2 nm) dielectric layer with nanopores drilled through the chip. Recognition molecules (reagents) are covalently tethered to the metal electrodes and form a self-assembled junction on each base (or residue) in turn via non-covalent interactions as electrophoresis drives the molecule through the gap.

Figure 61:
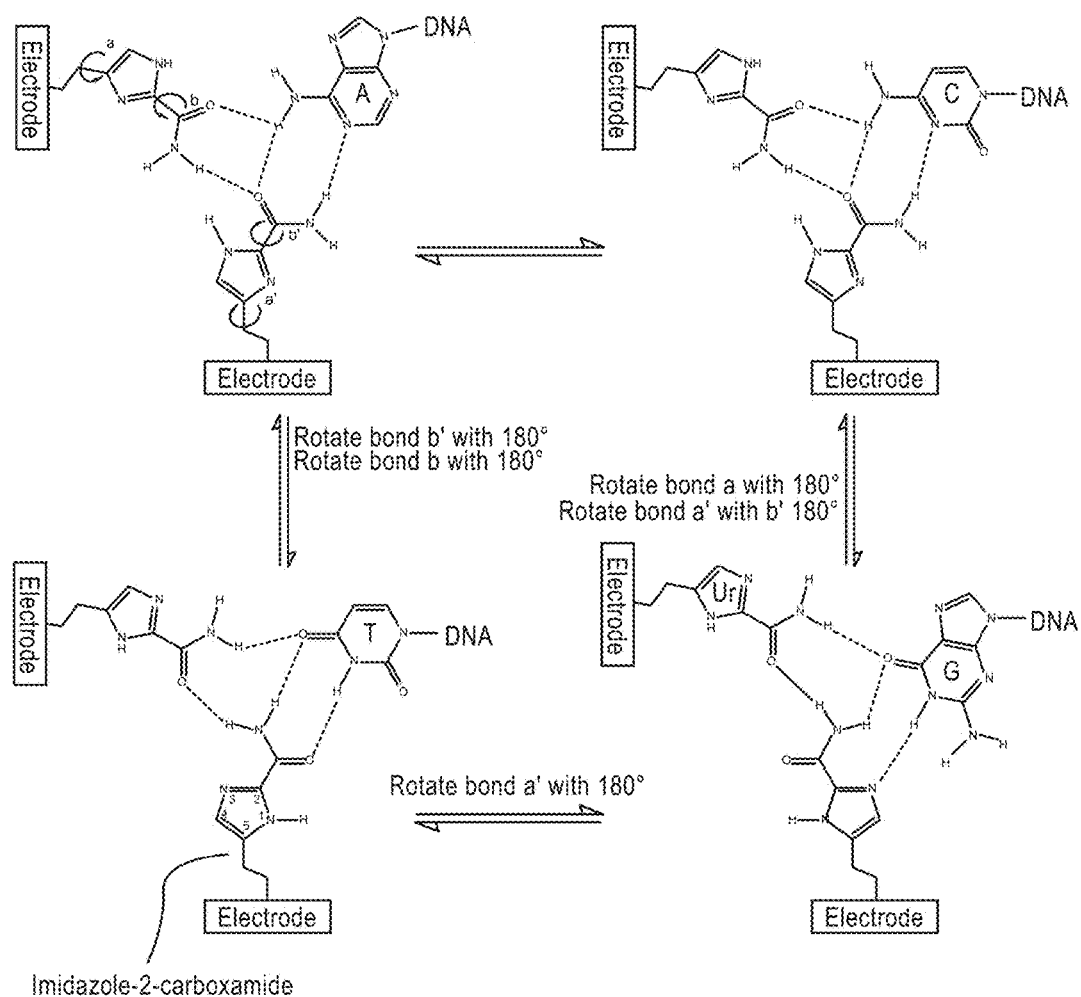

FIG. 61 shows exemplary hydrogen bonding modes of imidazole-2-carboxyamide for adenine, thymine, cytosine, and guanine.

Figure 62A:
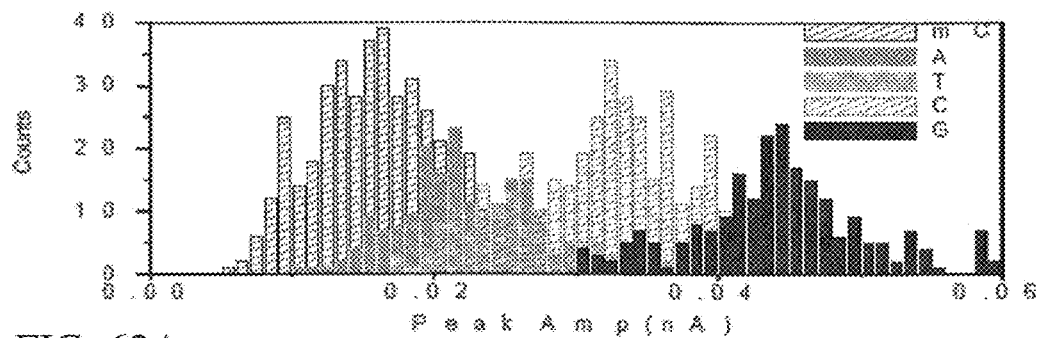
Figure 62B:
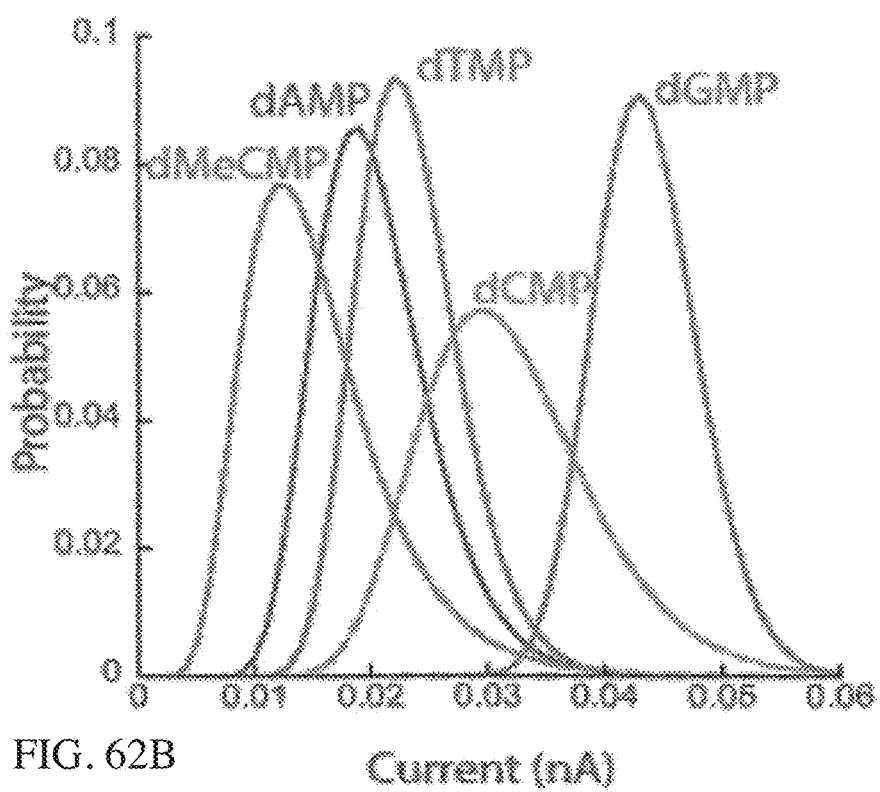

FIGS. 62A and 62B show exemplary current distributions measured with deoxy-nucleotides in a fixed gap comprised of imidazole-2-carboxyamide functionalized electrodes (FIG. 62A—peak amplitude vs. counts; FIG. 62B—probability vs. current).

Figure 63:
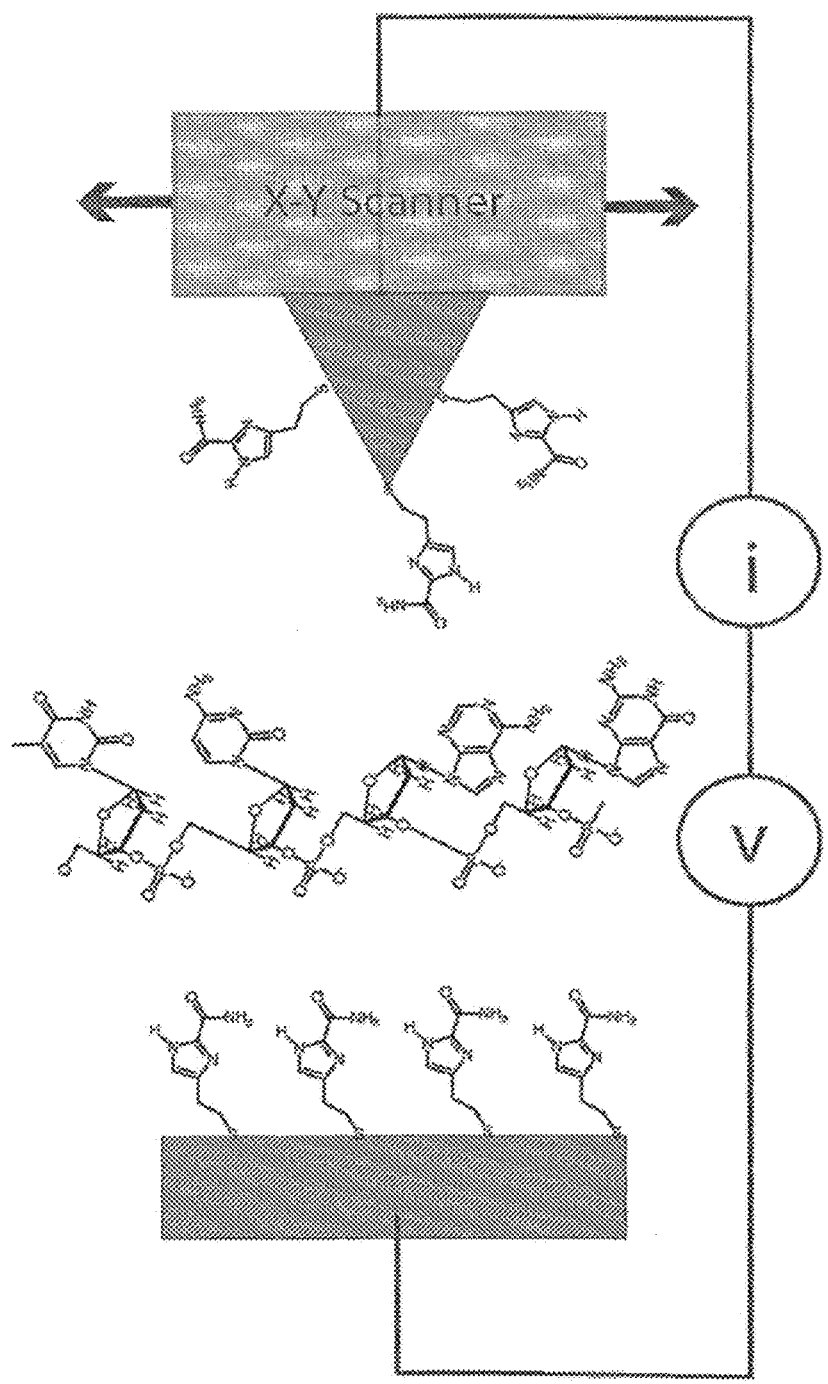

FIG. 63 shows an exemplary device with imidazole-2-carboxyamide functionalized electrodes and a probe that may be translated across a surface at a constant gap.

Figure 64A:
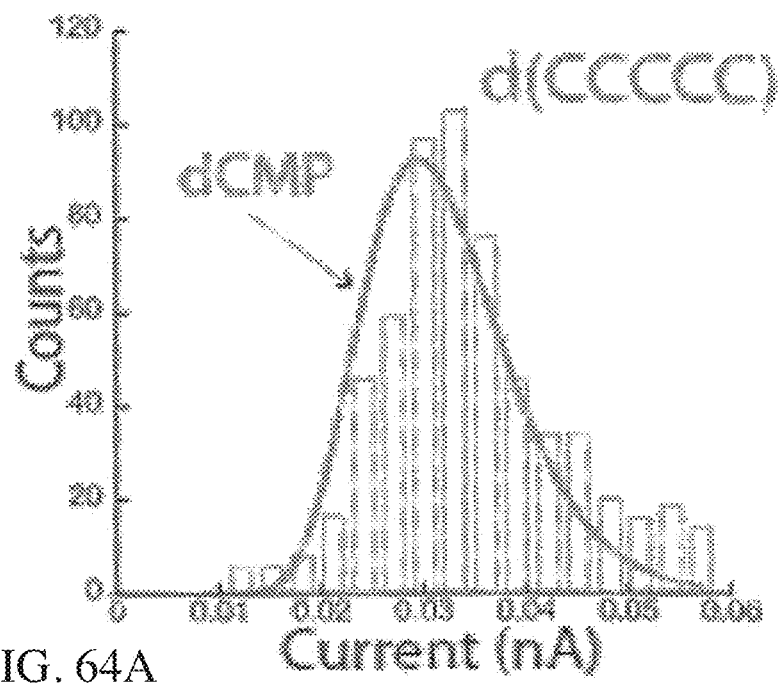
Figure 64B:
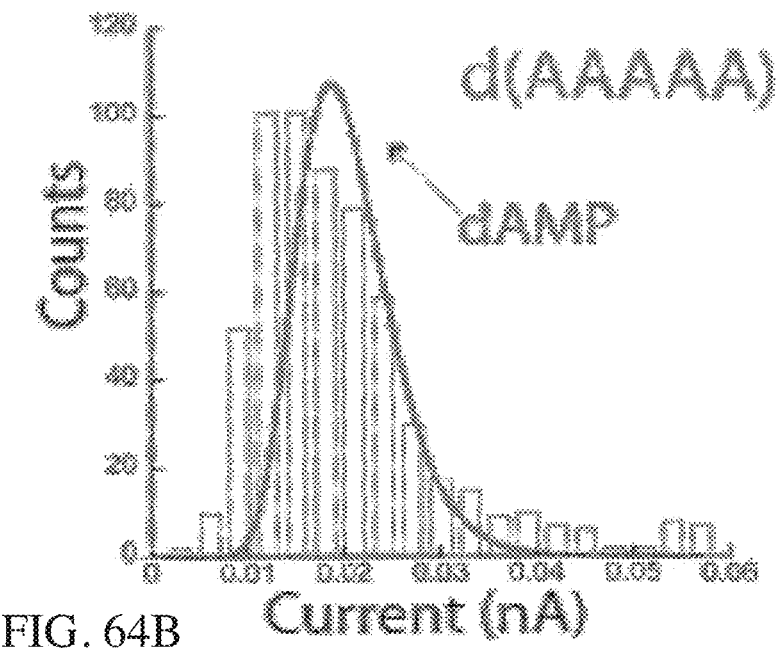

FIGS. 64A, 64B show that the DNA reads fit nucleotide current distributions for $dC_5$ (FIG. 64A) and for dA5 (FIG. 64B).

Figure 65:
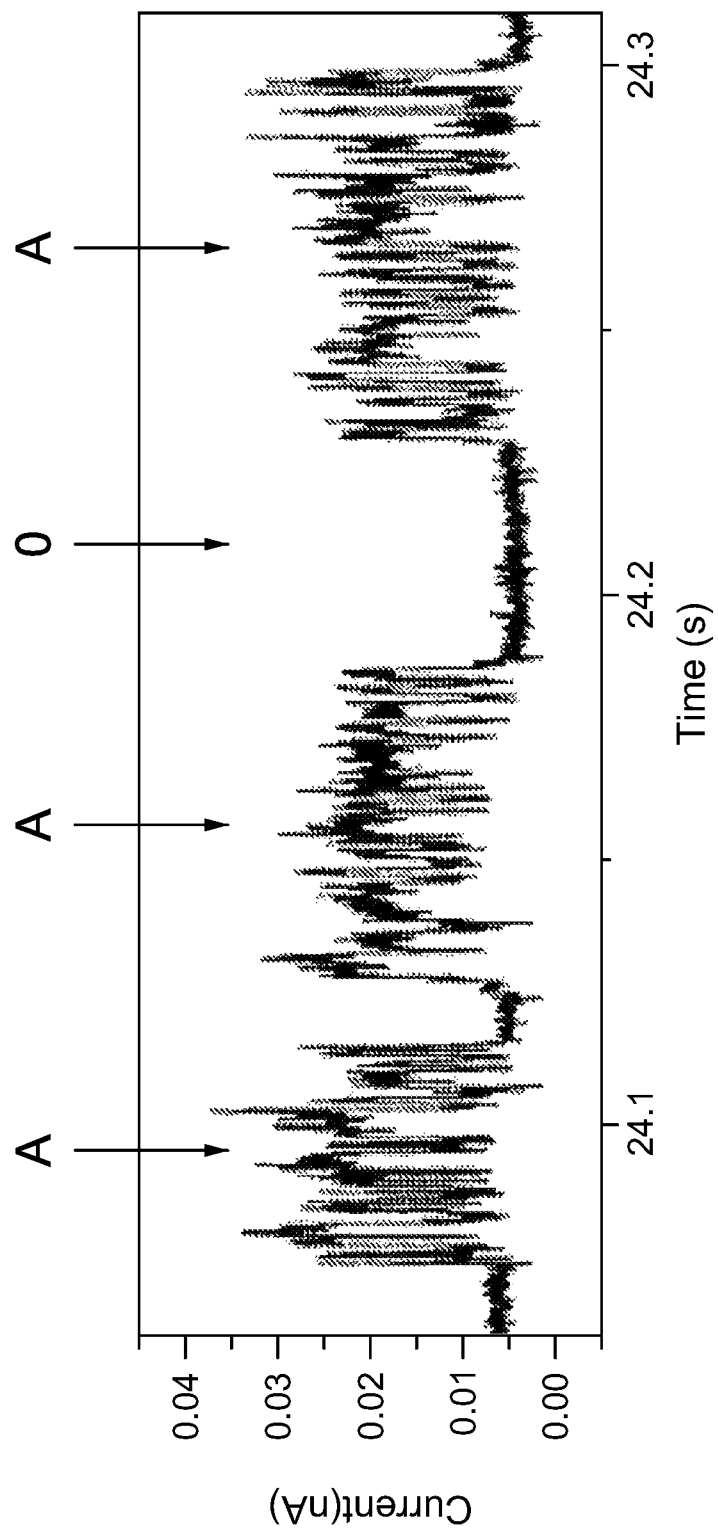

FIG. 65 shows exemplary current reads for an AAAAA oligomer for a fixed gap.

Figure 66:
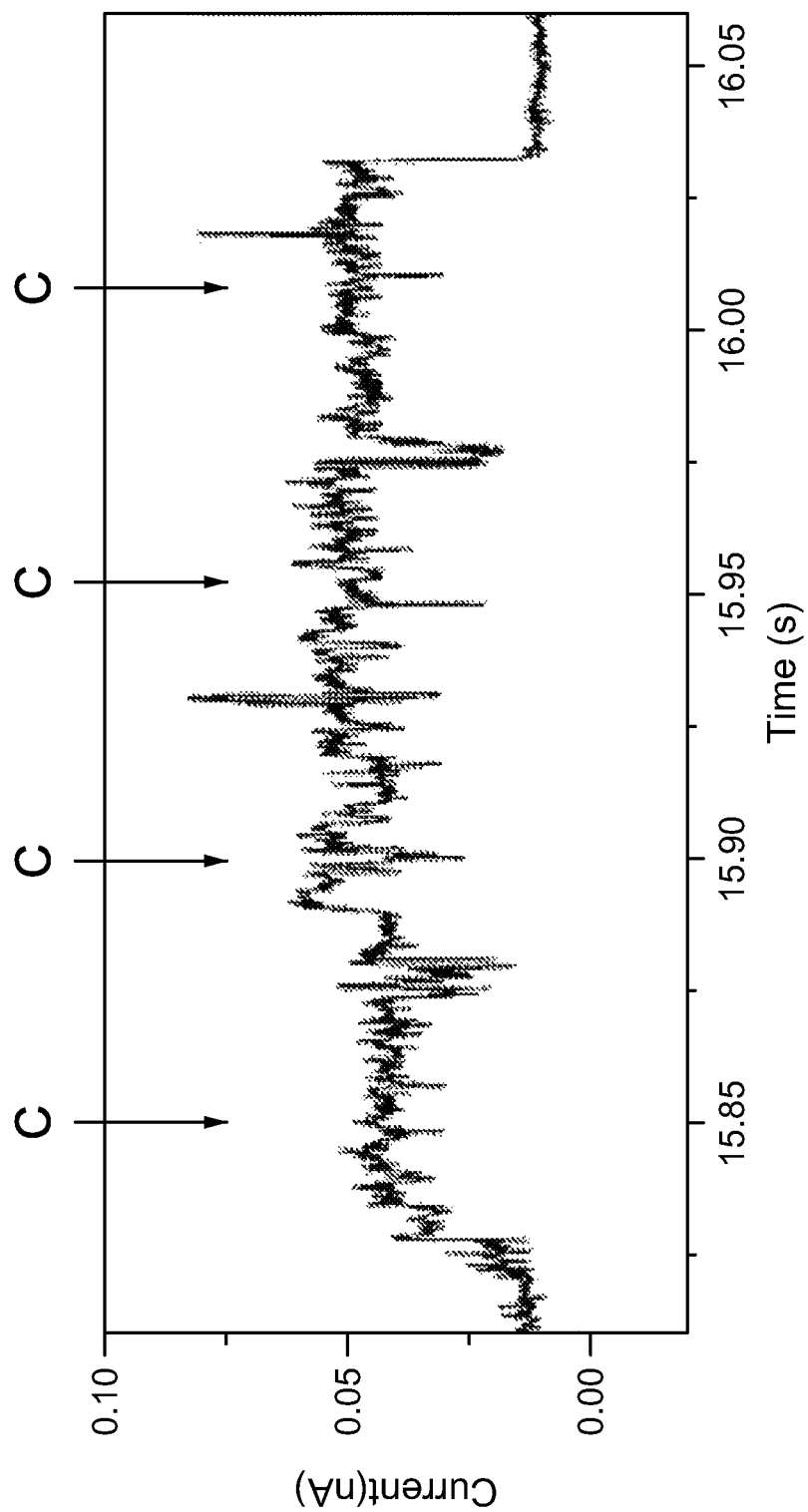

FIG. 66 shows exemplary current reads for a CCCCC oligomer for a fixed gap.

Figure 67:
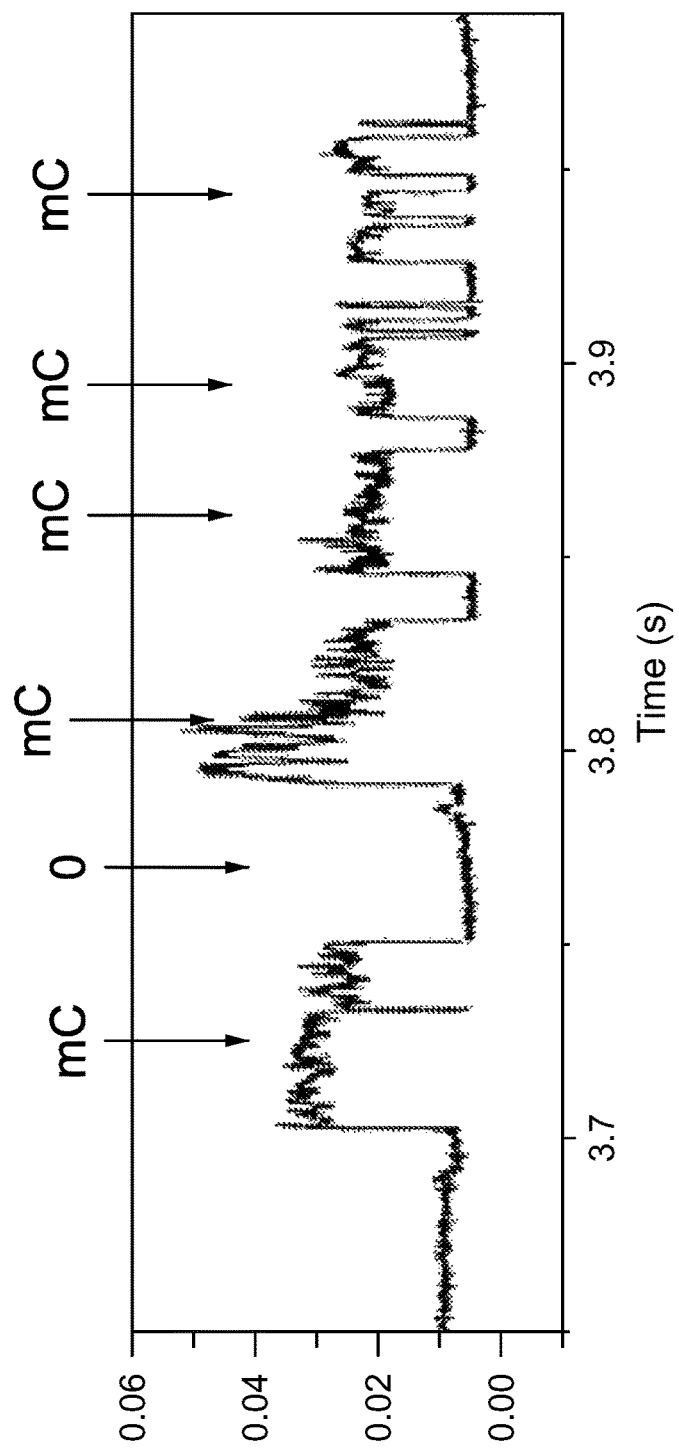

FIG. 67 shows exemplary current reads for a $d(^mC)_5$ oligomer for a fixed gap.

Figure 68:
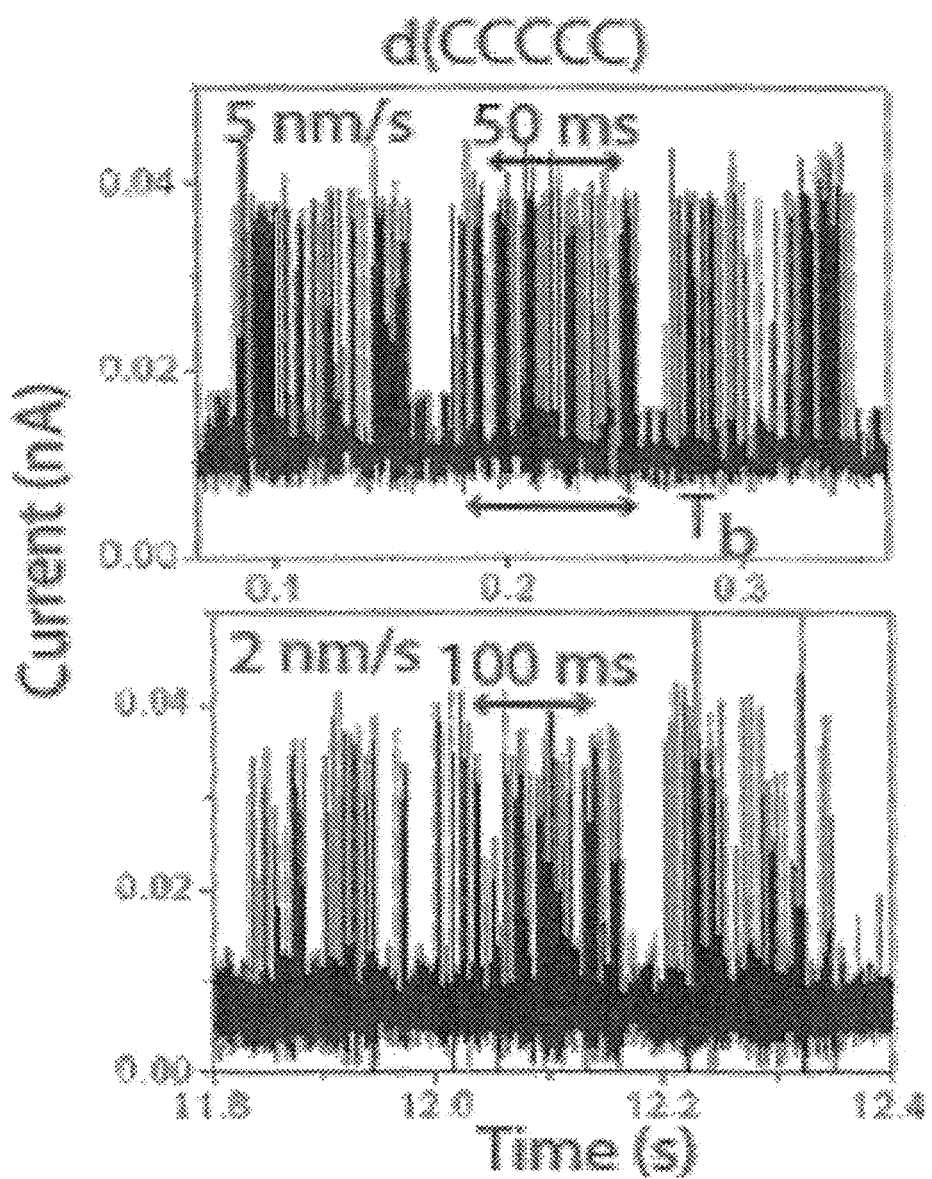

FIG. 68 shows exemplary current reads for a d(CCCCC) oligomer for a variable gap held at an approximately constant value by servo control of the tunnel current.

Figure 69:
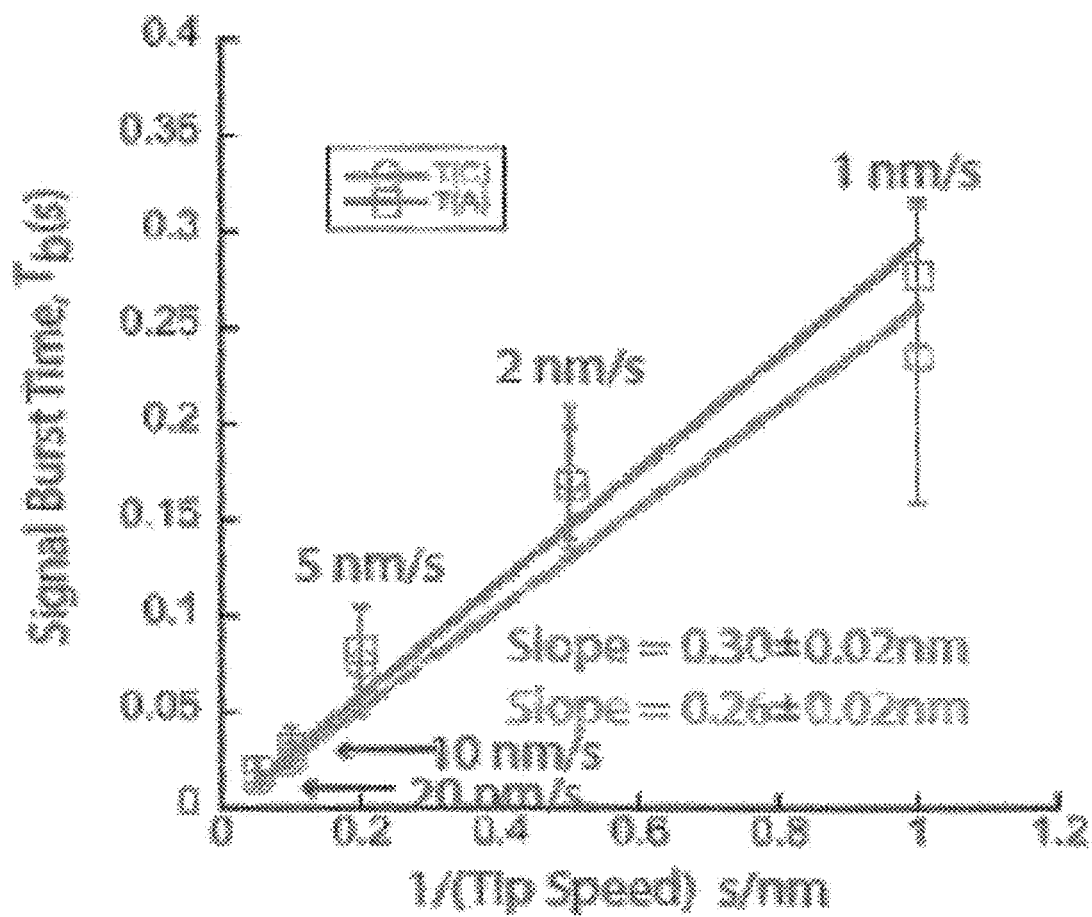

FIG. 69 shows an exemplary plot of signal burst time vs. reciprocal scan speed for $dA_5$ (top slope) and $dC_5$ (bottom slope) with a slope of approximately 0.3 nm.

Figure 70:
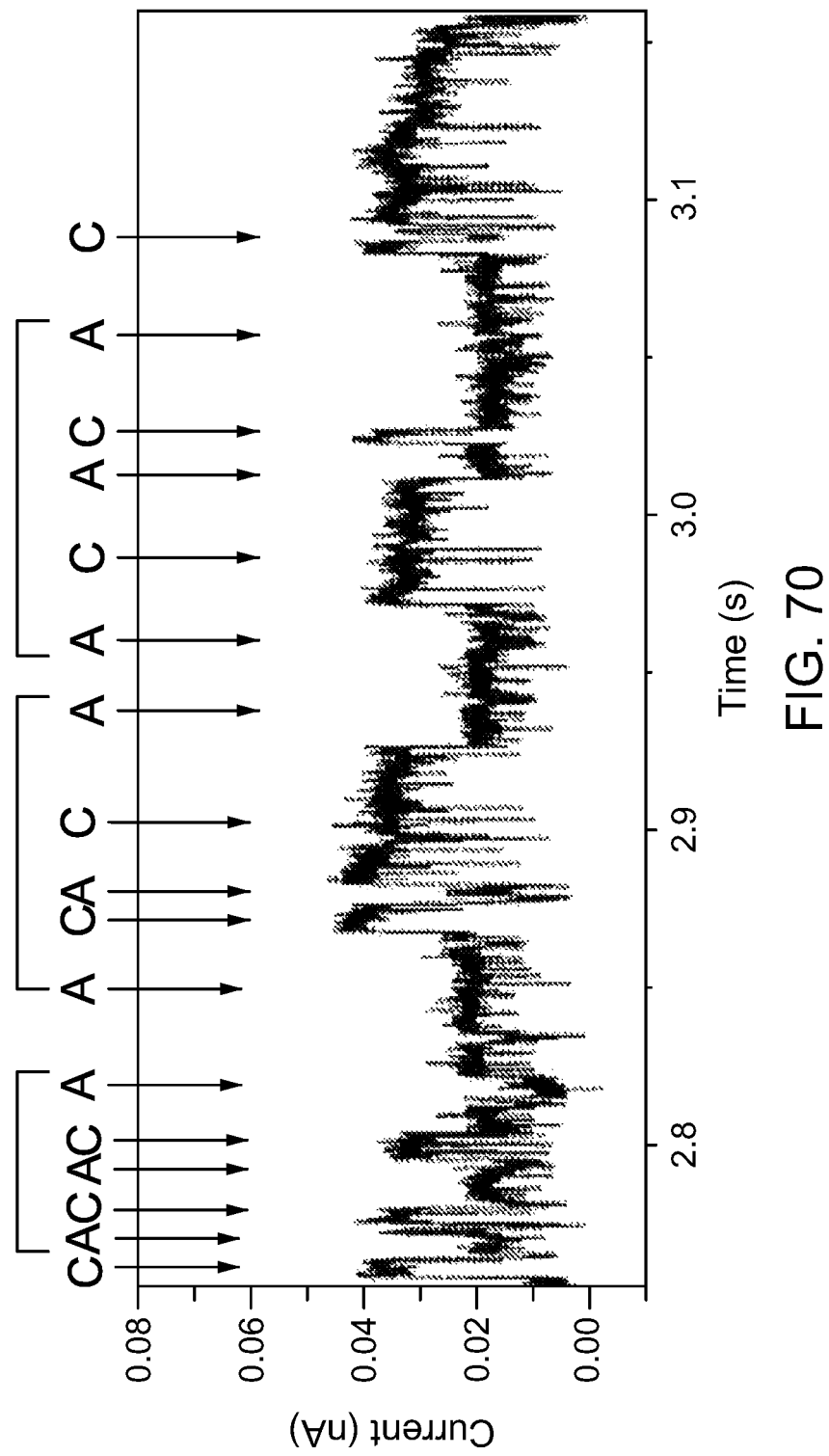

FIG. 70 shows exemplary current reads for an ACACA oligomer for a fixed gap.

Figure 71:
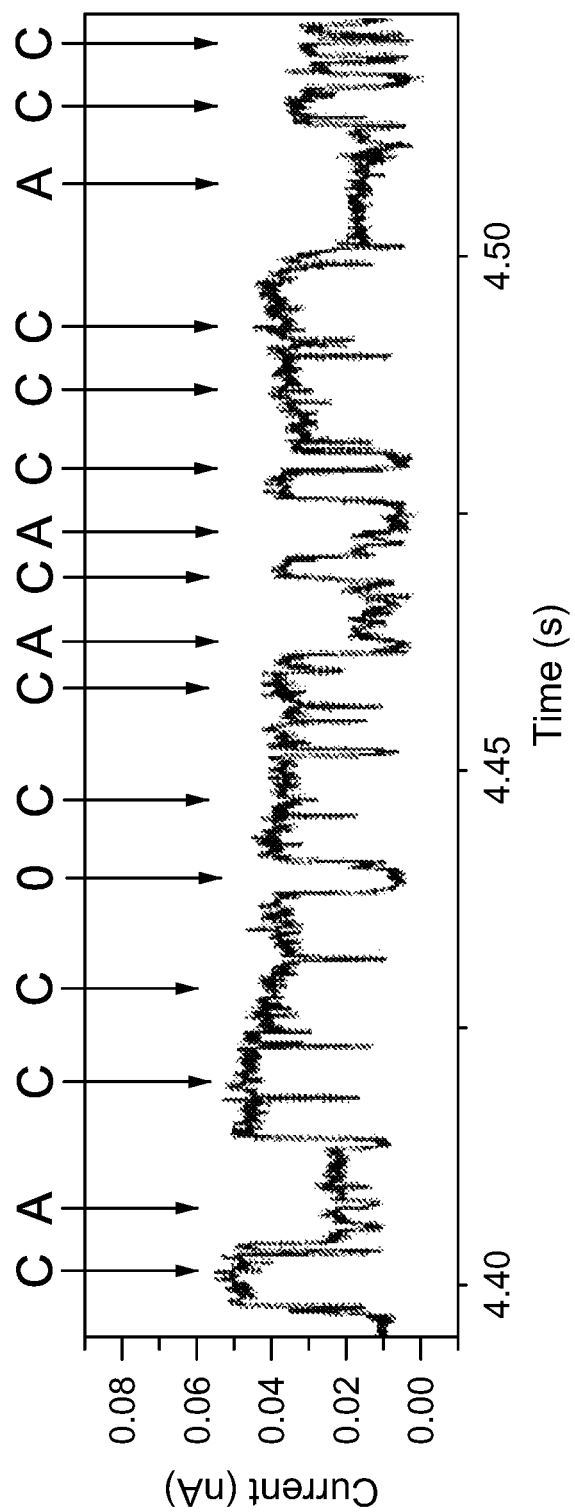

FIG. 71 shows exemplary current reads for an CCACC oligomer for a fixed gap.

Figure 72:
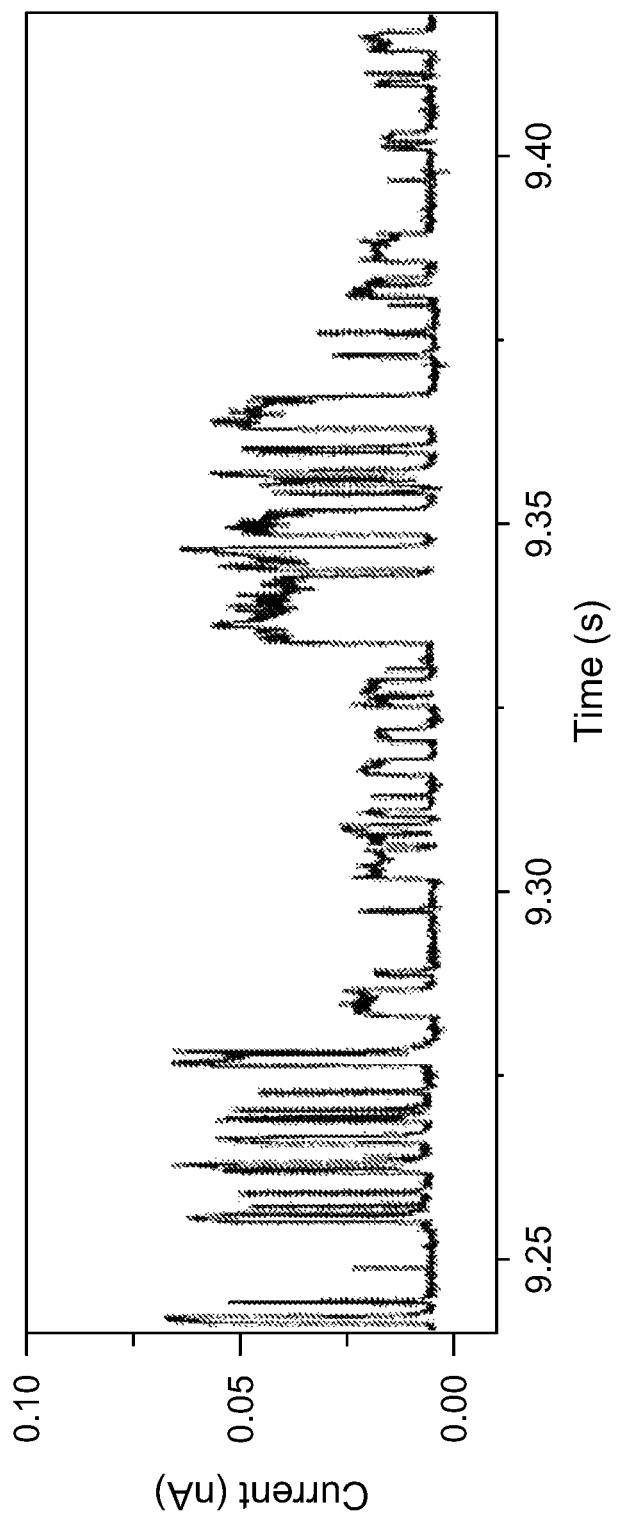

FIG. 72 shows exemplary current reads for an $C^mCC^mCC$ oligomer for a fixed gap.

Figure 73:
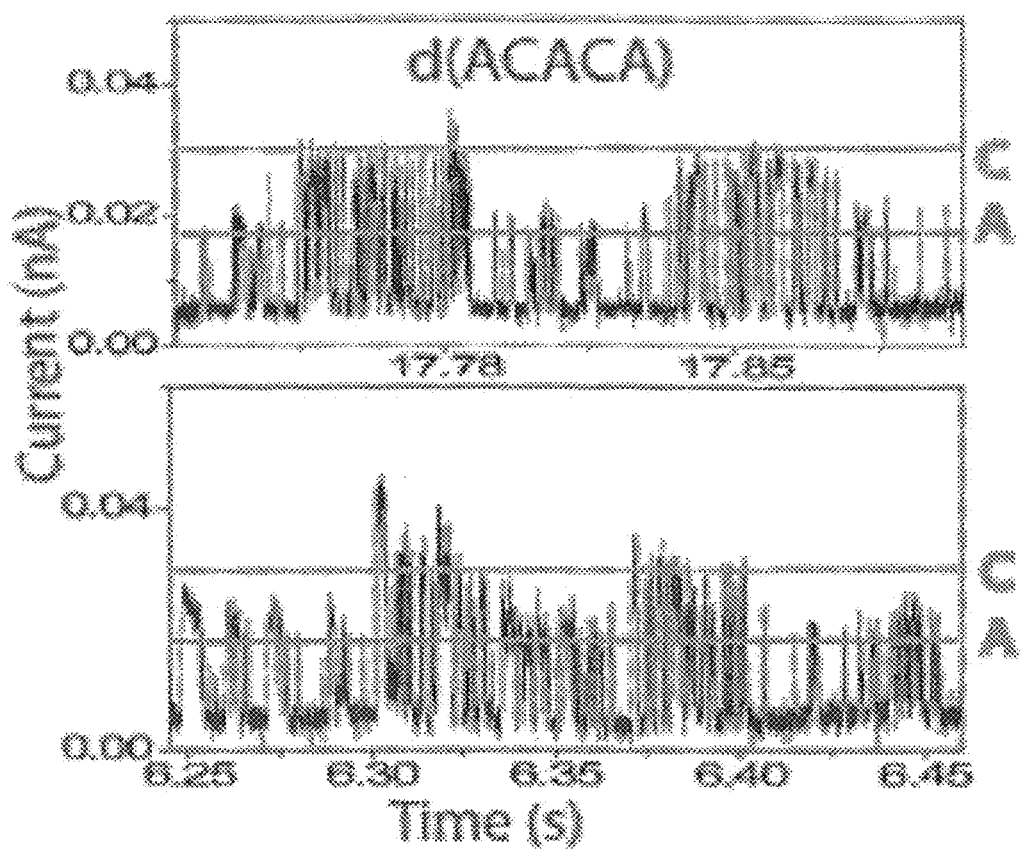

FIG. 73 shows exemplary current reads for an ACACA oligomer for a variable gap held at an approximately constant value by servo control of the tunnel current.

Figure 74:
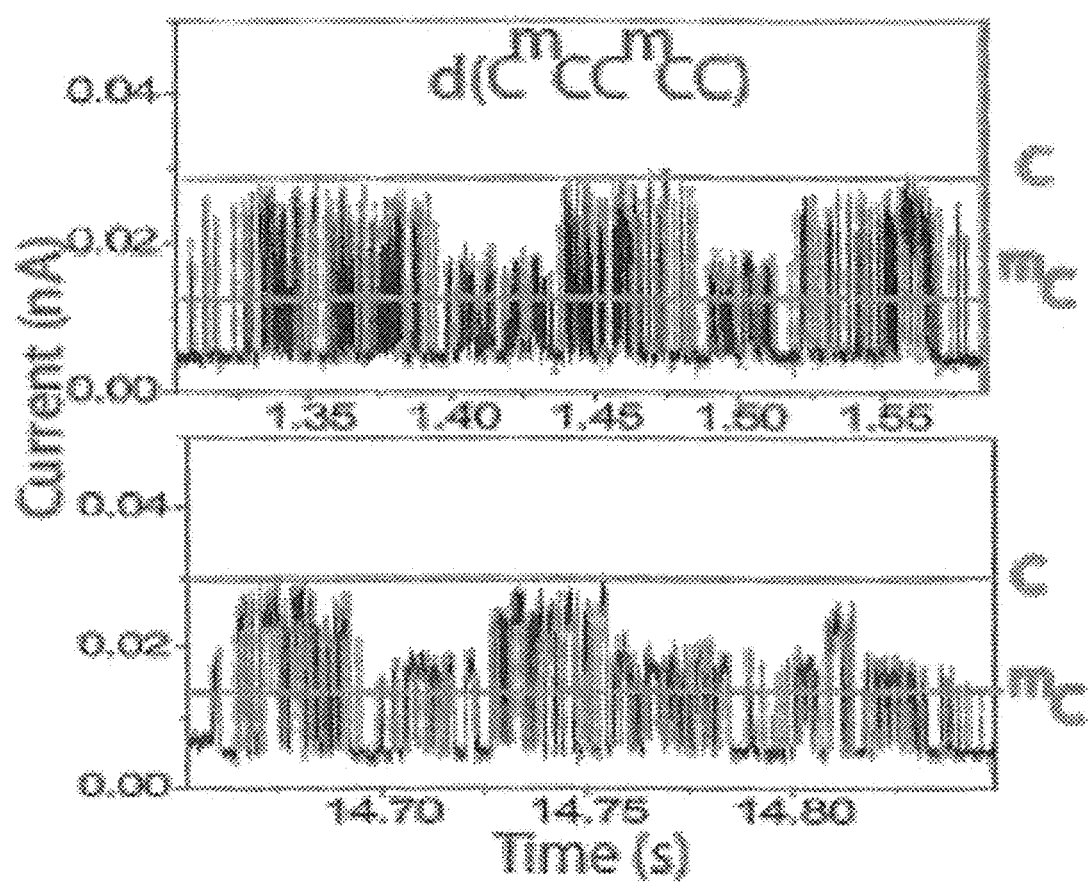

FIG. 74 shows exemplary current reads for an $C^mCC^mCC$ oligomer for a variable gap held at an approximately constant value by servo control of the tunnel current.

Figure 75:
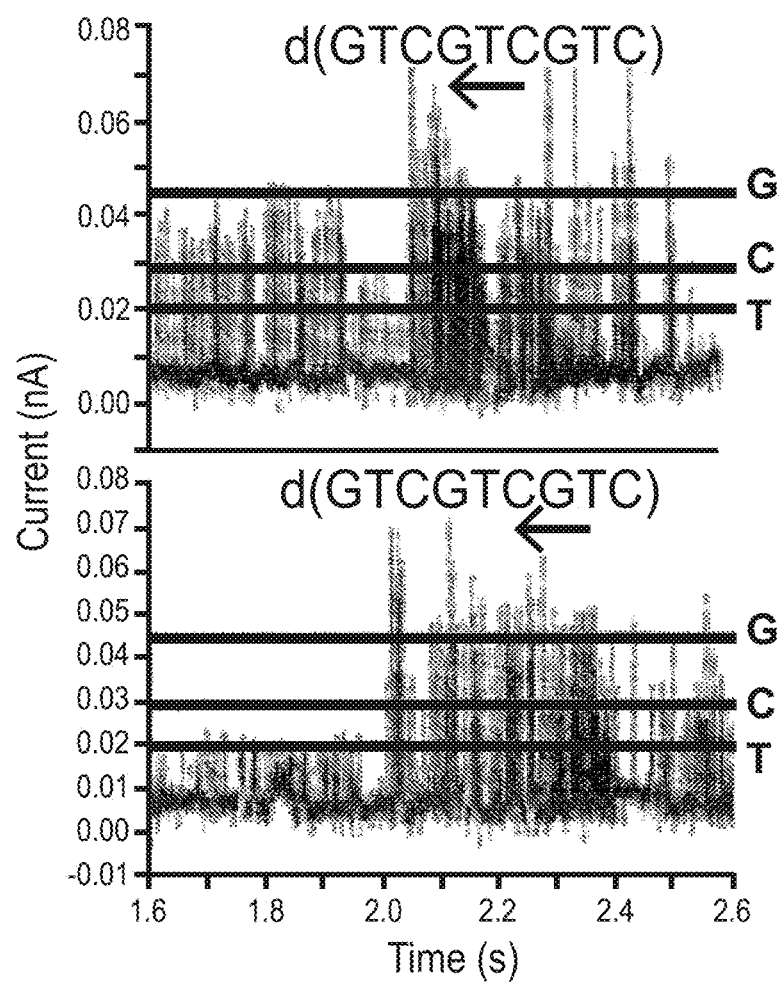

FIG. 75 shows exemplary current reads for an GTCGTCGTC oligomer for a variable gap held at an approximately constant value by servo control of the tunnel current.

Figure 76:
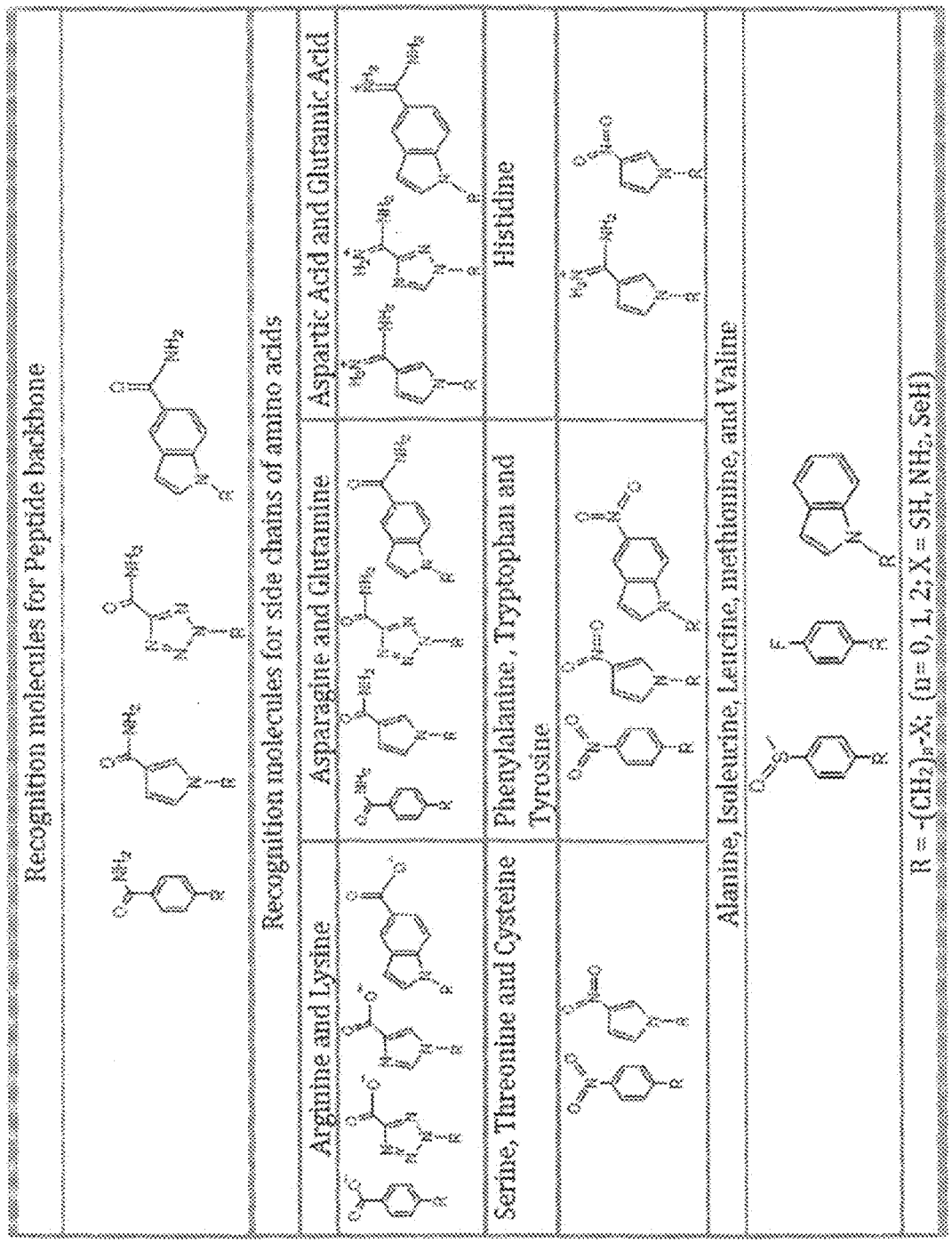

FIG. 76 shows exemplary recognition molecules (reagents) for amino acids and the peptide backbone.

DETAILED DESCRIPTION OF THE INVENTION

The present invention provides compositions, components, devices, and methods for analyzing polymer units and/or polymers. Exemplary polymer units and polymers that may be analyzed include heteropolymers and associated units. For example, polymers that may be analyzed include DNA, RNA, polysaccharides, and peptides; and polymer units include polymer monomers, nucleotides, nucleosides, amino acids, polysaccharides monomers. In some embodiments, epigenetic marks, such as methylated DNA and/or RNA, may be analyzed and distinguished from, for example, non-methylated DNA/RNA units.

The devices include two or more electrodes functionalized with one or more reader molecules (also referred to as reagents) and a tunnel gap through which the polymer units and/or polymer may pass. The reagents on the electrodes are capable of forming a transient bond to the units of the polymer. A transient chemical or physical bond forms when the unit is in the gap and completes the circuit between the first and second electrodes. The formed transient bond may then elicit a detectable signal that is used to analyze the polymer.

Electrodes

The two or more electrodes may be made of any suitable material that can be functionalized with a reagent capable of binding the target polymer unit(s). For example, the electrodes may be made of any conductive material, such as a metal, a metal alloy, gold, platinum, a gold alloy, a platinum alloy, carbon, carbon nanotubes, graphene, or titanium nitride. In some embodiments, the electrodes comprise a probe and a substrate. The electrodes may be formed on or in between or be partially insulated with any suitable inorganic or organic insulating material, such as inorganic materials including $Si_xO_{-1x}$, silicon nitride, metal oxides, or organic materials, including polymers such as polyethylene, polystyrene, polymethylmethacrylate and others as are well known in the art. The insulating material may be configured to prevent background noise from the electrode when a current is flowing. For example, an electrode may be completely covered with HOPE except for a small tip or apex. In another embodiment, the electrode may be embedded between insulating layers with only regions in contact with the nanopore exposed (FIG. 60). As much as a square micron can be exposed to salt solutions of up to one molar with negligible leakage currents for biases of half a volt or less.

The reading reagents play an important role in "sharpening" the electrodes. The typical gold electrode has a nanocrystalline composition in which facets of 10 nm or more in size are exposed. Thus it would appear to be impossible to contact just a single base. However, single bases are readily resolved when the electrodes are functionalized. This is because specific molecular contacts now serve as the tunneling electrodes, forming sharp, well defined asperities on the metal surface.

Reagents

The electrodes are functionalized by one or more reagents. The electrodes may be functionalized with the same reagent, a combination of reagents, or individually functionalized with separate reagents. Any suitable reagent capable of binding to the electrode and transiently binding to the target polymer unit may be used.

To facilitate binding of the target polymer unit to the electrode, a variety of functional groups may be tethered to a reader molecule capable of binding to the target polymer units, depending on the electrode substance desired. Suitable functional groups may include, for example, —SH, —NH$_2$, —N$_3$, —NHNH$_2$, —ONH$_2$, —COOH, —CHO, acetylene, dithiocarbamate, and dithiocarboxylate. Dithiocarbamate linkage to a metal greatly increases the tunnel current by aligning molecular levels more closely with the metallic Fermi level (see Florian von Wrochem, Deqing Gao, Frank Scholz, Heinz-Georg Nothofer, Gabriele Nelles and Jurina M. Wessels, "Efficient electronic coupling and improved stability with dithiocarbamate-based molecular junctions", Nature Nanotechnology, Jun. 20, 2010.) In some embodiments, the electrode is tethered to a functional group which can then bind to the reader molecule. For example, with metals, when the electrode is gold, a reagent with a thiol functional group may be used to facilitate a covalent bond between the reagent and the electrode. Dithiocarbamates may be used to bind to gold, Pt, and TiN. These groups can provide enhanced electronic coupling between the metal and the reagent. Amine chemistry may be used to functionalize graphene pores and carbon nanotubes ends since graphene edges frequently have carboxylates, carbonyls, and epoxides.

The reagents are capable of forming a transient bond with the target polymer unit (J. He et al., *Nanotechnology* 20, 075102 (2009)) and the nucleosides (S. Chang et al., *Nature Nanotechnology* 4, 297 (2009)). The transient bond may be a physical, chemical, or ionic bond so long as the bond permits a detectable electronic signal to be detected via the electrodes (S. Chang et al., Nanotechnology 20, 075102 (2009); M. H. Lee, O. F. Sankey, *Phys. Rev.* E 79, 051911 1 (2009)). A preferred transient bond includes a hydrogen bond. As such, exemplary reagents may include hydrogen donating or accepting groups. Another embodiment is the pi-stacking interaction between aromatic rings that are pushed together in water or aqueous electrolytes.

Exemplary reagents for binding DNA and/or RNA include mercaptobenzoic acid, 4-mercaptobenzamide, imidazole-2-carboxide, and dithiocarbamateimidazole-2-carboxide (also referred to as 4-carbamonylphenyldithiocarbamate). 4-mercaptobenzamide presents two hydrogen-bond donor sites (on the nitrogen) and one hydrogen-bond acceptor site (the carbonyl). Likely binding modes to, for example, the four nucleotide bases are shown in FIG. 53. Likely binding modes of imidazole-2-carboxyamide to the four nucleotide bases are shown in FIG. 61. Additional bonding modes that involve pi-stacking between the aromatic rings in the readers and DNA bases are also likely. The reagents may be formulated to present one or more hydrogen bond donors and/or one or more hydrogen bond acceptors when in various solvents, such as organic solvent, water, or an aqueous electrolyte solution. For example, mercaptobenzoic acid works in organic solvent, such as trichlorobenzene, while 4-mercatobenzamide, imidazole-2-carboxide, and dithiocarbamateimidazole-2-carboxide work in aqueous electrolytes and water. It should be noted that many molecules that embody these design principles will function as readers. For example, guanine, functionalized with a thiol to anchor it to gold or TiN electrodes, will generate recognition signals.

In some embodiments, the reagents may be configured to include a flexible moiety that forms a bridge between the electrode and hydrogen bonding moiety of the reagent. This bridge may be a substituted or unsubstituted alkyl chain, such as —$(CH_2)_y$—, where y is an integer of 1 to 5. For example, when functionalized to the electrode, imidazole-2-carboxyamide has a —$CH_2CH_2$— bridge connecting the amide portion to the electrode. This bridge permits the amide portion to rotate and, thereby, interact in different and detectable ways with adenine, cytosine, guanine, and thymine. See FIG. 61.

Figure 13:
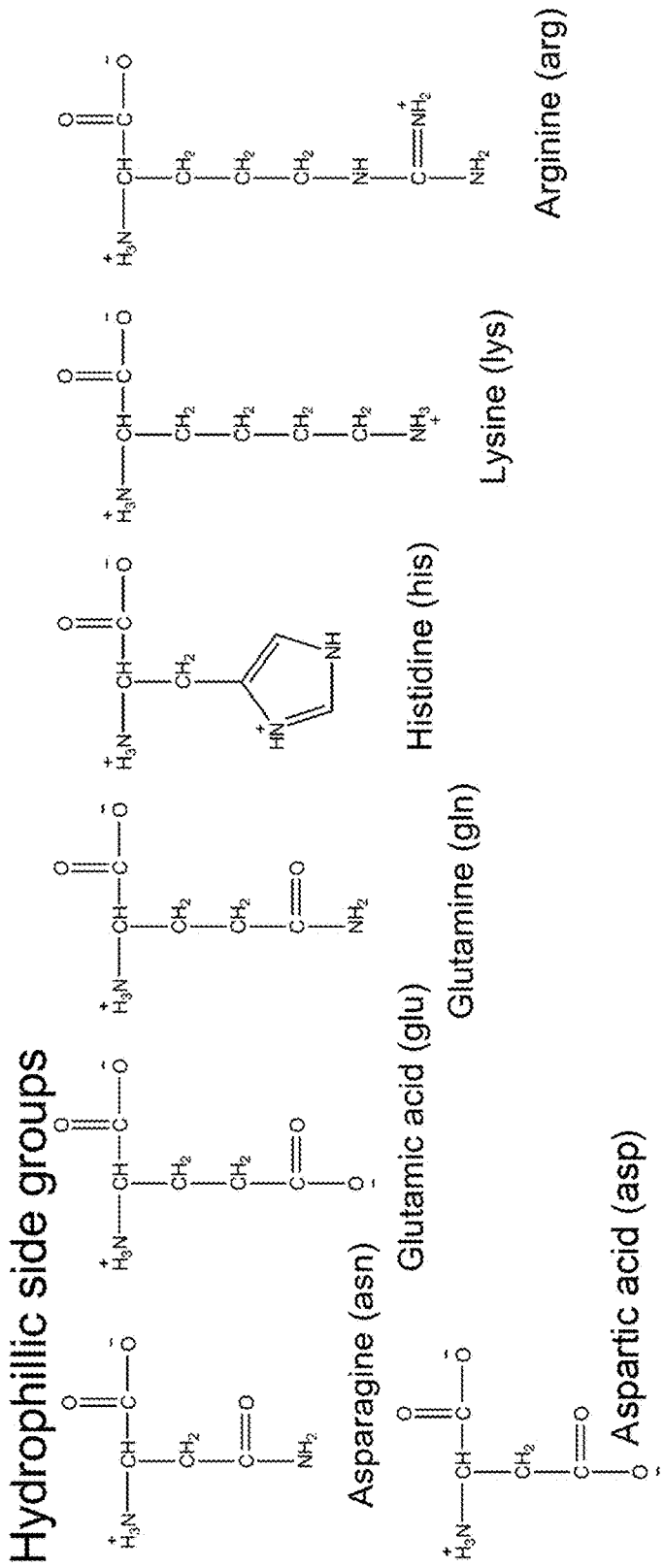
FIG. 13 shows exemplary hydrogen bonding sites for various amino acids.

Reagents may also be configured to form transient bonds with amino acids to analyze peptides. FIG. 13 shows examples of hydrogen bond donor and acceptor sites on amino acids. Two or more nearby sites (labeled "D", donor or "A", acceptor) are available on asparagine, glutamic acid, glutamine, histidine and arginine. Single sites on lysine, serine, threonine, tyrosine and tryptophan could be-read in conjunction using a reagent that also forms hydrogen bonds to the peptide backbone. Aromatic reagents can recognize amino acids with aromatic rings (histidine, tyrosine, proline and tryptophan) by means of pi-stacking. Accordingly, peptides may be analyzed according to the devices and methods described herein. FIG. 76 shows exemplary reagents for recognizing a peptide backbone and for recognition of side chains of amino acids.

Tunnel Gap

Units of a polymer, such as nucleosides of DNA or amino acids of a protein are detected as they diffuse through a tunneling gap or are driven through it by electrophoresis. The width of the gap may be fixed or dynamically adjustable. The gap is preferably fixed. The gap comprises the space between the two electrodes. The gap is adjusted to a size such that each target unit fits into the gap. The gap may have a width of about 0.5 to about 6 nm, such as about 1 to about 4, about 1.5 to about 3.5 nm, about 2 to about 3 nm, or about 2 to about 2.5 nm. The gap width may vary depending on the reagent being used and the target polymer unit(s) to be analyzed. In the case of two electrodes functionalized with 4-mercaptobenzamide, the gap may be about 2 to about 2.5 nm, such as about 2.1 to about 2.2 nm, or about 2.16 nm (when the gap conductance is 20 pS—typically used for DNA reads). In the case of two electrodes functionalized with imidazole-2-carboxyamide, the gap may be from about 2.2 to about 2.6, such as about 2.3 to about 2.5 nm from about 2.35 to about 2.4 nm, or about 2.37 nm (when the gap conductance is 20 pS—typically used for DNA reads). The gap distance may be determined as described below. FIG. 1 shows the distinctive hydrogen bonding formed with each of the four DNA nucleosides in one fixed tunnel gap. The 4-mercaptobenzene forms hydrogen bonds with each of the four nucleosides. Hydrogen bonds are circled and "S" stands for the deoxyribose sugar moiety. These structures were generated by computer simulation, and probably represent the actual structure quite well, because the 4-mercaptobenzamide was used in organic solvent. In the case of the reader molecules that work in water, attempts to model the structures are complicated by competition for hydrogen bonds with water molecules, and the interactions of aromatic rings mediated by water which pushes them together to form pi-stacking interactions.

The exact size of the gap may be important in obtaining reliable reads. It should be sized so that the majority of time (or majority of signals generated) are caused by the presence of just one unit of the polymer in the gap. Suitable gap widths may be determined by using a device capable of a dynamically adjusting the gap. In some embodiments, a dynamically adjustable device may be used to analyze target units. In either case, the gap width may be determined or set as follows: The electrodes are approached together until a chosen tunnel current is achieved at a particular bias. For example, a current of 6 pA at 0.5V bias corresponds to a gap of 2.5 nm when tunneling in 1,2,4-trichlorobenzene. The gap is maintained by applying active servo control as is well known in the art for scanning tunneling microscopy. In certain embodiments, the servo control has a frequency of response limited to 100 Hz or less.

Figure 2A:
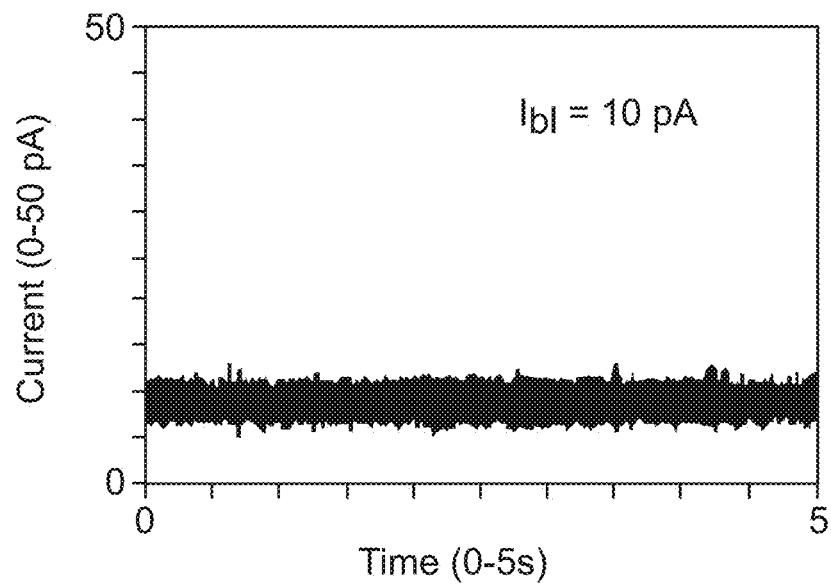
FIGS. 2A-2B provides exemplary background tunneling signals in TCB for a bias of 0.5V.
Figure 2B:
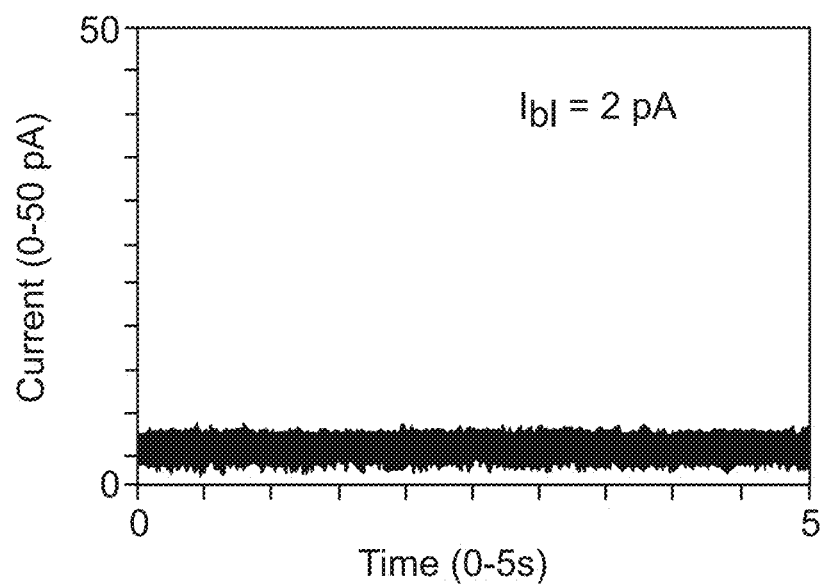
Figure 4:
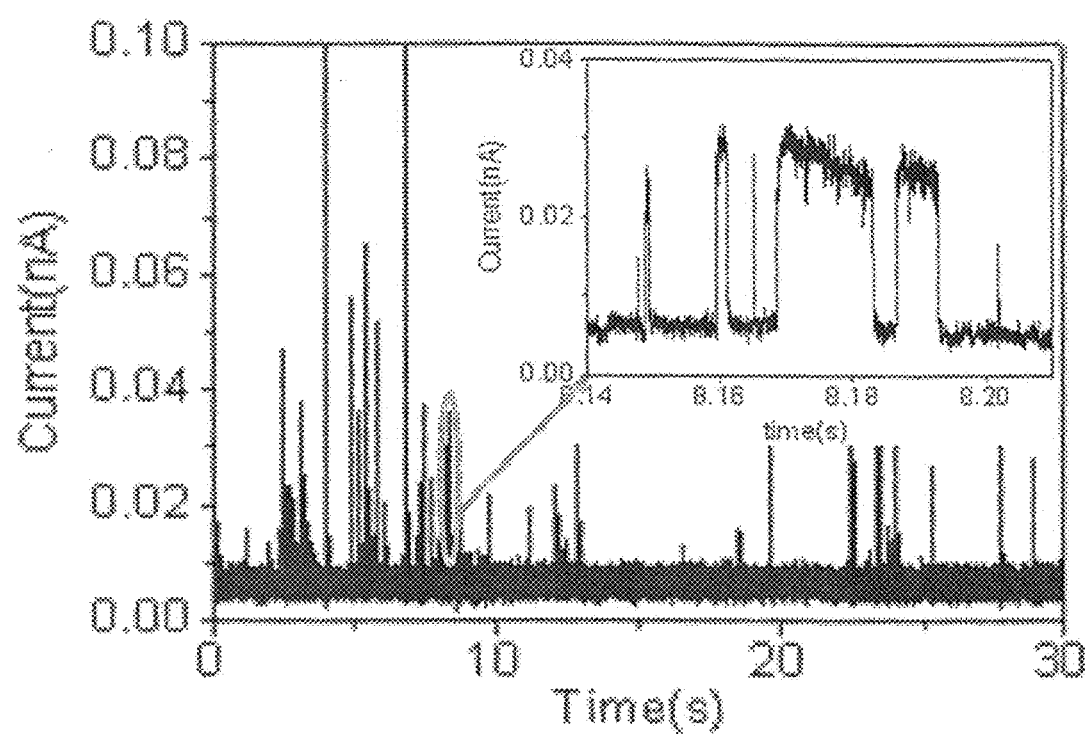
FIG. 4 provides an exemplary plot of current vs. time trace for V=0.5V, background current=6 pA when adenosine diffuses into the gap. The inset shows a blow-up of a binding signal. Similar types of signals are observed for all four nucleosides. See FIG. 15.
Figure 6:
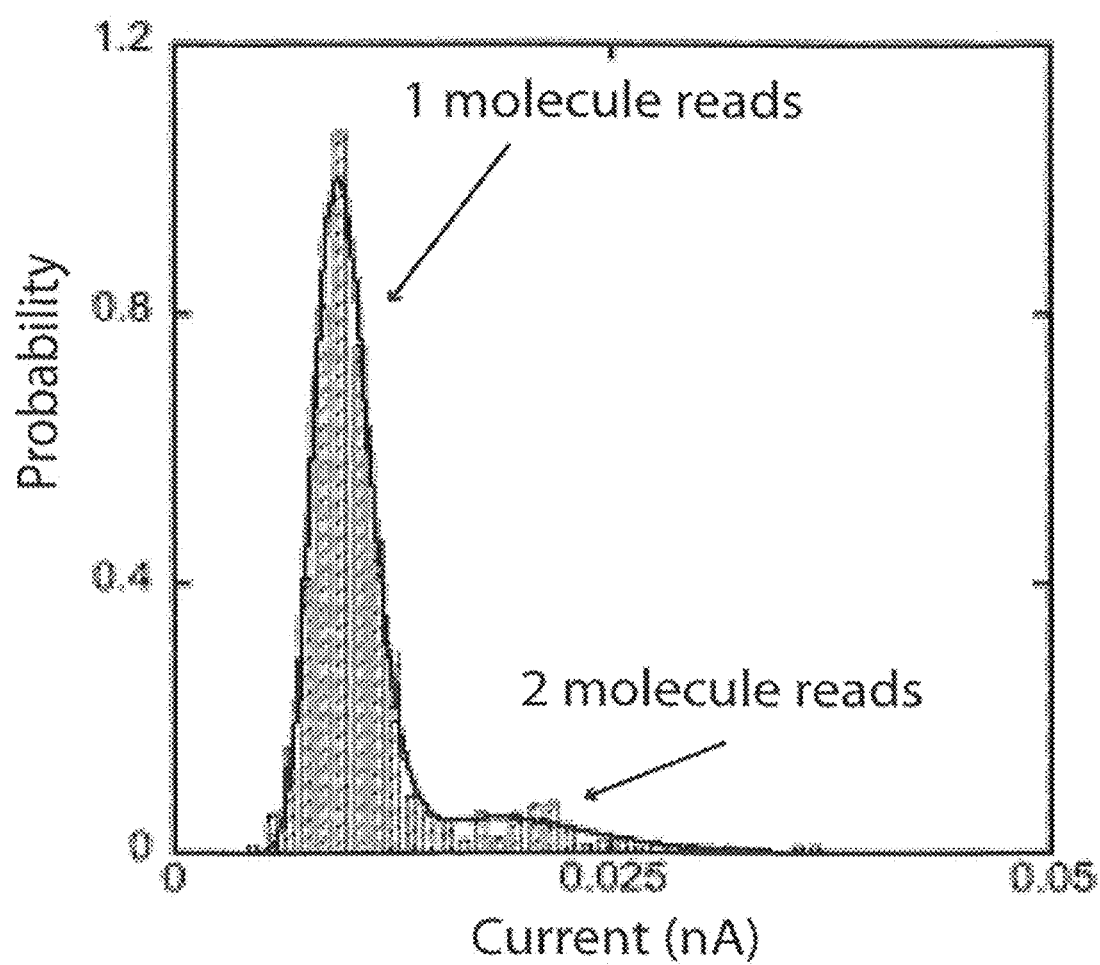
FIG. 6 shows a exemplary distribution of current spikes for both electrodes when functionalized (dG, V=0.5 V, current=6 pA). A small fraction of reads at twice the peak current for the main peak signal simultaneous trapping of two molecules in the tunnel gap.

Provided that the gap is kept large enough, the background tunneling signal is free of features, as shown in FIG. 2. When molecules bind in the gap, transient current spikes are observed in the tunnel gap (FIG. 4). With both electrodes functionalized, a narrow distribution of current peaks is observed at a characteristic current for each nucleoside (FIG. 78). However, identifying the specific nucleoside from the current signal is complicated by a high-current tail on the distribution, attributable to more than one target molecule binding in the gap simultaneously. This may give rise to a second peak in the current distribution at twice the current of the main peak (FIG. 6). The relative frequency of the multi-molecule reads increases as the gap is made smaller (baseline conductance or current increased) so that more contacts across the electrodes become possible. This increasing frequency of two molecule reads is shown in FIG.

Figure 7A:
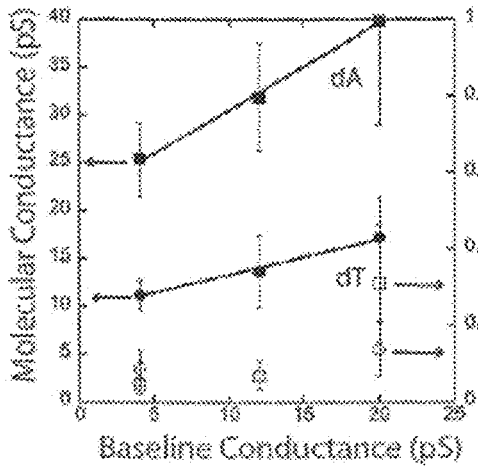
FIGS. 7A-7C provide a summary of exemplary reads.
Figure 8:
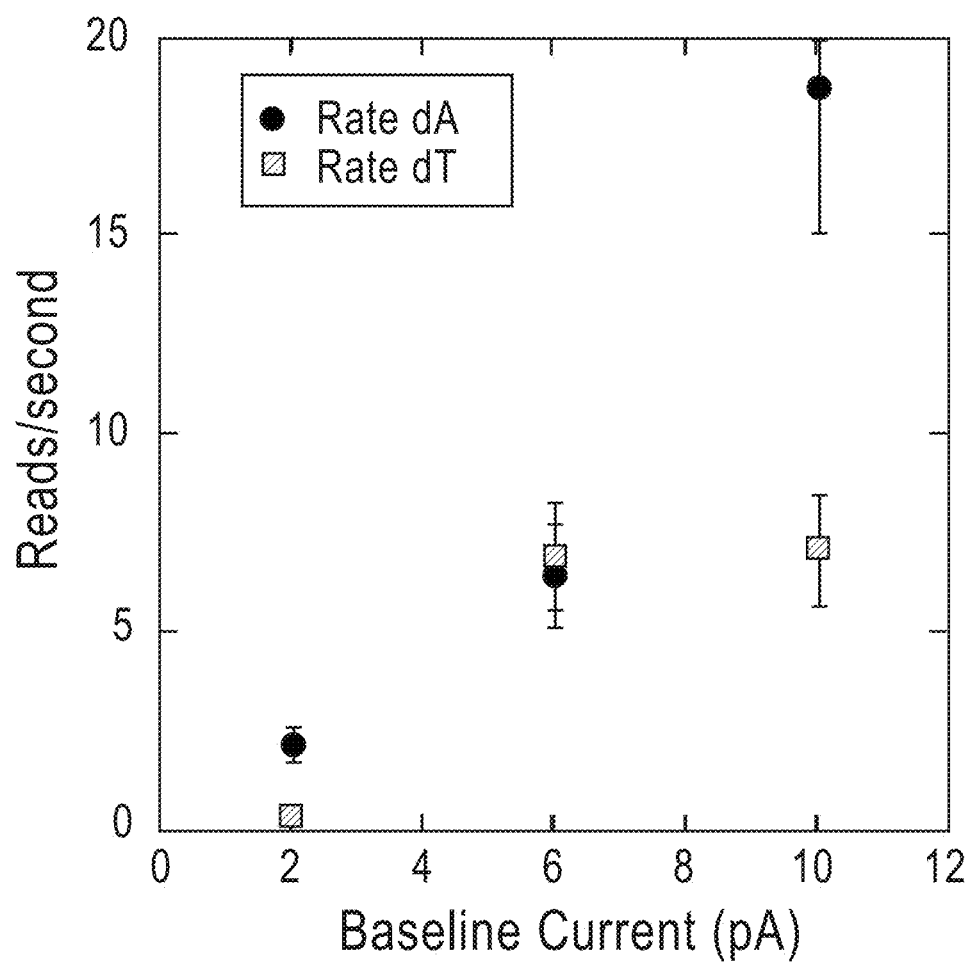
FIG. 8 shows that the read frequency falls as an exemplary tunnel gap is made larger (i.e., the tunnel current baseline, Gb1 is made smaller).

7A (which also shows how the peak currents increase with decreasing gap). Thus, making the gap larger has two deleterious effects: first, the peak currents fall (as shown in FIG. 7A), and second, the read-rates decrease for a given concentration of target (FIG. 8).

Thus, in some embodiments, important elements include (a) the incorporation of a variable and controllable tunnel gap with a nanopore through which the target polymer can be translocated to present one element at a time to the reading system (i.e., one base at a time for a DNA polymer); and (b) the use of reagents that bind all targets in some manner or another, the gap being adjusted to such a size that just a few distinct binding geometries exist for the targets, thereby generating distinctive signals.

Nanopores

In some embodiments, the device may be equipped with one or more nanopores, through which the polymer may be directed to the tunnel gap for analysis. The nanopores may be configured to permit the flow of the polymer to the tunnel gap one unit at a time. Thus, a nanopore for analyzing DNA may be smaller than a nanopore for analyzing a peptide.

Figure 9:
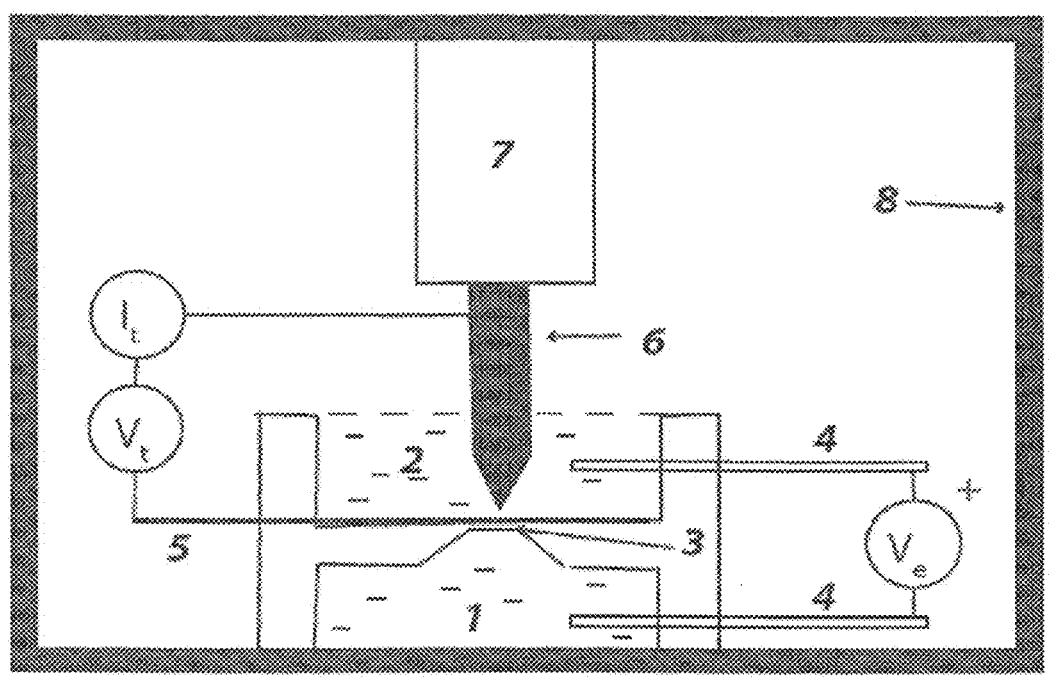
FIG. 9 graphically depicts an exemplary embodiment of the present invention.

Such an embodiment is illustrated in FIG. 9 for a tunnel junction with a variable gap. Details of the gap itself are given in FIGS. 10A-F. Details of a fixed gap device are given in FIG. 60. A polymer to be sequenced, such as DNA, is present in a fluid reservoir 1 (shown in cross section). The fluid containing the polymer may flow through an array of nanopores 3, or may be optionally driven through the nanopores by an electrophoretic bias, $V_e$ applied between the first reservoir 1 and a second fluid reservoir 2 by means of reference electrodes 4. Both reservoirs are filled with electrolyte, for example 1M KCl, and, in addition, the pH of reservoir 1 may be adjusted to a large value (pH=11 or 12) in order to maintain the target DNA in its single stranded form. If independent verification of translocation from electrical signals is not required, the electrolyte solution in the collection reservoir 2 is preferably made small (mM) to minimize electrochemical leakage. In certain embodiments, the nanopores are electrically conductive and connected by an electrode 5 plated onto the top of the nanopore array. The array may be probed by one or more second electrodes 6 held in place by a scanning transducer 7, such as the x, y, z scanning elements well known in the art of scanning probe microscopy. The scanner may be attached to the nanopore array via the rigid frame 8.

Figures 10A, 10B:
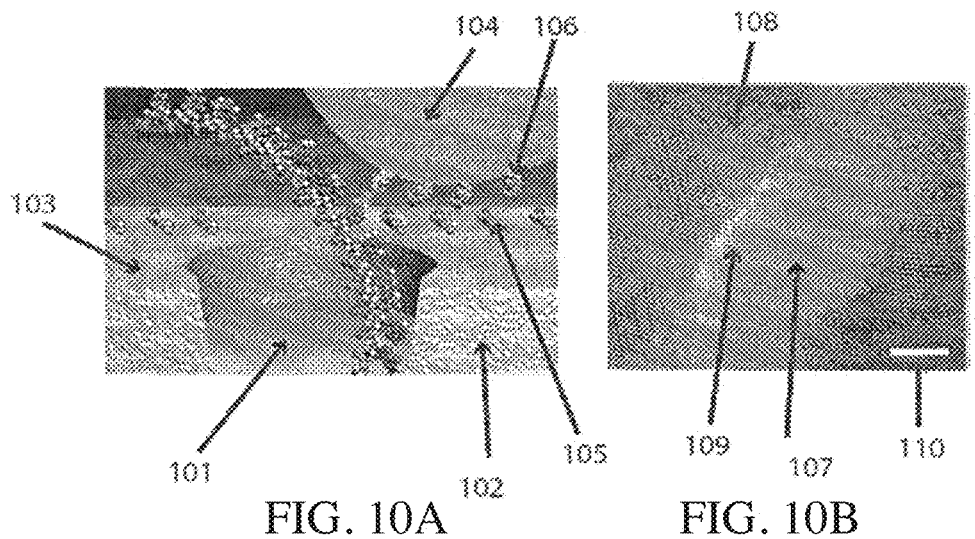
FIGS. 10A-10B provide details of an exemplary tunnel gap and nanopore array utilizing a gold or titanium nitride probe (FIG. 10A) and a gold or titanium nitride coated nanopore (FIG. 10B). The scale bar (110) in the electron micrograph of FIG. 10B is 2 nm.

Exemplary illustrations of the tunnel junction are shown in FIG. 10. FIG. 10A shows a gold probe reading sequence as a DNA molecule passes between the probe 104 and a gold or TiN electrode 103 on top of a nanpore 101 through which the DNA is translocated by electrophoresis. The nanopore 101 is shown in cross section—it is drilled through a silicon, silicon nitride or silicon dioxide substrate 102. Reading reagents 105 and 106 are attached to the probe 104 and metal electrode 103. An electron micrograph in FIG. 10B shows a nanopore 107 in a silicon nitride substrate that has been coated with a thin (20 nm) layer of gold 108. The act of drilling the pore causes the gold to recrytaliize around the pore, so that a sharp, atomically ordered ledge of gold 109 protrudes over the edge of the nanopore to form one of the reading electrodes for the polymer.

Figures 10C, 10D:
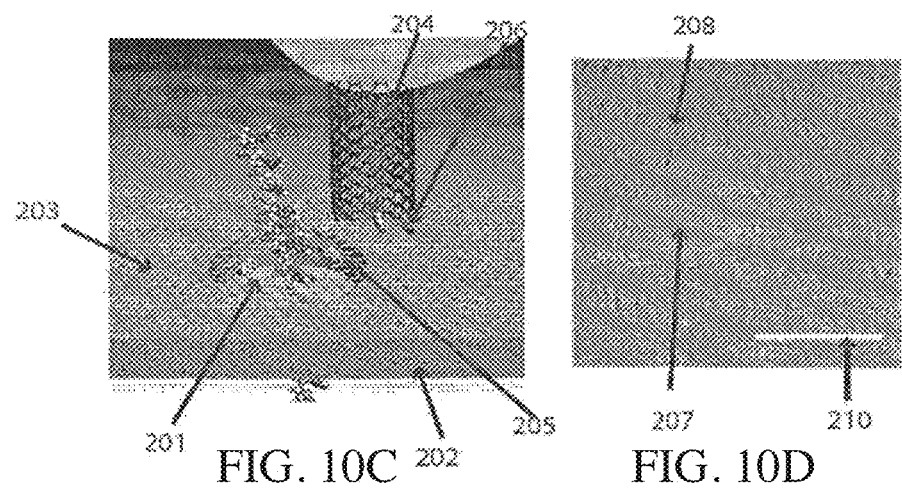
FIGS. 10C and 10D provide details of an exemplary tunnel gap and nanopore array utilizing a carbon nanotube probe (FIG. 10C) and a graphene nanopore (FIG. 10D). The scale bar (210) in the electron micrograph of FIG. 10D is 10 nm.

FIG. 10C shows an embodiment in which a probe bearing a carbon nanotube electrode 204 is held over a nanopore 201 in a graphene substrate 202 supported on a silicon nitride substrate 203. Reading reagents 205 and 206 are attached to the CNT 204 and edges of the graphene nanopore 201. The electron micrograph in FIG. 10D shows a nanopore 207 drilled in a graphene multilayer 208.

Figures 10E, 10F:
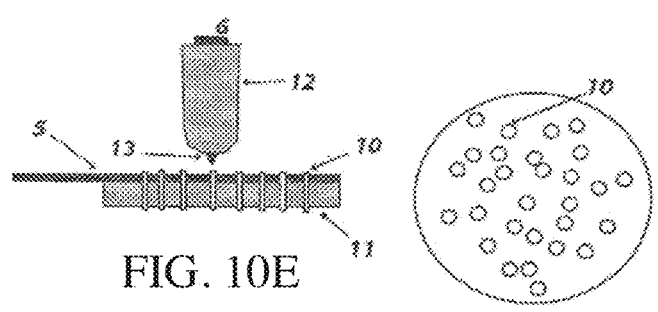
FIGS. 10E (cross sectional view) and 10F (top-down view) provide details of an exemplary tunnel gap and nanopore array utilizing metal probe and an array of carbon-nanotube nanopores.

FIGS. 10E and 10F show an embodiment in which a metal probe 13 protruding from insulation 12 is held over an array of carbon nanotube nanopores (one nanopore is labeled as 10) protruding through a dielectric substrate 11 coated with a thin metal electrode 5 through which the carbon nanotubes protrude. Such an array may be fabricated by CVD growth of nanotubes from a silicon surface, subsequently filled with silicon nitride with the underlying support etched away, as described by Holt et al., *Fast Mass Transport Through Sub-2-Nanometer Carbon Nanotubes*. Science, 2006. 312: p. 1034-1037, hereby incorporated by reference. For example, the top side of the membrane may have a layer of Au evaporated onto it to act as a contact (of thickness 10 to 100 nm) before the remaining protruding carbon nanotubes are removed by plasma etching. Electrophoretic translocation of DNA through carbon nanotubes has recently been demonstrated by Liu et al., *Translocation of single-stranded DNA through single-walled carbon nanotubes*. Science, 2010, 327, p 64-67, hereby incorporated by reference. The probe 6 maybe covered with a layer of insulation 12 leaving a small amount (few square microns) of the apex exposed 13 as described by Nagahara et al., *Preparation and Characterization of STM Tips for Electrochemical Studies*. Rev. Sci. Instrum., 1989. 60: p. 3128-3130. This results in minimal electrochemical leakage current into the electrolyte solution.

In some embodiments, the components described above may be configured into a microarray or chip as illustrated, for example, in FIG. 60. Here a supporting material 302 (silicon, silicon oxide or silicon nitride) is coated with a thin metal electrode 303, for example TiN deposited by atomic layer deposition, then covered with a layer of a dielectric 304 of a thickness 308 chosen to be optimal for the reading reagents used. For most of the reagents described here this thickness is from 1.5 to 3 nm. A second electrode 305 is deposited and covered with a final dielectric layer 309. A nanopore 301 is drilled through the entire device (by means of an electron beam as is well known in the art) and the exposed metal electrode surfaces functionalized with reading reagents 306 and 307.

Metal electrodes may be formed around a nanopore by any conventional method. For example, Pt may be deposited by Focused Ion Beam chemical vapor deposition on a nanopore formed in a silicon nitride membrane. Metals, for example TiN, may also be deposited by atomic layer deposition or chemical vapor deposition and a pore etched or created thereafter. Metals may also be first coated on a membrane, such as SiN, Si, or $SiO_2$, and thereafter a pore drilled.

Graphene, an intrinsically conducting substance may also be used to as an electrode with a nanopore. In the case of graphene, a pore may be drilled in the graphene. Translocation for a graphene pore may be used for long oligomers, for example, for up to 48 kbp. When using graphene it is possible to only functionalize the edges of the pore.

Figure 11:
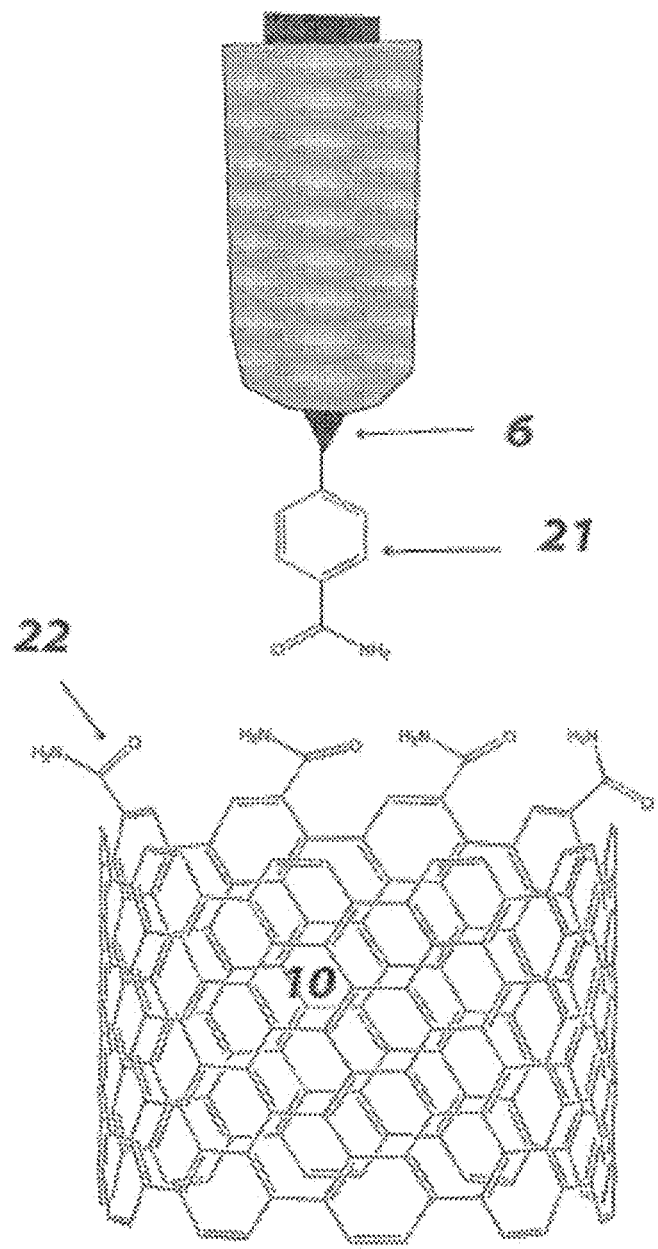
FIG. 11 illustrates gap chemistry for an embodiment of the invention.

An exemplary tunnel gap that uses a carbon nanotubes for a nanopore is shown in FIG. 11. The probe may be removed from the substrate, so functionalization with a different reagent on the substrate and probe is possible. In certain embodiments, the probe, gold or platinu, or a platinum alloy, is functionalized with 4-mercaptobenzcarbamide 21, a reagent that presents a hydrogen bond donor and acceptor in aqueous solution. The end of the carbon nanotube 10 may preferably be functionalized with carbamide moieties 22 using amide linkages (not shown) as is well known in the art. See Feldman, A. K., M. L. Steigerwald, X. Guo, and C.

Nuckolls, *Molecular Electronic Devices Based on Single-Walled Carbon Nanotube Electrodes.* Acc. Chem. Res., 2008. 41: p. 1731-1741.

Control of Translocation Speed

An additional advantage of using a reading gap functionalized with readding reagents is the long intrinsic binding time of the bases in the gap, as discussed in Example 13. A major problem with nanopores is the high speed of DNA translocation when a bias, big enough to dominate thermal fluctuations, is applied across the pore. The DNA translocates at speed of millions of bases per second, too fast for any proactical readout scheme. This problem is discussed by Branton et al., Nature Biotechnology volume 28, pp 1146-1153, 2008. In the case where the electrodes are funtionalized with molecules that bind the DNA base, one base can remain trapped for up to several seconds. A detailed analysis of the atomic force microscopy data presented in FIG. 59 (Huang et al, Nature Nanotechnology, vol 5 pp 868-873, 2010) shows that only a small force needs to be applied to increase the speed of the DNA through the nanopore functionalized with reading reagents. For example, the data of FIG. 59 can be used to show that at a bias of 80 m V across the nanpore, the DNA will translocate at a speed of 10 bases per second, increasing to over 100 bases per second at 120 m V.

Analysis of Polymers

The compounds, components, devices, and methods of the present invention may be used to analyze polymers. In certain methods of operation, a bias, such as from about 0.1 to 1 V, such as from about 0.3 to 0.7V, or about 0.5V ($V_t$), may be applied between the electrodes by means of voltage source, Vi in FIG. 9. The gap between the probe and the nanopore is adjusted by a transducer (7 in FIG. 9) until the desired set-point current is achieved. This may be from about 1 and 10 pA, such as from about 3 to 6 pA. For example, a translocation bias ($V_e$) may be applied to generate translocation of DNA through carbon nanotubes. Preferred values of Ye are between 0.1 and 1V.

In some embodiments, one of the electrodes (such as a probe) may be moved over the surface using the lateral scanning motion of the transducer 7 to locate a nanopore that is successfully translocating DNA, and the gap adjusted to achieve maximum discrimination in the tunneling signals. The gap would be set to a preferred initial value (e.g., 6 pA current at 0.5V) and small adjustments in background tunnel current made to optimize the separation of the signals from the four nucleosides.

Preferable additional components in analyzing a polymer are: (a) Rejection of fast data spikes (below 40 µS duration); (b) Automatic peak detection with a threshold set at 1 to 2 standard deviations above the noise level in a 0.3 s block of data; and (c) Adjustment of the servo gain that maintains the background current signal so that the frequency response is not faster than 35 Hz; (d) Means to turn the servo off during acquisition of data. When the servo that controls the average gap size is left on during data acquisition, the data are distorted as the servo adjusts the gap in response to the desired sequencing signal. For example, the traces in FIGS. 68, 73 and 74 were obtained with the servo on (with a slow response time as just described). The traces in FIGS. 70, 71 and 72 were obtained with a fixed gap (no servo control). The signals are much easier to intepret. In instruments with a variable gap, an optimal arrangement is to arrange to sample the background signal in the absence of DNA, stabilize the gap with a servo, and then turn the servo off to acquire data, resetting the gap then the DNA signal ceases.

In certain embodiments, the current signals are selected based on their duration, and the background current is fitted numerically over intervals of 0.5 s or less so as to establish a baseline for recognizing peaks above this background.

It will be recognized that a further advantage of the present invention is that any target that presents hydrogen bond donors and or acceptors (and/or aromatic rings that can pi-stack) that are located a small distance (up to 10 carbon-carbon bonds in distance) apart may be read in this scheme, adjusting the gap, if necessary, to optimize the signal from a subset of targets.

A Carbon Nanotube Forming Both Electrodes

Figure 12:
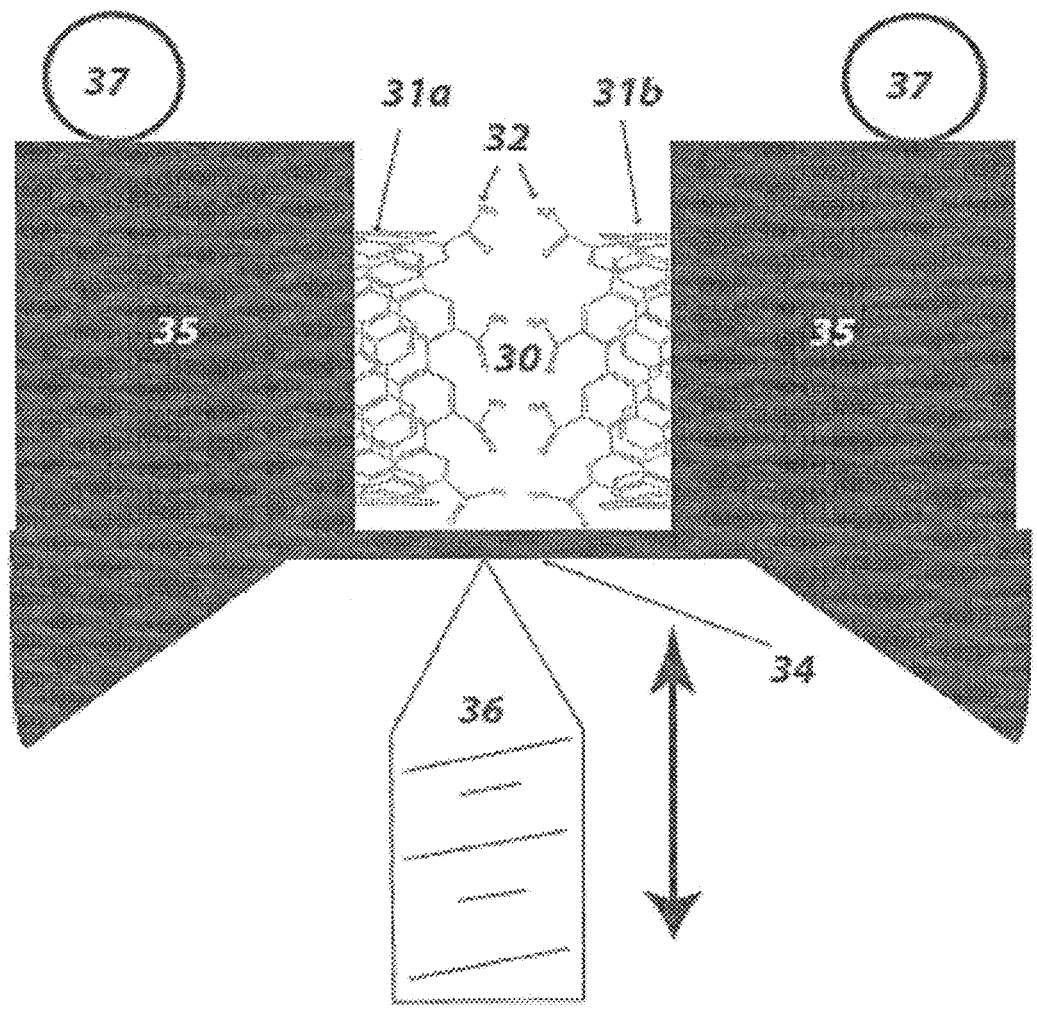
FIG. 12 illustrates an exemplary embodiment utilizing a gap in a carbon nanotube to form the electrode pair.

In other embodiments a carbon nanotubes may be used to form both electrodes as illustrated in FIG. 12. Carbon nanotubes as electrodes for sequencing polymers is described in 61/083,993 ("Carbon Nanotube Based Device for Sequencing Polymers"), which is herein incorporated by reference. DNA translocates across a small gap in the carbon nanotube 30 (see FIG. 12) using a device built on the surface of a silicon wafer as described in Liu et al., *Translocation of single-stranded DNA through single-walled carbon nanotubes.* Science, 2010, 327, p 64-67, and further in 61/083, 993 ("Carbon Nanotube Based Device for Sequencing Polymers"). A very small nick in the CNT may be made by brief exposure of the open part of the resist barrier 35 to an oxygen plasma etch followed by bending the device with a transducer 36 that pushes against a thin membrane 34 that flexes relative to fixed points 37 above the gap and displaced to one side of it. Bending the nicked carbon nanotube will break it, the extent of the gap being increased as the base on which the tube sits is further bent. The size of the opened gap is measured by means of a tunnel current that passes from one electrode (31*a*) to another (31*b*). When a desired gap size (2 to 2.5 nm) is attained, the ends of the CNT are functionalized with carbamide groups 32 as described above.

In certain methods, DNA is translocated through the gap 30 and the transducer 36 adjusted to optimize the separation of the tunnel current signals from bases that span the gap by binding carbamide groups on electrode 31*a* and 31*b*.

EXAMPLES

Example 1. Synthesis and Characterization of Materials 1.1 Materials and Methods Proton NMR ($^1$H) spectra were recorded on a Varian 500 MHz spectrometer. $^1$H chemical shifts in chloroform were referenced to the solvent peak ($\delta_H$=7.26 ppm). High resolution mass spectra (HRMS) were recorded using the atmospheric pressure chemical ionization (APCI) technique. The UV absorbance was recorded on a Varian Cary 300 UV spectrophotometer. Flash chromatography was performed using automated flash chromatography (Teledyne Isco, Inc. CombiFiash Rf). All chemical reagents were purchased from commercial suppliers and used as received unless otherwise noted. 2'-Deoxyadenosine and 2'-deoxyguanosine were purchased from TCI America; thymidine from Alfa Aesar; 2'-deoxycytidine from Sigma-Aldrich. Anhydrous N,N-dimethylformamide (DMF) in a Sure/Seal™ bottle was purchased from Sigma-Aldrich. 1,2,4-trichlorobenzene (TCB, 99%, Aldrich) was dried over molecular sieve (4 Å) under nitrogen, and then distilled under reduced pressure after filtration. All other solvents were used as received.

Figure 14:
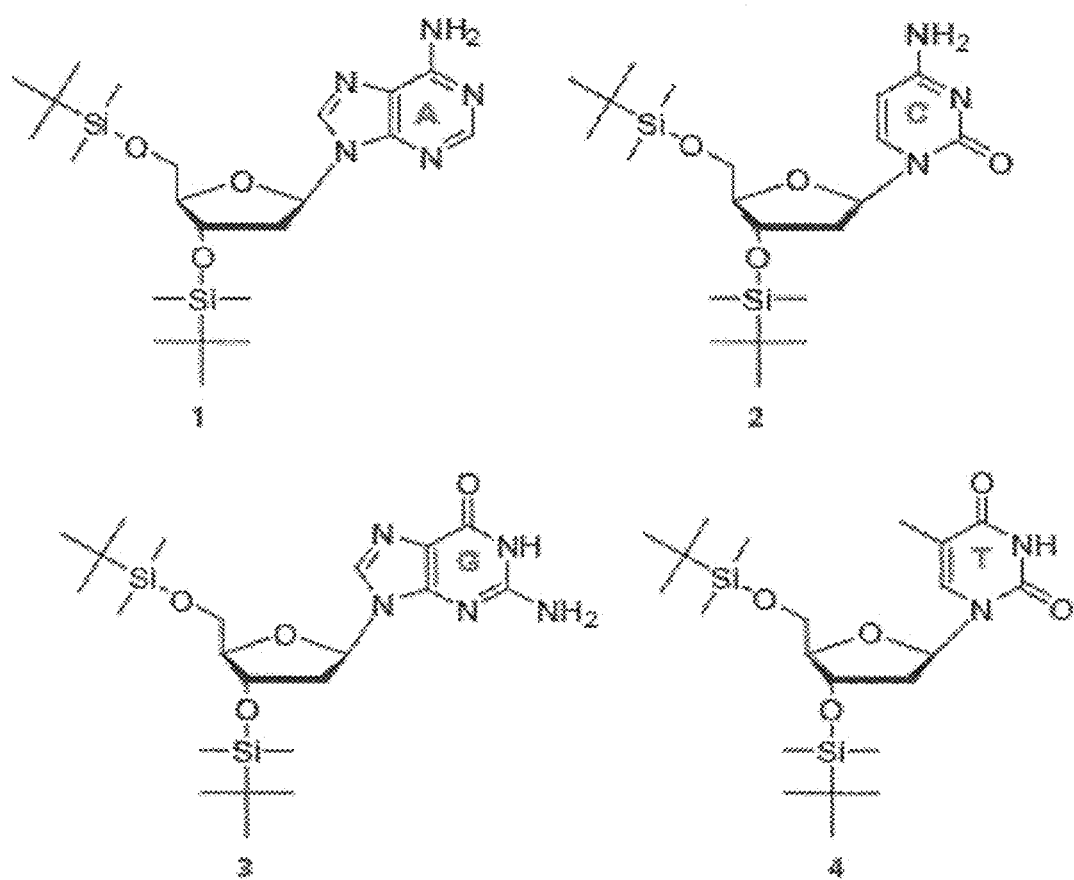
FIG. 14 provides exemplary chemical structures of nucleosides modified with T8DMS.

1.2 General Procedure for the Preparation of Bis(Tert-Butyldimethylsilyl) (TBDMS) Derivatives of Nucleosides (See FIG. 14)

See (D. A. Barawkar, R. K. Kumar, K. N. Ganesh, *Tetrahedron Letters* 48, 8505 (1992); W. Zhang, R. Rieger, C. Iden, F. Johnson, *Chem. Res. Toxicol.* 8, 148 (1996); P. Potier, A. Abdennaji, J. P. Behr, *Chem. Eur. J.* 6, 4188 (2000).

tert-butyldimethylsilyl chloride (TBDMSCl, 2.5 mmol) was added to a solution of dry nucleoside (1.0 mmol), dimethyl aminopridine (DMAP, 0.15 mmol) and imidazole (6 mmol) in anhydrous DMF (10 mL). After the reaction mixture was stirred overnight at room temperature under nitrogen, it was quenched with sat. aq. $NaHCO_3$, and extracted with dichloromethane. The combined organic layer was concentrated, and the residue was purified by silica gel flash chromatography with a gradient eluent of $CH_2Cl_2$—$CH_3OH$ from 100:0 to 100:5.

3',5'-Bis-O-(tert-butyldimethylsilyl)-deoxyadenosine (1): yield 80%. $^1$H NMR (500 MHz, $CDCl_3$): δ 8.29 (s, 1H, 2-H), 8.09 (s, 1H, 8-H), 6.65 (br s, 2H, NH2), 6.41 (t, 1H, 1'-H), 4.56 (dd, 1H, 3'-H), 3.96 (d, 1H, 4'-H), 3.82 (dd, 1H, 5'-H), 3.72 (dd, 1H, 5"-H), 2.59 (m, 1H, 2'-H), 2.39 (m, 1H, 2"-H), 0.86 (s, 18H, $(CH_3)_3$CSi), 0.05 (s, 6H, $CH_3$SiO), 0.03 (s, 6H, $CH_3$SiO). HRMS (APCI): calcd for $C_{22}H_{41}N_5O_3Si_2$+H, −480.2826; found, 480.2818.

3',5'-Bis-O-(tert-butyldimethylsilyl)-deoxycytidine (2): yield 17%. $^1$H NMR (500 MHz, $CDCl_3$) δ 8.07 (d, 1H, 6-H), 7.14 (br s, 2H, $NH_2$), 6.24 (t, 1H, 1'-H), 5.84 (d, 1H, 5-H), 4.38 (m, 1H, 3'-H), 3.92 (m, 2H, 5'-H), 3.77 (m, 1H, 4'-H), 2.42 (m, 1H, 2'-H), 2.08 (m, 1H, 2"-H), 0.92 (s, 9H, $(CH_3)_3$CSi), 0.88 (s, 9H, $(CH_3)_3$CSi)), 0.11 (s, 3H, $CH_3$SiO) 0.10 (s, 3H, $CH_3$SiO), 0.07 (s, 3H, $CH_3$SiO) 0.06 (s, 3H, $CH_3$SiO). HRMS (APCI): caicd for $C_{21}H_{41}N_3O_4Si_2$+H, 456.2714; found, 456.2722.

3',5'-Bis-O-(tert-butyldimethylsilyl)-deoxyguanosine (3): The crude product from chromatography was further purified by recrystallizing in ethanol (95%). yield 21%. $^1$H NMR (500 MHz, $CDCl_3$) δ 13.10 (br s, 1H, NH), 7.89 (s, 1H, 8-H), 7.11 (br s, 2H, $NH_2$), 6.26 (t, 1H, 1'-H), 4.57 (t, 1H, 3'-H), 3.97 (t, 1H, 4'-H), 3.81 (m, 1H, 5'-H), 3.77 (m, 1H, 5"-H), 2.51 (m, 1H, 2'-H), 2.37 (m, 1H, 2"-H), 0.91 (s, 9H, $(CH_3)_3$CSi), 0.90 (s, 9H, $(CH_3)_3$CSi)), 0.10 (s, 6H, $CH_3$SiO) 0.07 (s, 6H, $CH_3$SiO). HRMS: (APCI) calcd for $C_{22}H_{41}N_5O_4Si_2$+H, 496.2775; found, 496.2767.

3',5'-Bis-O-(tert-butyldimethylsilyl)-thymidine (4): yield 83%. $^1$H NMR (500 MHz, $CDCl_3$) δ 9.78 (br s, 1H, NH), 7.40 (s, 1H, 6-H), 6.27 (t, 1H, 1'-H), 4.33 (t, 1H, 3'-H), 3.85 (t, 1H, 4'-H), 3.80 (dd, 1H, 5'-H), 3.69 (dd, 1H, 5"-H), 2.18 (m, 1H, 2'-H), 1.93 (m, 1H, 2"-H), 1.84 (s, 3H, 5-$CH_3$), 0.85 (s, 9H, $(CH_3)_3$CSi), 0.82 (s, 9H, $(CH_3)_3$CSi)), 0.04 (s, 6H, $CH_3$SiO) 0.00 (s, 6H, $CH_3$SiO). HRMS: (APCI) calcd for $C_{22}H_{42}N_2O_5Si_2$+H, 471.2711; found, 471.2712.

1.3 Preparation of Stock Solutions

Saturated solutions of nucleosides (dA, dG, dT, dC) with hydroxyl groups protected by tert-butyldimethylsiyl groups (1.0 mg) were added into freshly distilled 1,2,4-trichlorobenzene (20 ml) and sonicated in an ultrasound bath for 10 min. The solution was filtered with filter paper (1#, Whatman) and stored in a glove box (with moisture under 0.5 ppm and oxygen under 0.5 ppm). The working solutions were prepared by diluting the stock solutions with TCB.

1.4 Concentration of the Stock Solutions

Since the UV absorbance of TCB overlaps that of nucleosides, concentrations of the stock solutions were determined through a solvent exchange. TCB was removed from an aliquot of the stock solution (1 ml) under vacuum at 80° C. and the residue was re-dissolved in the same volume of chloroform, and its UV absorbance was measured to determine concentration.

The UV extinction coefficients of all nucleoside derivatives in chloroform were determined at their maximum absorption wavelengths using a series of dA, dG, dT, and dC dilutions, respectively. The dilution factor varied from 3.5 to 200. The curve fitting was carried out in Origin 8. The resultant concentrations of the stock solutions are listed in the following table.

TABLE 1

Saturation concentrations of nucleosides in TCB stock solutions. The bottom row lists the final concentrations used in the tunneling measurements (concentrations that resulted in approximately equal read rates for each nucleoside).

|  | dA | dG | dT | dC |
|---|---|---|---|---|
| Wavelength (nm) | 260 | 257 | 268 | 280 |
| ε | 12690 | 11470 | 9480 | 7400 |
| $C_{sat}$ ($10^{-6}$ mol/L) | 5.8 ± 0.2 | 2.9 ± 0.1 | 7.7 ± 0.1 | 60.4 ± 7.8 |
| C ($10^{-6}$ mol/L) | 0.7 ± 0.02 | 2.9 ± 0.1 | 4.3 ± 0.06 | 0.8 ± 0.1 |

Example 2: Preparation and Characterization of Probes and Surfaces

Gold (S. Chang et al, *Nanotechnology* 20, 075102 (2009)) (Alfa Aesar, 0.25 mm diameter, 99.999% pure) and Pt (20% Ir) (L. A. Nagahara, T. Thundat, S. M. Lindsay, *Rev. Sci. Instrum.* 60, 3128 (1989)) probes were etched and the surfaces were prepared (J. A. DeRose, T. Thundat, L. A. Nagahara, S. M. Lindsay, *Surf. Sci.* 256 102 (1991)) and annealed in a hydrogen flame.

0.3 mg benzoic acid was dissolved in 2 mL N,N-Dimethylformamide (Sigma-Aldrich, >99.99% pure) that was degassed with argon. Substrates were immersed in this solution for two hours immediately after hydrogen flame annealing, then rinsed with N,N-Dimethylformamide, acetone and 1,2,4-trichlrobenzene and dried in flowing $N_2$ before use.

Prior to modification, probes were cleaned in piranha ($H_2SO_4$/30% $H_2O_2$, 3:1: creates heat and oxygen—treat with caution). They were then immersed into the 1 mM benzoic acid solution overnight, cleaned by N,N-Dimethylformamide, acetone, 1,2,4-trichlrobenzene and blown dry before use. All measurements were carried out in freshly prepared pure solvent or solutions of nucleosides.

Surfaces were characterized by ellipsometry, STM (A. H. Schafer, C. Seidel, L. Chi, H. Fuchs, *Adv. Mat.* 10, 839 (1998)) and FTIR (S. E. Creager, C. M. Steiger, *Langmuir* 11, 1852 (1995)). The FTIR spectra clearly show that the benzoic acid moiety is exposed and in its neutral form. Background tunneling signals were measured and shown in FIG. 2.

2.1 Polarization Currents and Electrochemical Leakage

The absolute values of peak current are affected by electrochemical leakage as follows: The tunneling current is set after backing out the background leakage current measured with the probe far from the surface. If this is substantial (tens to hundreds of pA) then, even though the probes are un-insulated (so that leakage is generated over their entire surface) the leakage can still change (at the pA level) when the probe is brought to the surface as a result of altered diffusion rates around the apex of the probe. Thus the correction applied for leakage with the probe far from the surface can overcorrect for leakage with the probe close to the surface. In consequence, the apparent tunnel current is overestimated, changing the real set-point from nucleoside to nucleoside if the leakage is different from one nucleoside solution to another. This effect is large enough to change the apparent order of the dC and dG peaks at the saturation concentrations (Table 1). Diluted to the working concentrations shown in Table 1, leakage currents at 0.5V bias were 1.0 to 2 pA (dA), 0.0 to 1.0 pA (dT) and 0.3 to 1 pA (dG). In the case of dC (0.8 µM) a current of 15 pA was observed initially, but this fell to a few pA after an hour of exposure to the solution. These backgrounds have been subtracted from the baseline tunnel currents reported here. They do not appear to cause significant errors as evidenced by the similarity between the data for single nucleosides and the data for mixtures. Examples of raw data for dT, dG and dC can be found in FIG. 15.

2.2 STM Servo Gain

The frequency response of the servo was determined by comparing 1/f noise plots without (FIG. 16 A) and with (FIG. 16 B) the servo applied.

Figure 15A:
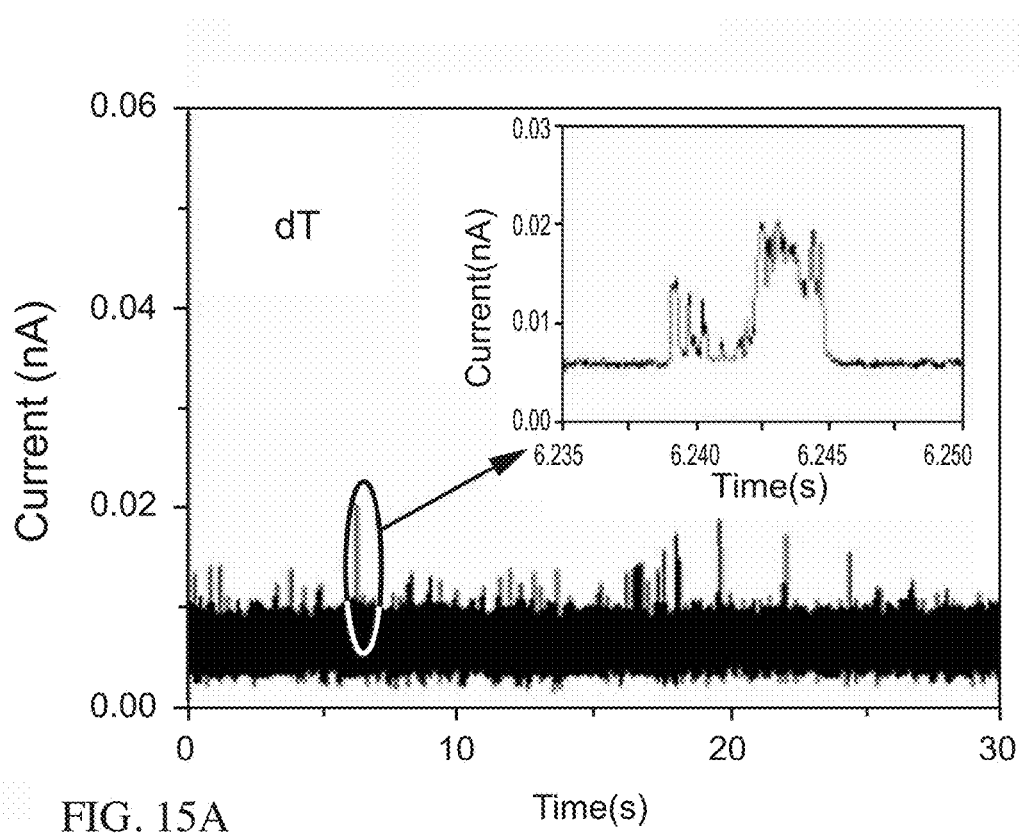
FIGS. 15A-15C provide exemplary current-time traces for $G_{b1}$=12 pS for 4.3 µM dT (FIG. 15A), 2.9 µM dG (FIG. 15B) and 0.8 µM dC (FIG. 15C) in TC8 with both electrodes functionalized with 4-mercaptobenzoic acid. The current scales for FIGS. 15A and 15B are the same.
Figure 15B:
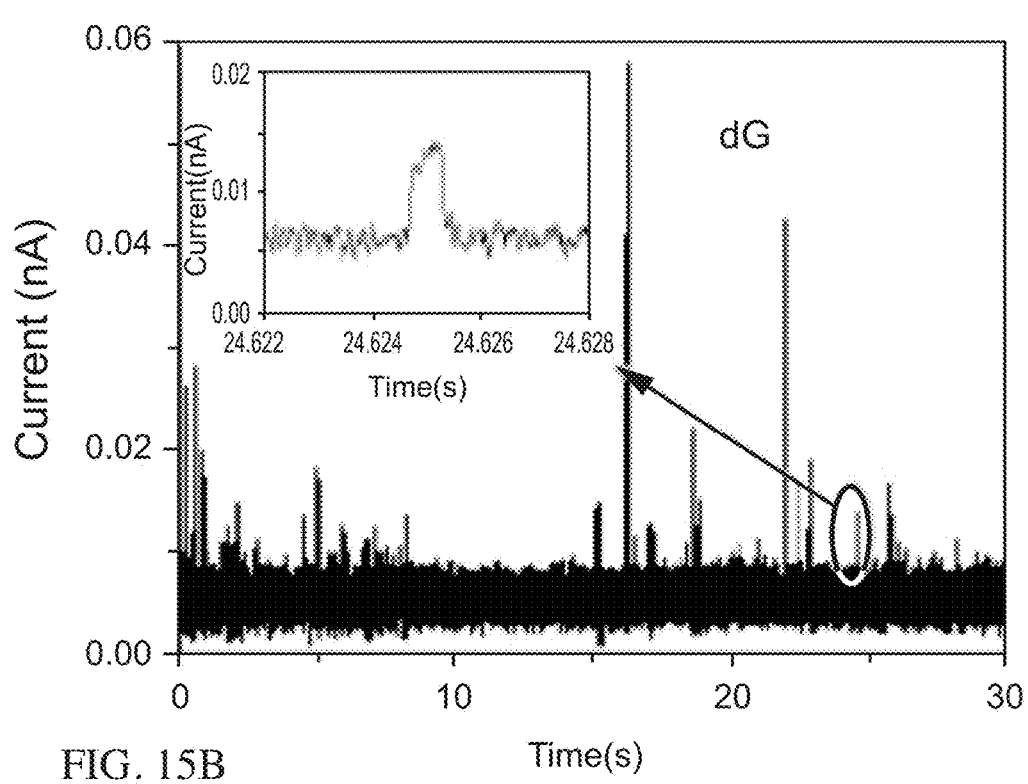
Figure 15C:
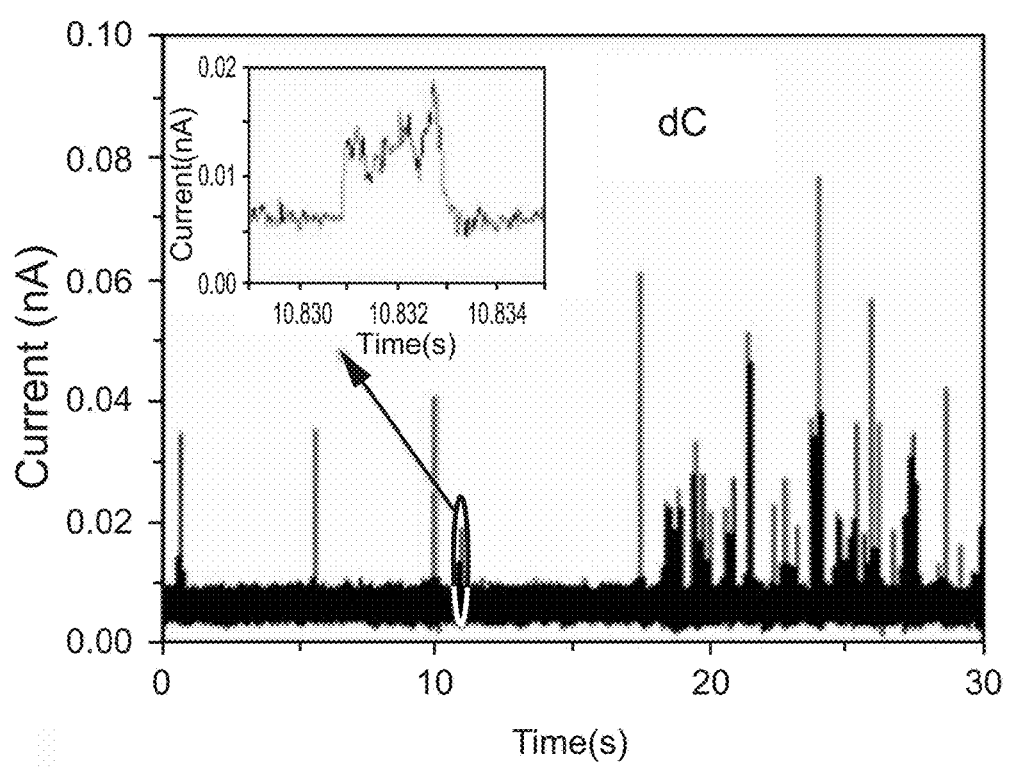
Figure 16A:
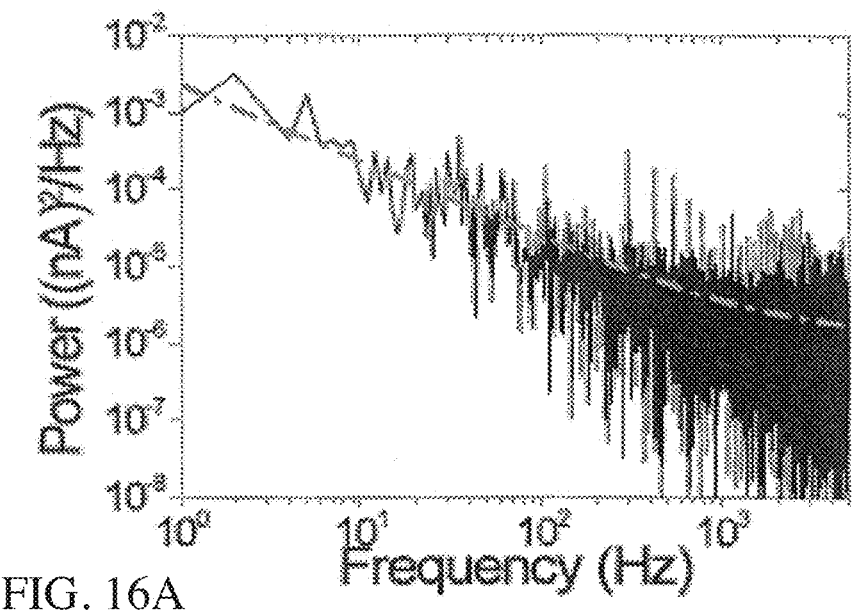
FIGS. 16A-16B provide exemplary noise spectra in open loop (FIG. 16A) and under servo control (FIG. 16B) with the gains settings used for acquiring the spike data. Dashed lines are fits to a 1/f spectrum.
Figure 16B:
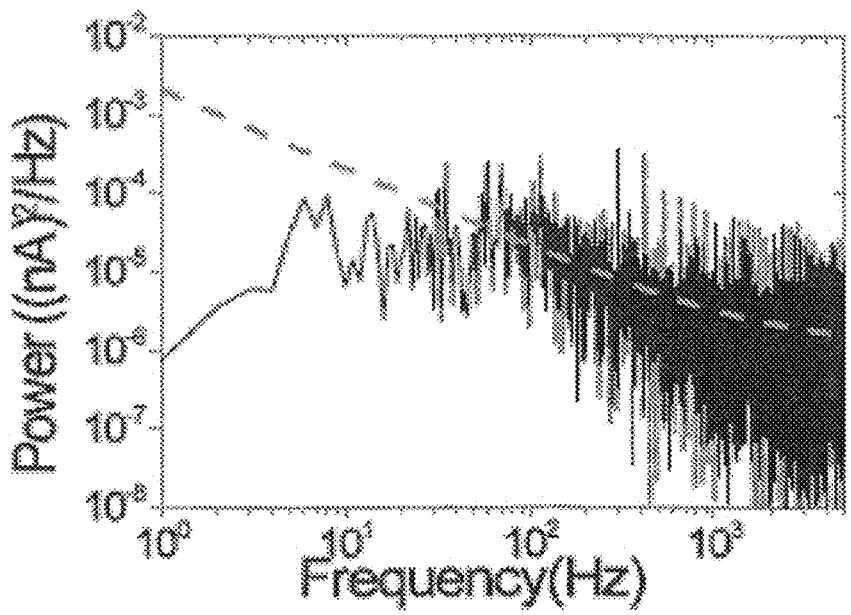

Current traces were Fourier transformed and displayed as a spectral density according to:

$$PSD = \frac{2(Re^2 + Im^2)}{n} = \frac{2}{N\Delta t}\frac{Re^2 + Im^2}{f_n} \quad \text{(Formula I)}$$

where n is the frequency channel number ($\Delta t$=20 µs and N=50000). The solid line in FIG. 16A is a fit to 1/f. With the servo loop closed (FIG. 16B) the noise data is suppressed below 35 Hz, corresponding to a 28 ms response time. This is long enough not to distort all but the longest pulses (the long pulses in the insets in FIG. 15 show a small fall-off in peak current level consistent with the measured servo response).

2.3 Automatic Peak Detection

Data analysis was automated both for speed and to eliminate operator bias. The one operator input to the process was to move the probe to quieter areas of the substrate if extremely noisy backgrounds (characteristic of contamination) were encountered.

The principle challenge lay with low frequency instabilities in background current that were. not completely corrected by the servo. If a small fixed threshold for acceptance of a peak was used, even a very short fluctuation of the baseline above this threshold produced a large number of spurious counts. This problem was overcome as follows.

Figure 17:
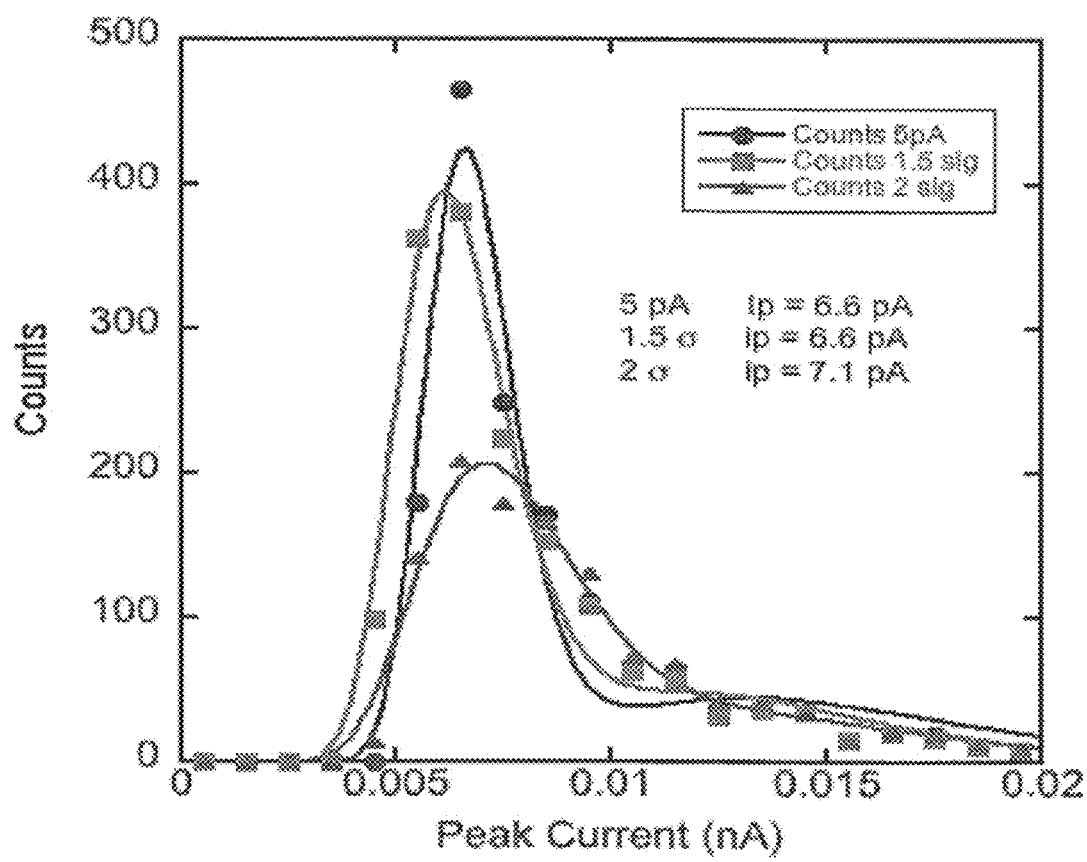
FIG. 17 shows two Gaussian log fits to an exemplary data set analyzed with a fixed (5 pA) cut off (circles), a variable 1.5 σ cut-off (squares) and a variable 2 σ cut off (triangles). The fitted peak shifts from 6.6 to 7.1 pA, a negligible change relative to the separation of peaks for different nucleosides.
Figure 18B:
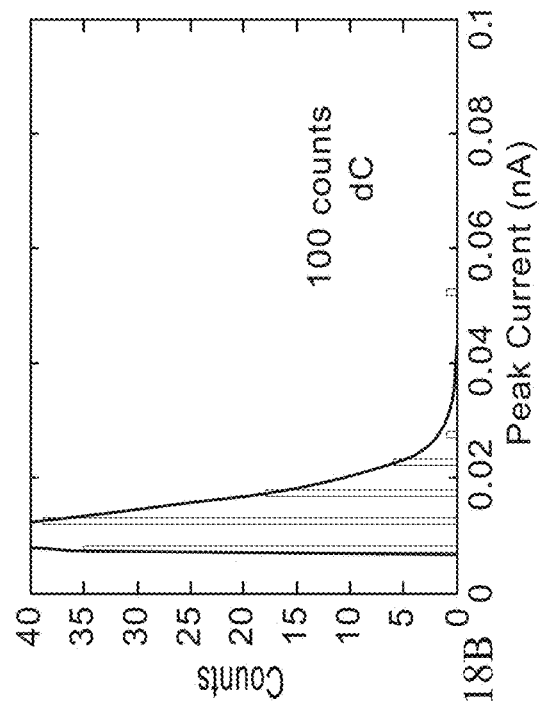
FIGS. 18A-18D shows exemplary current distributions obtained at $G_{b1}$=20 pS (V=0.5V) for bare electrodes for dA (FIG. 18A), dC (FIG. 18B), dG (FIG. 18C), and dT (FIG. 18D). The total counts recorded in 180 s at a nucleoside concentrations listed in Table 1 are listed on each panel. See Example 1.4.
Figure 18D:
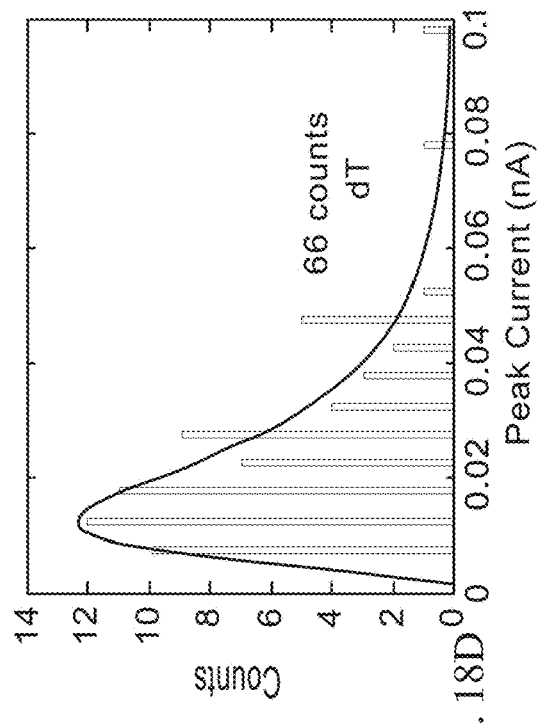
Figure 18A:
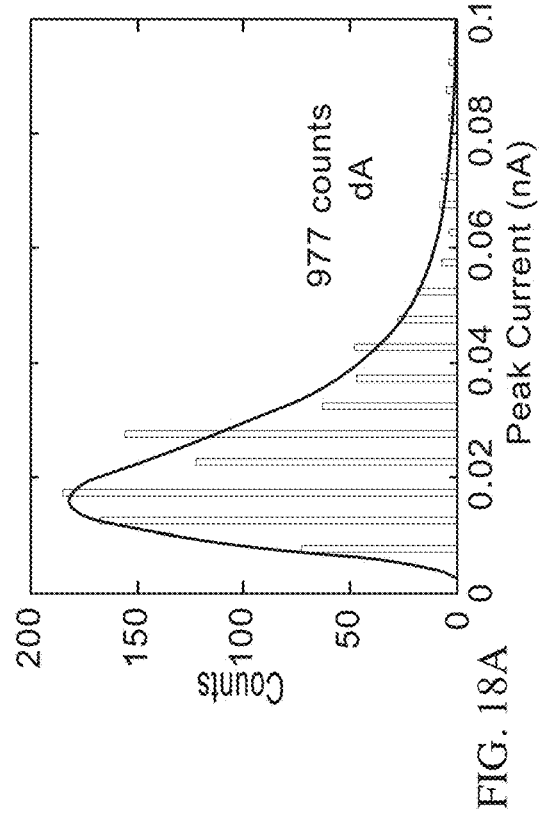
Figure 18C:
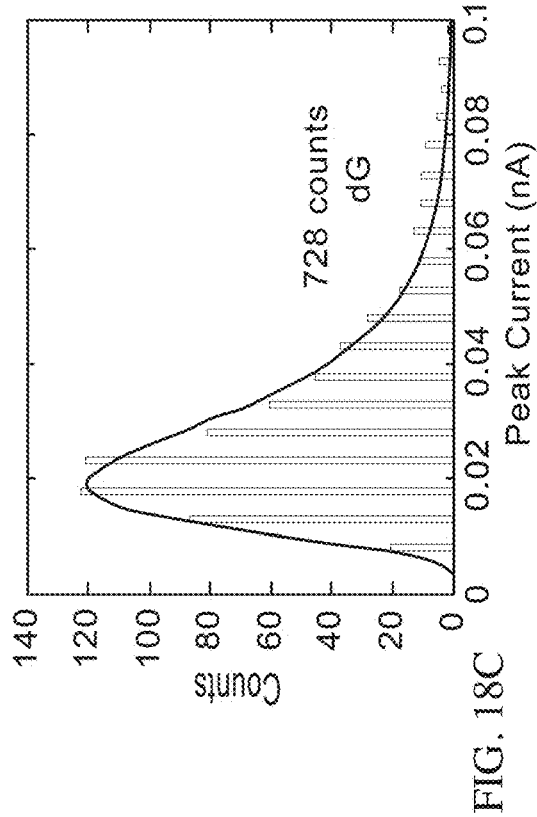
Figure 19A:
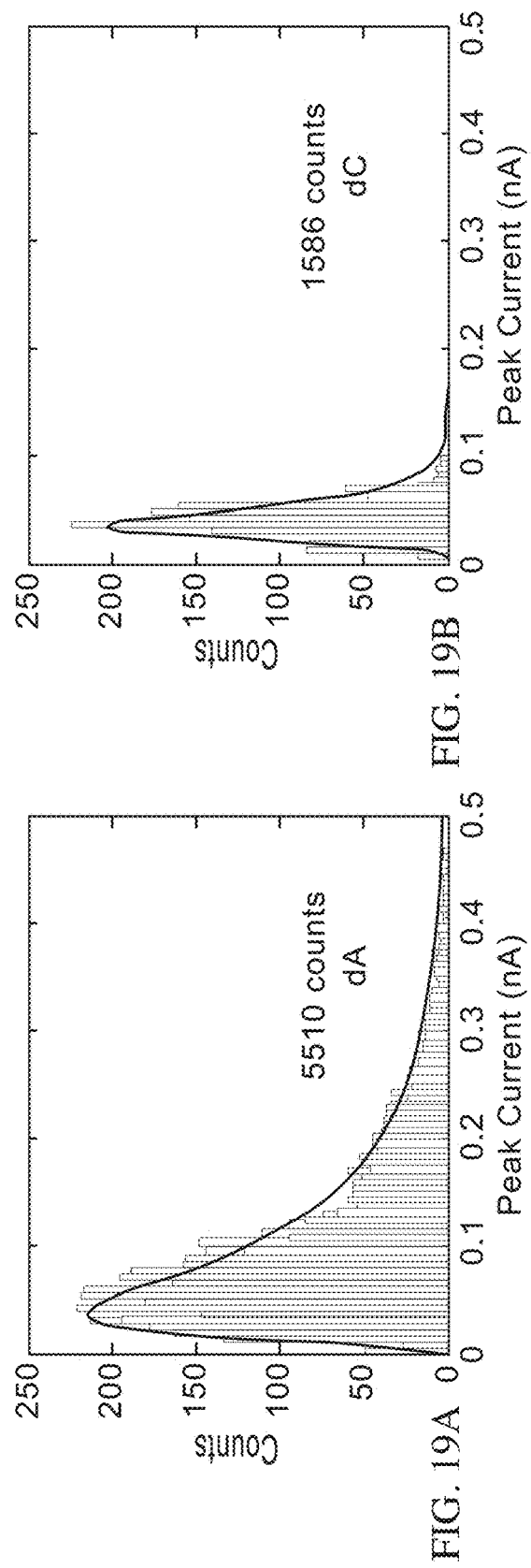
FIGS. 19A-19D show exemplary current distributions obtained at $G_{b1}$=40 pS (V=0.5V) for bare electrodes for dA (FIG. 19A), dC (FIG. 19B), dG (FIG. 19C), and dT (FIG. 19D). Note that some unambiguous reads of dA could be made because of the width of the distribution. The read rates are less disparate between purines and pyrimidines compared to the data acquired at $G_{b1}$=20 pS. See FIG. 18. Counts in a 180 s period are listed on each panel.
Figure 19B:
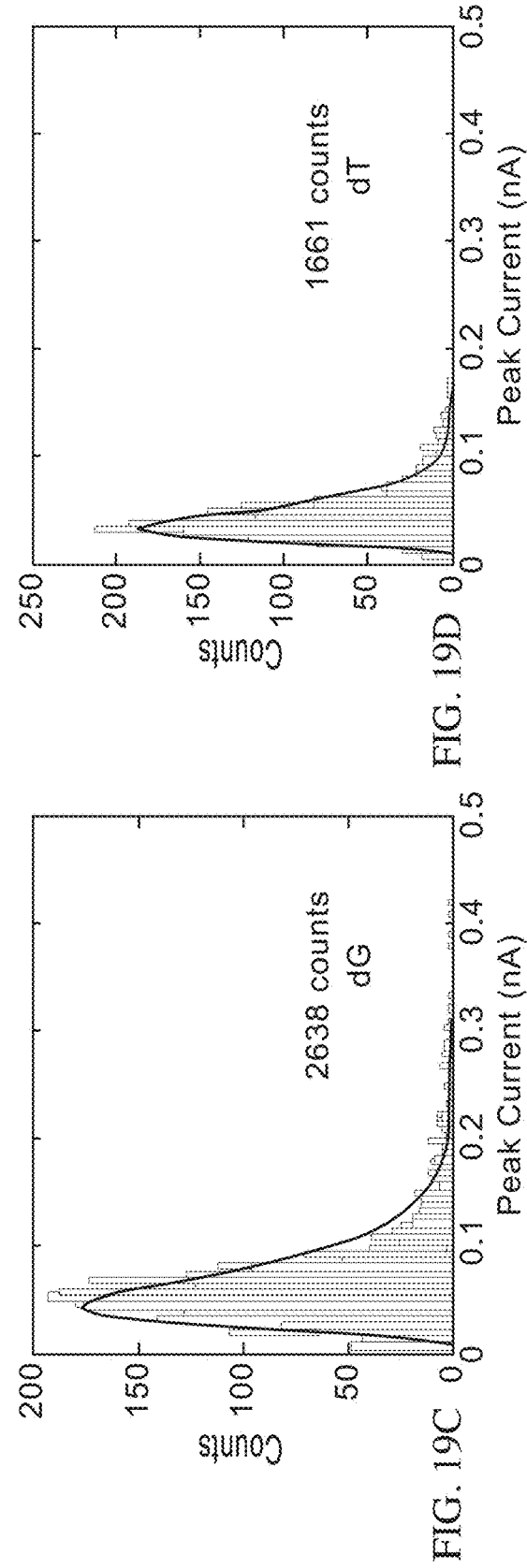
Figure 19C:
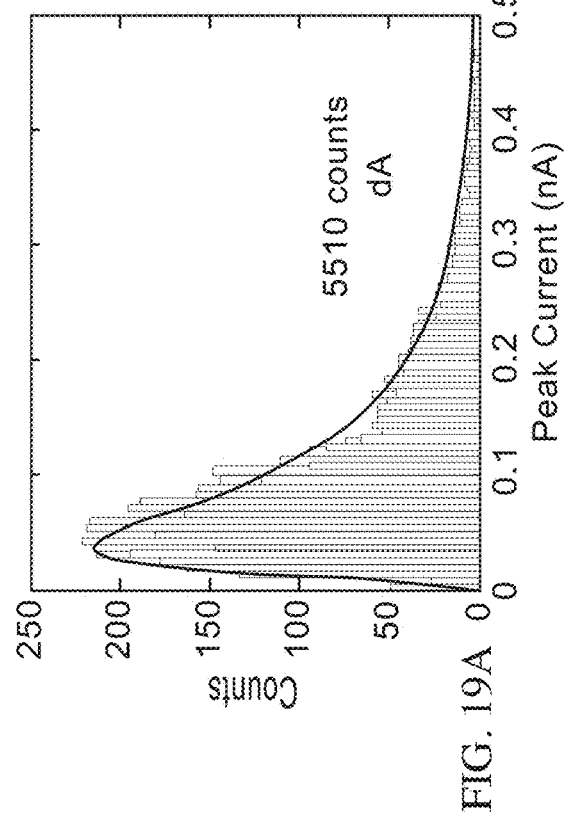
Figure 19D:
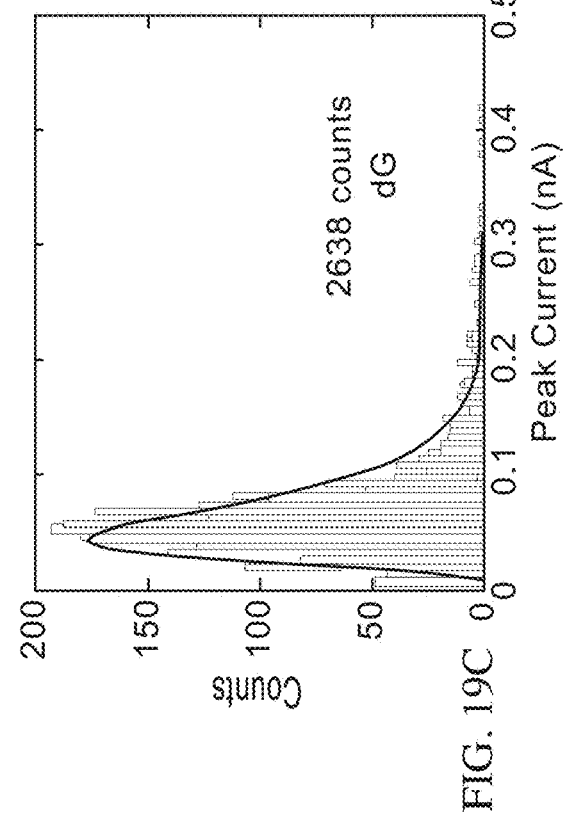

The current-time data (acquired at 50 kHz) were broken into 0.3 s blocks. The amplitudes in a block were binned and the bottom half of the data fitted by a Gaussian, the program checking that the mean of the Gaussian was equal to the desired baseline current. The HWHH of the Gaussian was used to determine the SD, a of the baseline noise. The data shown here were analyzed by setting the threshold to 20 above the noise in a 0.3 s run of data. Because the noise level varies over the duration of a run, this variable threshold results in a variable cut-off, and when data are aggregated, this can alter the shape of the distribution for the lowest current reads (i.e., for dT and data acquired with one electrode bare). The effect of three choices of cut-off on a 30 s run (i.e., 100 0.3 s segments) of data (dT, 4.3 µM, $G_{b1}$=12 pS V=0.5V) are shown in FIG. 17.

Very short pulses (at the limit of instrumental resolution) can dominate the data and do not appear to be sensitive to the identity of the nucleoside. Therefore, all spikes of only one (20 µs) or two data points duration (40 µs) were rejected. Distributions of spike lifetimes are provided in FIGS. 27-29.

2.4 Data Obtained with Bare Electrodes

Data obtained with bare electrodes is shown in FIGS. 18 and 19. FIGS. 18 and 19 show that distributions are asymmetric. We assume that the molecular configurations are randomly distributed, and that the tunnel current is• exponentially sensitive to changes in position. Thus, we used a Gaussian distribution in the logarithm of the current:

$$N(i) = N_0 \exp\left(-\frac{[\ln(i) - \ln(i_0)]^2}{[\ln(w)]^2}\right). \quad \text{(Formula II)}$$

The equation shown in formula II fits the data well as shown by the curved lines in FIGS. 18 and 19. The quality of the fit is demonstrated with a log-Jog plot of the data from FIG. 19A, shown in FIG. 20. The curved line is a parabola.

TABLE 2

Peak currents (lp), widths on the high current side of the distribution ($I_{0.5}^+$) and read-rates (RR) for the four nucleosides passing bare gold electrodes set at 20 pS and 40 pS conductance (bias = 0.5 V).

| | dT | | | dC | | | dA | | | dG | | |
|---|---|---|---|---|---|---|---|---|---|---|---|---|
| $G_{b1}$ | $I_p$ pA | $I_{0.5}^+$ pA | RR (s$^{-1}$) | $I_p$ pA | $I_{0.5}^+$ pA | RR (s$^{-1}$) | $I_p$ pA | $I_{0.5}^+$ pA | RR (s$^{-1}$) | $L_p$ pA | $I_{0.5}^+$ pA | RR (s$^{-1}$) |
| 20 pS | 12.4 | 15.3 | 0.4 | 10.0 | 6.1 | 0.6 | 15.9 | 14.6 | 5.4 | 18.7 | 15.2 | 4.0 |
| 40 pS | 32.4 | 22.6 | 9.2 | 35.1 | 21.6 | 8.8 | 36.6 | 70.0 | 30.6 | 44.1 | 37.5 | 14.7 |

The differences between Gaussian and Gaussian log fits was less marked for the narrower distributions measured with functionalized probes, though the fits with the Gaussian log function were still noticeably better than fits with Gaussians. Most data were fitted with a sum of two Gaussian, the second being centered at twice the current peak of the first:

$$N(i) = N_1\exp\left(-\frac{[\ln(i) - \ln(i_0)]^2}{[\ln(w)]^2}\right) + N_2\exp\left(-\frac{[\ln(i) - \ln(2i_0)]^2}{[\ln(w)]^2}\right) \quad \text{(Formula III)}$$

For the narrower distributions, the HWHH is given approximately by $$\Delta i_{\frac{1}{2}} = i_0(1 - \exp[0.8326\ln(w)]) \qquad \text{(Formula IV)}$$

2.5 Data for Mixed Solutions of Nucleosides

Figure 21:
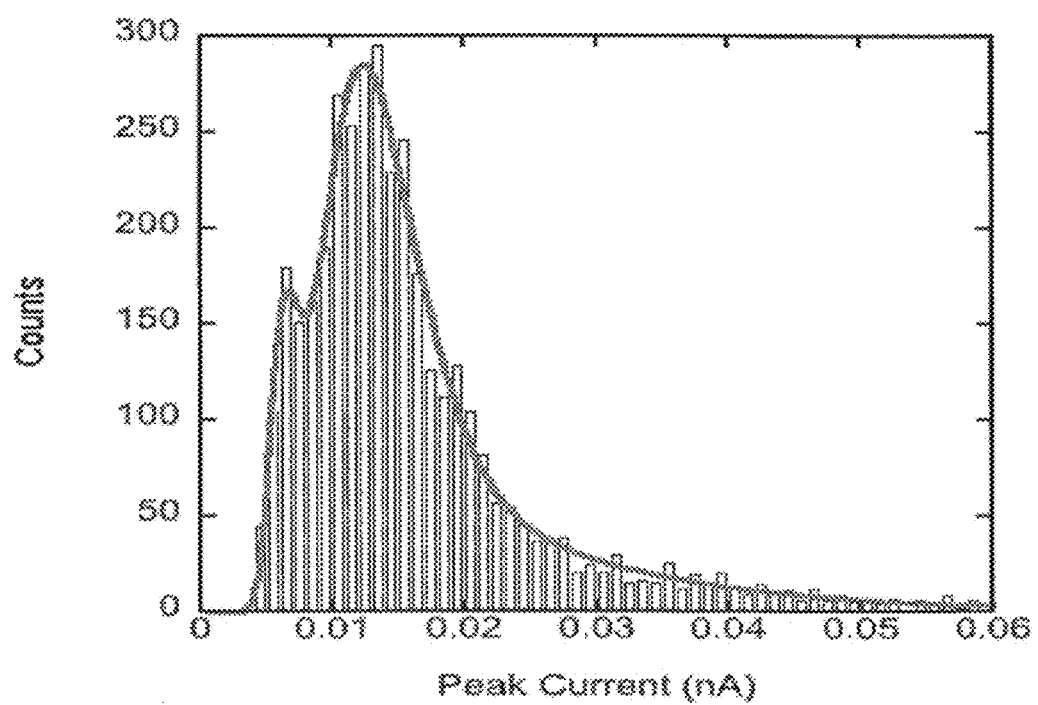
FIG. 21 provides an exemplary distribution for a mix of dT and dC, with the concentration of dT halved relative to that used for FIG. 5C. The distribution is fitted with three Gaussian log functions (solid line). The dT peak is located at 6.6 pA, the dC peak at 12.3 pA. The high current tail is fitted with a small fraction of dG+dC reads (centered at 6.6+12.3 pA).

Data for mixed solutions of nucleosides is provided in FIG. 21. Reads with mixed. films were somewhat heterogeneous, indicative of phase separation on the surface. The distributions shown in FIG. 3F and FIG. 3H, FIG. 5C and FIG. 21 were obtained by sampling the surface at six different points and adding the data. For a bulk dA:dG concentration ratio of 0.24 (Table 1) the ratio of measured peak areas is 0.6, suggesting that dA binds the surface with greater affinity than dG. When the bulk concentration ratio is changed to dA/dG=0.12, the ratio of the peak areas falls only to 0.4, indicative of a complex adsorption isotherm for the mixture.

For a bulk dT:dC concentration ratio of 0.19 (Table 1) the ratio of the areas of the respective peaks indicates a surface concentration ratio 1.1, suggesting that dC has a much higher affinity for this surface. When the concentration ratio is changed to 0.09:1 (FIG. 21) the integrated peak areas indicate that the surface concentration ratio has changed to dT/dC=0.2.

Thus in the case of the dC/dT mixed layers, much larger changes in relative surface concentration result from a given change in the bulk concentrations than is the case for the dA/dG mixtures, presumably a consequence of competition between different solvent affinities, different surface affinities and interactions between the nucleosides on the surface. Nonetheless, the peak associated with the diminished component is consistently lowered, validating our peak assignments based on current measurements on pure nucleoside solutions.

2.6 Calculations of Conductance for Hydrogen-Bonded Complexes

The evaluation of the current due to the applied bias is determined using ballistic transport theory. The electronic states of the gold leak out across the molecules producing a tunneling current. In-elastic scattering of the electrons during their transmission is not considered. The electronic current is determined by the transmission function through the molecules by electrons at the Fermi level of the metal. Only very small biases are considered (+/−0.1 V). In this region the 1-V characteristics were all linear, so that the results are characterized simply by its conductivity. The conductivity amounts to the product of the quantum of conductance and the transmission function at the Fermi level.

The computation of the transmission function is given by standard results from scattering theory (J. K. Tomfohr, O. F. Sankey, J. Chem. Phys. 120, 1542 (2004)), $\Gamma(B)=\text{Tr}(\Gamma_L(E) G_M(E)\Gamma_R(E)G_M^T(E))$, where E is the energy (Fermi level of the gold contacts), 1 are the spectral density of states of the left and right metals contacts, and $G_M$ is the molecular Green's function propagator. The 1 functions contain all the information the metallic states and how they couple to the molecules and $G_M$ contains all the information on the electronic states within the molecules. The Green's function propagator will decay approximately exponentially with distance along the path from metal contact to metal contact.

In order to compute the spectral density of states and Green's functions, one needs a model of the electronic states and methods to model the semi-infinite metallic leads. We modeled both the tip and the substrate and semi-infinite flat planar gold (111) surfaces.

The connecting sulfur atoms at the termini of the molecules are above Au hollow sites. A supercell slab geometry is used. This means the system is a periodic array of Au slabs (initially thin) with molecules sandwiched between them in a specific configuration. The repetitive supercell structure is so that Bloch's theorem can be used to determine the electronic states of the entire system. The electronic structure of the entire supercell is determined self-consistently within density functional theory. To correct for the fact that the slabs are 5-7 layers of Au, a recursion method extends them to infinity by choosing the central layer to represent bulk gold.

The electronic structure is determined using local atomic orbitals of the fireball (O. F. Sankey, D. J. Niklewski, *Phys. Rev.* 840, 3979 (1989)) type. The local orbitals have a finite radius and are thus very slightly excited from the ground state. The SIESTA code (P. Ordejon, E. Artacho, J. M. Soler, *Phys. Rev. B* 53, I 0441 (1996)) is used within density functional theory. All atoms are described with pseudopotentials which eliminates all the core states. The basis set used is double zeta plus polarization (DZP) for all atoms except Au which used a single zeta plus polarization (SZP).

Many different geometries of binding between the two readers and the target base were explored. In all cases the relaxed OFT geometry of the reader and base was used. A restricted set of calculations relaxed the entire molecular system. The results reported in Table 3 used geometries of relaxed individual molecules, and the individual molecules were then rigidly translated into the assembled structures in FIG. 1 A-D. The important variables were the length of the hydrogen bonds (which were set to expected values for such hydrogen bonded molecules e.g. from experiment and DFT (M. H. Lee, O. F. Sankey, *Phys. Rev. E* 79, 051911 1 (2009)), and the distance between the metal leads. The estimated metallic lead distance was set to that value estimated from the tunneling decay constant and the background tunneling current though the solvent.

The quantitative disagreement between theory and experiment (Table 3) appears large—especially so for the case of dT. However, neglect of solvent-mediated tunneling probably ignores an important additional current, equivalent to that detected with just one functionalized electrode where the top contact is solvent mediated. This is a significant current that should be added as a background to the through-bond values calculated here. A second source of error probably originates in our estimate of the tunnel gap. A small overestimate (0.1 nm out of 2.5) would lead to a significant lowering of the calculated tunnel current, because of the very large electronic decay constant for stretched hydrogen bonds. M. H. Lee, O. F. Sankey, *Phys. Rev. E* 79,051911 1 (2009).

Example 3: Tunneling Measurements

We carried out tunneling measurements on a PicoSPM scanning probe microscope (Agilent, Chandler) interfaced to a digital oscilloscope. When both the probe and a gold (II I) substrate were functionalized with 4-mercaptobenzoic acid, the tunneling background signal in TCB was relatively noise free for set-points currents, $I_{b1}$ of up to 10 pA at 0.5V bias, a conductance of 20 pS (FIG. 2). A nucleoside solution was placed in the liquid cell, and after the polarization current had fallen to a small value we re-engaged the probe at a tunnel current level that had previously given a low-noise background signal. Current spikes were immediately obvious in the tunneling signal (FIG. 15). Because neither the surface concentrations of nucleosides nor the efficiency of molecular capture in the gap are known a priori, we adjusted the concentrations of the nucleoside solutions to give approximately equal "spike rates" in the tunnel gap (Table 3).

TABLE 3

Measured and calculated conductances in a functionalized tunnel junction at $I_{b1} = 6$ pA, V = 0.5 V. Measured values are the average of three independent runs (errors are ±1 sd). Calculated conductances are for the structures shown in FIG. 1 A-D. Read rate is based on counts acquired in a 180 s period for nucleoside concentrations between 0.8 and 4.3 μM. The disparity in the range of values between theory and experiment may reflect neglect of a background contribution via solvent-mediated tunneling into a molecule bound at one electrode. Absolute values will be affected by inaccuracies in the estimate of the gap size.

|  | dT | dG | dC | dA |
|---|---|---|---|---|
| Measured G (pS) | 13.6 ± 0.3 | 18.6 ± 0.9 | 25.3 ± 2.5 | 33 ± 1.9 |
| Calculated G (pS) | 0.04 | 0.12 | 0.51 | 1.05 |
| Read rate ($s^{-1}$) | 7.1 ± 1.4 | 5.5 ± 1.1 | 5.5 ± 1.1 | 6.6 ± 1.3 |

Many of the "spikes" showed the two-level "telegraph noise" characteristic (S. Chang et al., *Nanotechnology* 20, 075102 (2009)) of binding and unbinding of a single molecule in the gap (insets, FIG. 15). The STM servo gains were set so that only spikes of the longest duration were affected by the action of the current-control servo (FIG. 16).

Figure 3A:
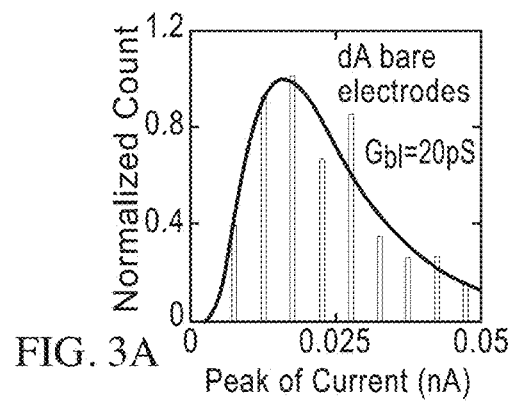
FIGS. 3A-3H shows the exemplary effect of electrode functionalization on the distribution of current spikes for purines. Bare electrodes (FIG. 3A-dA and FIG. 3C-dG) give broad distributions (gap conductance 20 pS, 0.7 µM dA, 2.9 µM dG in TCB). Fits are Gaussian in the log of the current (see FIGS. 18-20). Distributions narrow ten-fold when one electrode is functionalized with 4-mercaptobenzene (FIG. 3B-dA, FIG. 3D-dG) (gap conductance 12 pS, $I_{b1}$=6 pA, V=0.5V). Fits are to two Gaussians in the log of the current with a peak at $i_0$ ("1") and a second at 2 $i_0$ ("2") (see formula III). $i_0$=5.9 pA for dA and 5.6 pA for dG. When both electrodes are functionalized (FIG. 3E-dA, FIG. 3G-dG) the peak currents are clearly different ($i_0$=9.4 pA for dG, $i_0$=16.5 pA for dA).
Figure 3B:
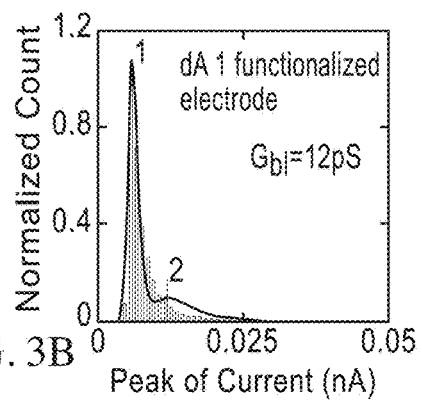
Figure 3C:
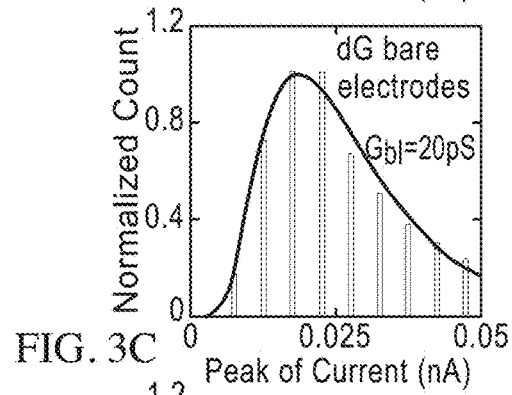
Figure 3D:
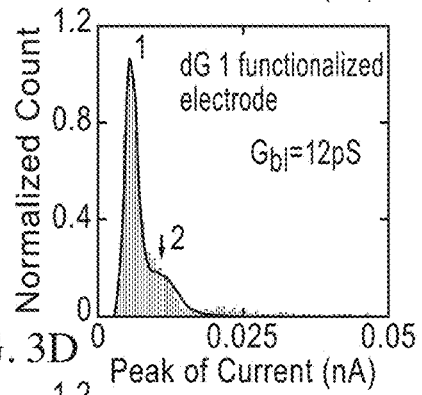
Figure 3E:
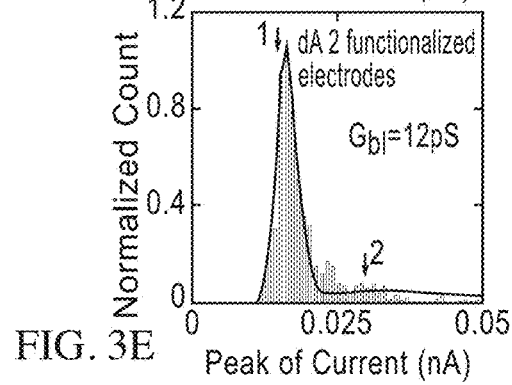
Figure 3F:
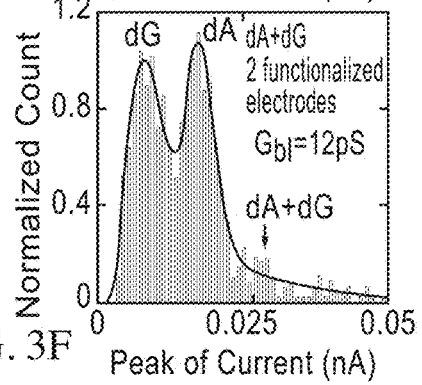
Figure 3G:
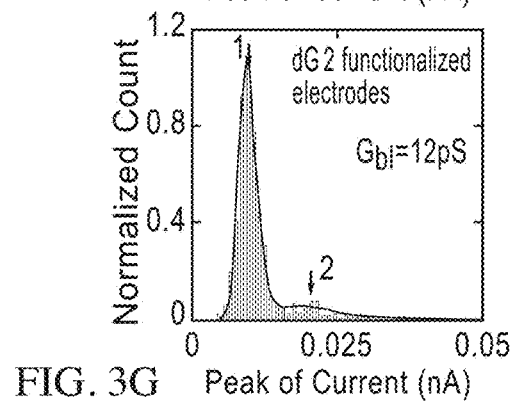
Figure 3H:
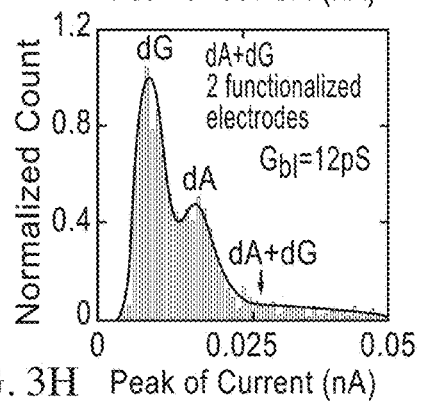
Figure 20:
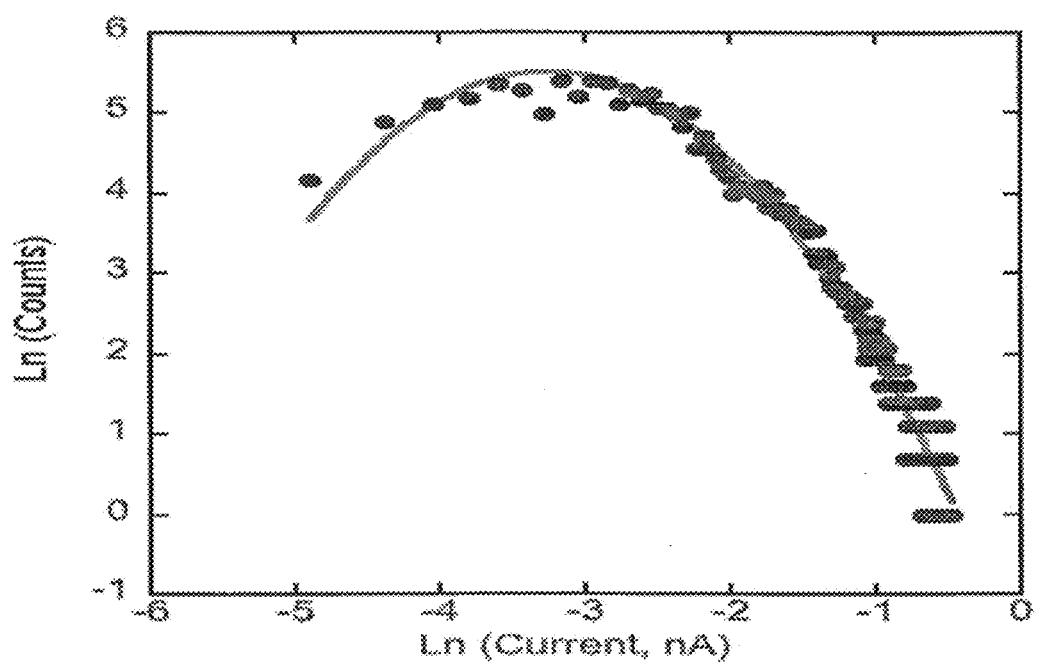
FIG. 20 shows an exemplary parabolic fit (solid line) to the data from FIG. 19A plotted on a log-log plot.
Figure 27A:
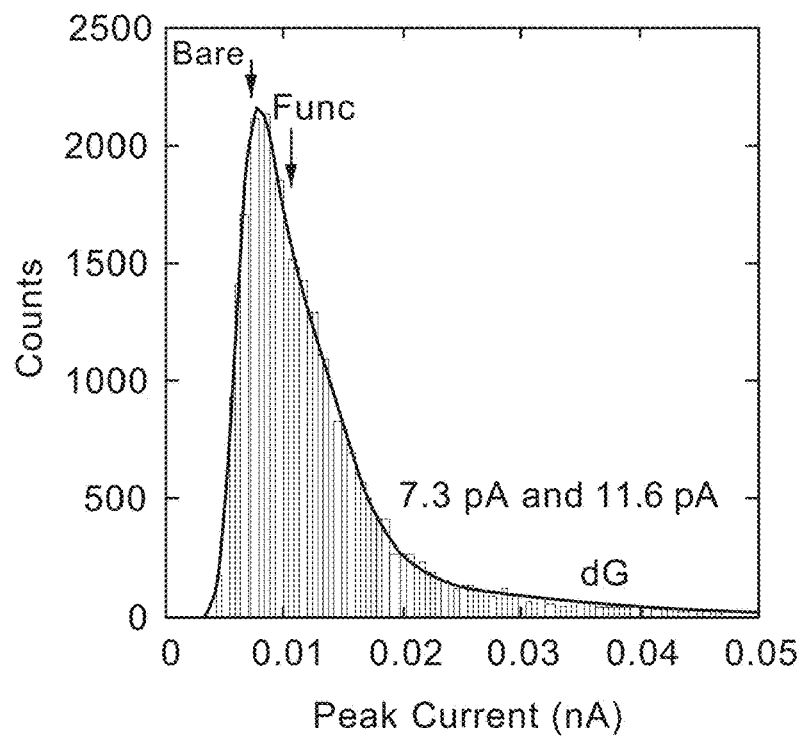
FIGS. 27A-27B show exemplary current distributions obtained by retaining all recorded spikes in an exemplary analysis (FIG. 27A) and by rejecting spikes of only 1 (20 µs) or 2 (40 µs) sample points duration (FIG. 27B). Data are for dG, 2.9 µM, $G_{b1}$=12 pS. Solid curved lines are 2 Gaussian log fits with independent peaks in A, and with peaks fixed at $i_0$ and $2 i_0$ in B. The data in A are dominated by a feature at 7.3 pA, equal to the current recorded with an unfunctionalized probe. The peak in B has moved to 9.7 pA. The distribution reflects the finite frequency response of the STM current-to-voltage converter which will reduces the measured amplitude of fast peaks (see FIG. 29). Similar results were obtained for dC (peak for all data=7.3 pA, peak for filtered data=13 pA). Data for dT were not affected by filtering (peak for all data=7.3 pA, peak for filtered data=6.8 pA).
Figure 27B:
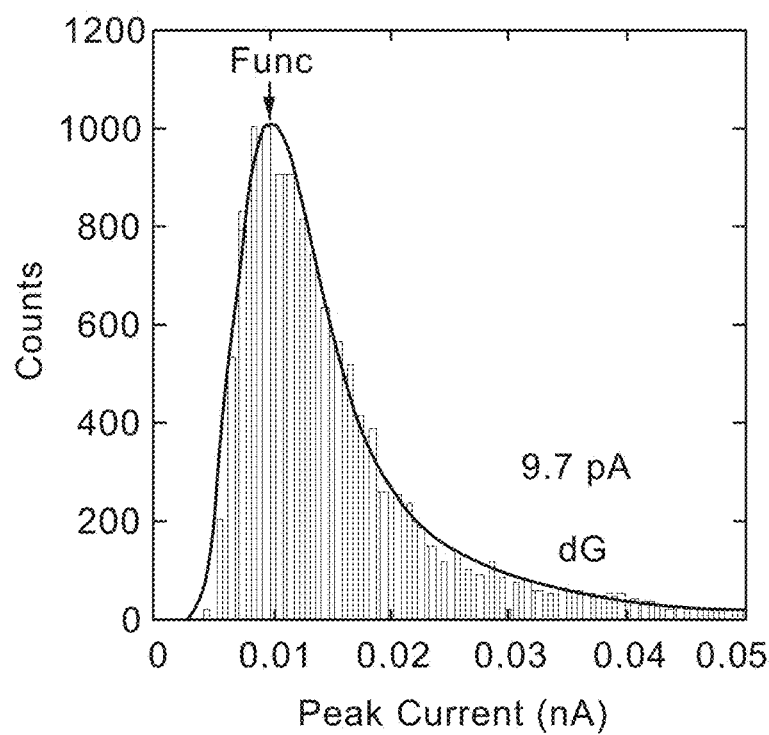
Figure 28A:
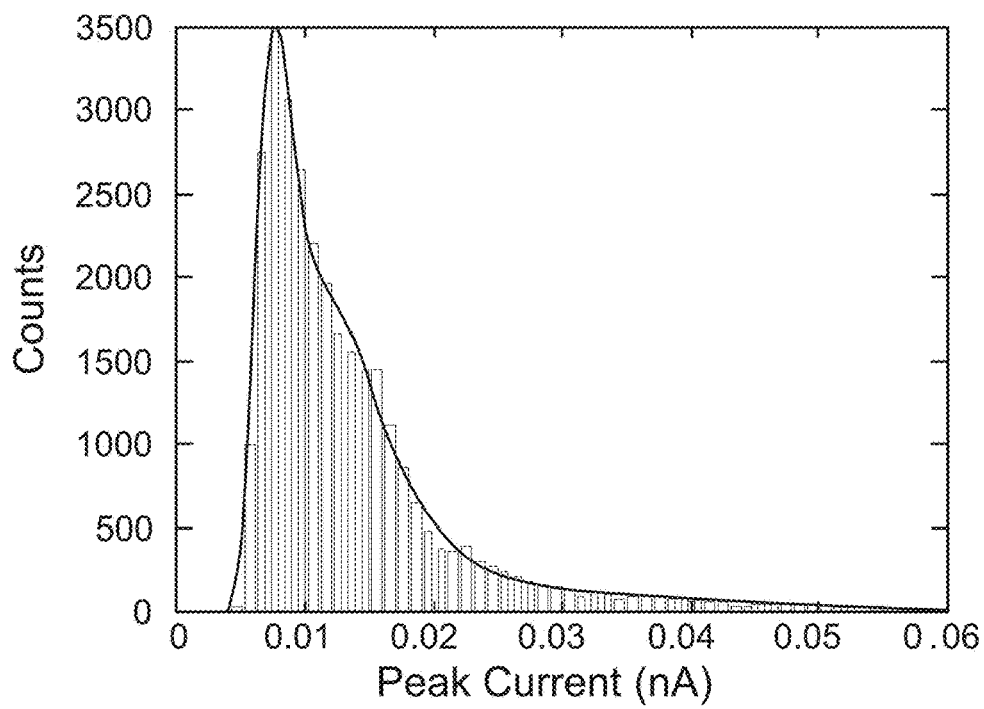
FIGS. 28A-28B provide exemplary current distributions obtained by retaining all recorded spikes in an exemplary analysis for dA (FIG. 28A—all data, FIG. 28B—fastest two points rejected). In this case, a residue of the "single functionalized electrode" peak at 6.5 pA remains when 1 or 2 point spikes are rejected, so the data were fitted with three Gaussian log functions, with two independent peak values ($i_0$, $i_1$ and $2i_1$). The maximum of the distribution moves from 6.5 pA to 15.6 pA when the shortest spikes are rejected. The shape of the distribution depends on the probe used, 2 Gaussian fits working well for other data sets (e.g., FIG. 2) where the "unfunctionalized" peak was almost completely eliminated by rejection of the fastest spikes.
Figure 28B:
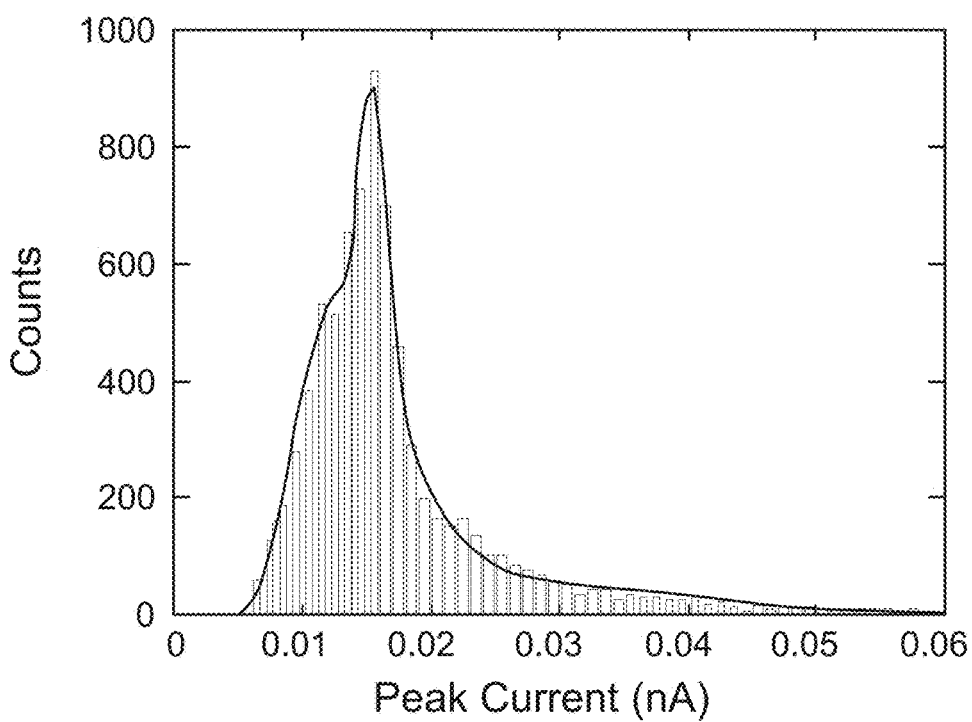
Figure 29A:
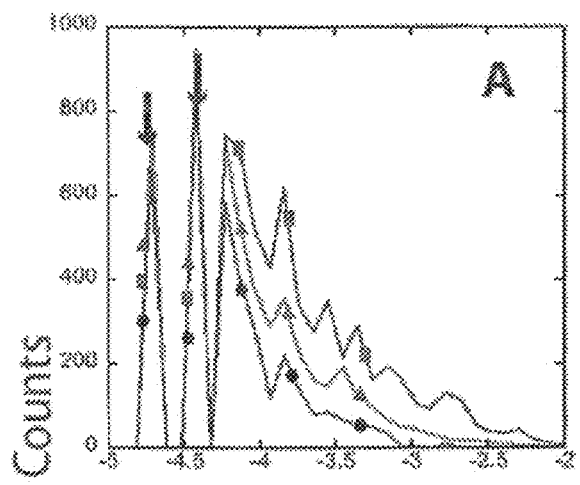
FIGS. 29A-29D shows exemplary distributions of spike lifetimes for dA (FIG. 29A), dC (FIG. 29B), dG (FIG. 29C), and dT (FIG. 29D). Circle lines are for bare electrodes, triangle lines for one functionalized electrode, and square lines are for two functionalized electrodes. Sharp features reflect the data binning. All data are taken at the working concentrations shown in Table 1 and O.SV. $G_{b1}$=20 pS for bare probes and 12 pS for functionalized probes. The arrows point to the spikes of 40 or 20 µs duration that were rejected from the current distributions to enhance selectivity. With the exception of dT, lifetimes are a little longer with two functionalized probes. However, lifetimes for bare probes, or one functionalized probe are essentially identical. Thus the narrowing of the tunneling distribution must reflect a difference in the range of allowed bound geometries between functionalized and bare metal surfaces, and not a difference in bound-state lifetimes. The −3 dB frequency of the current-to-voltage converter is ~7 kHz (143 µS) so faster features are attenuated in the data shown here.
Figure 29B:
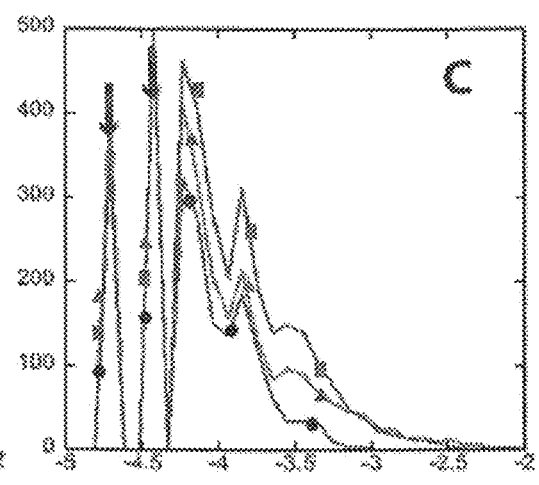
Figure 29C:
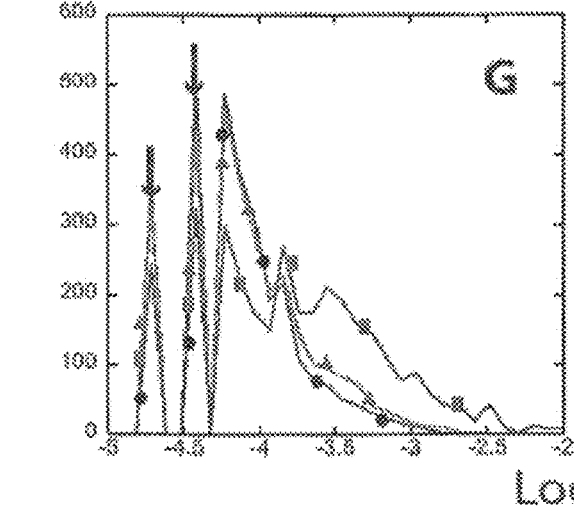
Figure 29D:
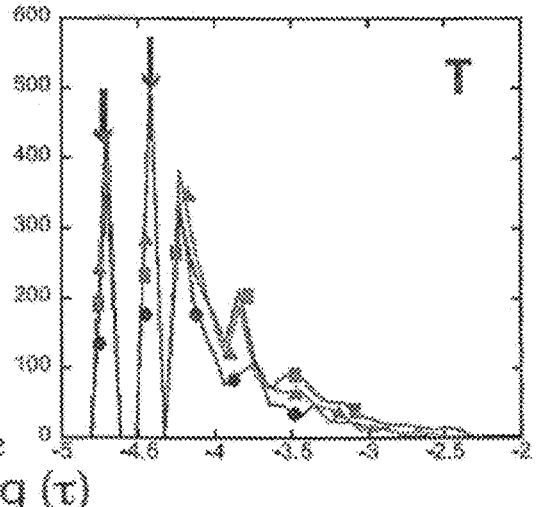

We generated distributions of the peak currents using a custom program to analyze the height of the spikes. The program captures signals two standard deviations above the noise on the baseline, and also rejects data of only one or two points in time (i.e. up to 40 μs duration). The effect of the choice of filtering parameters on the measured distribution is shown in FIG. 17 and FIGS. 27-28). FIG. 3 shows how these measured distributions are affected by functionalization of the electrodes. Distributions recorded with bare electrodes are shown in FIG. 3A and FIG. 3C. In order to record signals with bare electrodes, we had to reduce the tunneling gap a little by operating at a conductance of 20 pS. Even at this smaller gap, reads with bare electrodes on the pyrimidine nucleosides were much less frequent than reads on purine nucleosides (FIG. 18, Table 2). The measured current distributions were fitted quite well by a Gaussian distribution of the logarithm of the currents (solid lines) as shown in FIGS. 18-20. The fitted peak currents differ for these two nucleosides (15.9±0.4 pA for dA and 18.7±0.2 pA for dG) but the difference (2.8 pA) is less than the width of the distribution on the high current side (~15 pA). When measurements are repeated with a functionalized substrate and a bare gold probe at an increased gap (corresponding to 12 pS) the distribution of measured currents narrows by an order of magnitude (FIG. 38—dA), (FIG. 3D—dG) but the peak currents are not significantly different. The distribution of spike lifetimes is quite similar for both bare electrodes and for one functionalized electrode (FIG. 29). Thus, it appears likely that the spikes observed with bare electrodes correspond to transiently bound states of the nucleosides also. If this is the case, then the narrowing observed with a functionalized electrode must be a consequence of a reduction in the number of types of bound states in the tunnel gap. When both probe and substrate are functionalized, (FIG. 3E—dA, FIG. 3G—dG), the peak current for dA is clearly higher than the peak current for dG. Thus distinctive signals can be generated when both electrodes are functionalized, but do they originate with single nucleosides? The "telegraph noise" signals are characteristic of single-molecule reads and the small size of the peaks assigned to two-molecule reads ("2" in FIG. 3B, FIG. 3D, FIG. 3E, FIG. 3G) suggests that reads of more than one molecule at a time are infrequent. However, electrochemical leakage currents can introduce current errors that depend on the nucleoside so the measured current may not be generated from single molecule currents alone. A better test of the fidelity of tunneling reads can be carried out using mixtures of two nucleosides so that any errors owing to an electrochemical background are present in both sets of signals. FIG. 3F shows the current distribution obtained with a mix of dA and dG. The higher current peak is at essentially the same current as recorded for dA alone, and thus should count the dA molecules in this mixture. This assignment is confirmed by halving the concentration of dA in solution (FIG. 3H). Surface concentrations are unknown a priori and dependent on competition between nucleosides for surface binding sites and the different dissociation rates back into solution so absolute signal rates cannot be interpreted in terms of concentrations quantitatively. Most of the data in this panel were well fitted assuming single molecule reads with only 5% of the reads consistent with both dA and dG in the gap at the same time ("dA+dG", FIG. 3F).

Figure 5A:
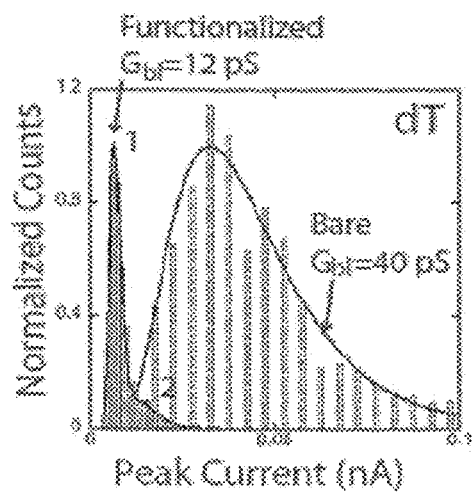
FIGS. 5A-5C show the exemplary effect of electrode functionalization for pyrimidine reads. For reads with bare electrodes (broad distributions in FIGS. 5A and 5B) $G_{b1}$ was increased to 40 pS to increase the count rate. The narrow distributions in SA and 58 are taken with both electrodes functionalized and yield $i_0$=6.7 pA for dT and 13.3 pA for dC ($G_{b1}$=12 pS. $I_{b1}$=6 pA. V=0.5V). In a mixed solution, (FIG. 5C) the dT peak occurs at 8 pA and the dC peak occurs at 13.4 pA, an assignment verified by measuring a mixture with half the concentration of dT (FIG. 21).
Figure 5B:
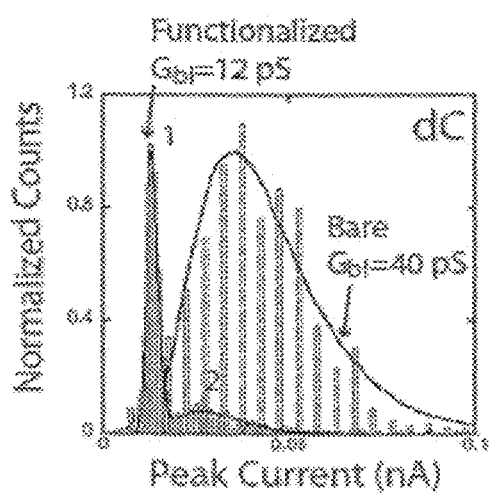
Figure 5C:
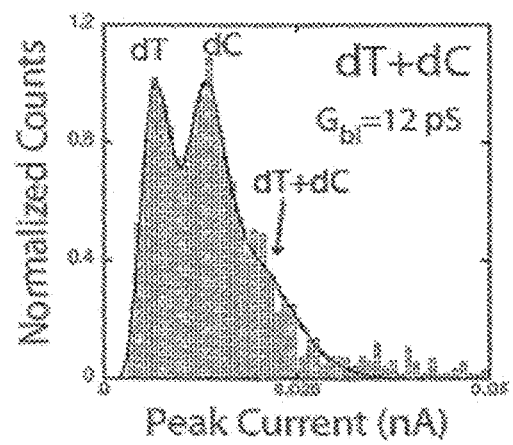

The same types of features are observed for dC and dT (FIG. 5 and FIG. 29) but the data for a bare gap and bare substrate had to be collected at a yet larger tunnel current (20 pA, corresponding to 40 pS) in order to acquire a significant number of reads for the (smaller-sized) pyrimidine nucleosides (FIG. 19). dC and dT are also clearly separated in a mixed sample when read with probes that are functionalized (FIG. 5C and FIG. 21).

Figure 22A:
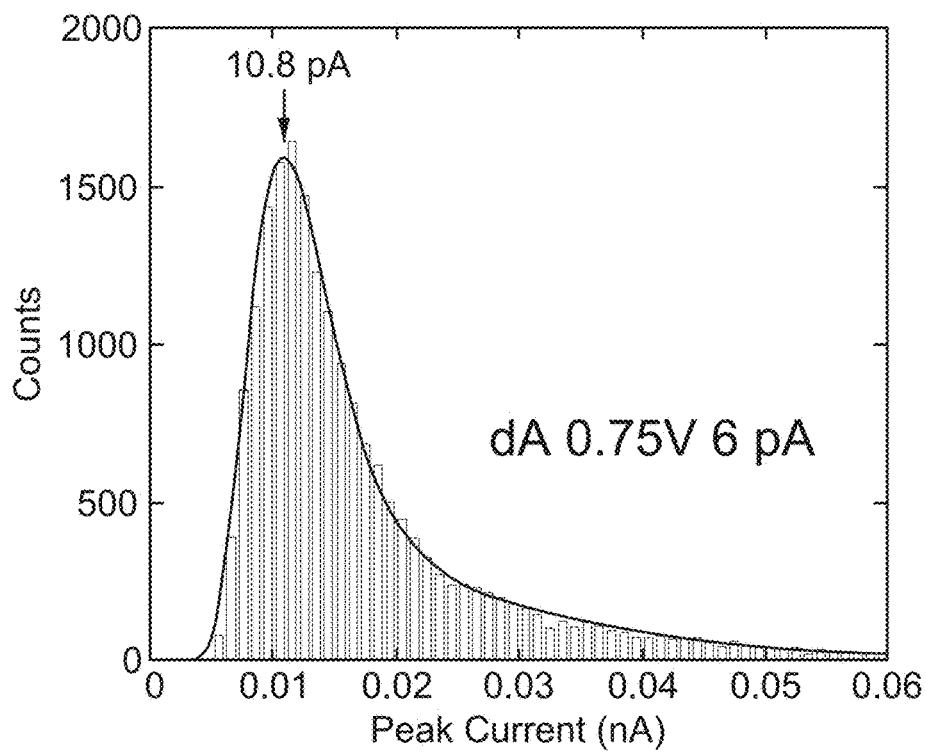
FIGS. 22A-22B provide exemplary current distributions measured at $1_{b1}$=6 pA with a bias of 0.75V ($G_{b1}$=8 pS) resulting in a larger gap for dA (FIG. 22A) and for dC (FIG. 22B). The molecular conductances are reduced as expected (G(dA)=14.4 pS, G(dC)=15.6 pS). The reduction for dA is greater than would be predicted by the fit shown in FIG. 7A. This indicates that there is a bias dependence in addition to the exponential dependence on gap size. Data taken as a function of bias at a fixed gap size (See FIG. 23) tend to confirm this trend.
Figure 22B:
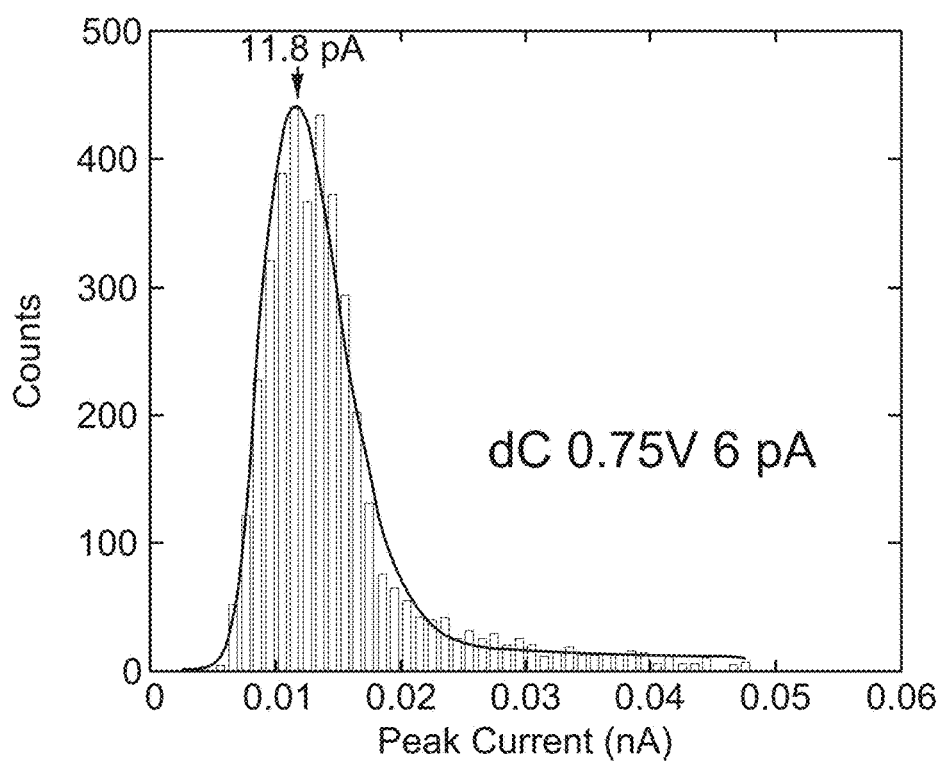
Figure 23:
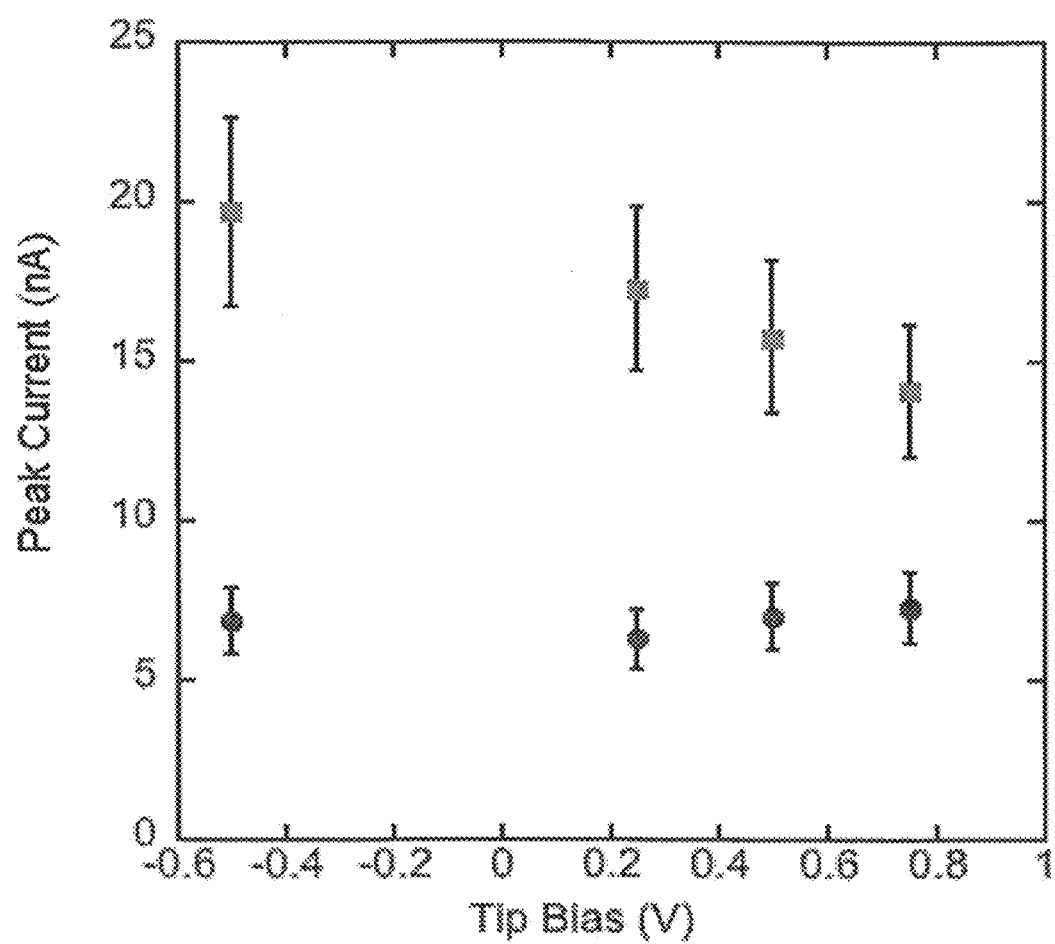
FIG. 23 provides exemplary peak currents for dA as a function of bias at a constant gap conductance (12 pS; 0.75V, 9 pA, 0.5V, 6 pA and 0.25 V 3 pA). The circles are data taken with one bare gold electrode, and they show little dependence on bias. Data taken with 2 functionalized electrodes (squares) show that peak current increase as bias is lowered. Altering the sign of the bias does not lead to large changes (datum at −0.5 V).
Figure 24:
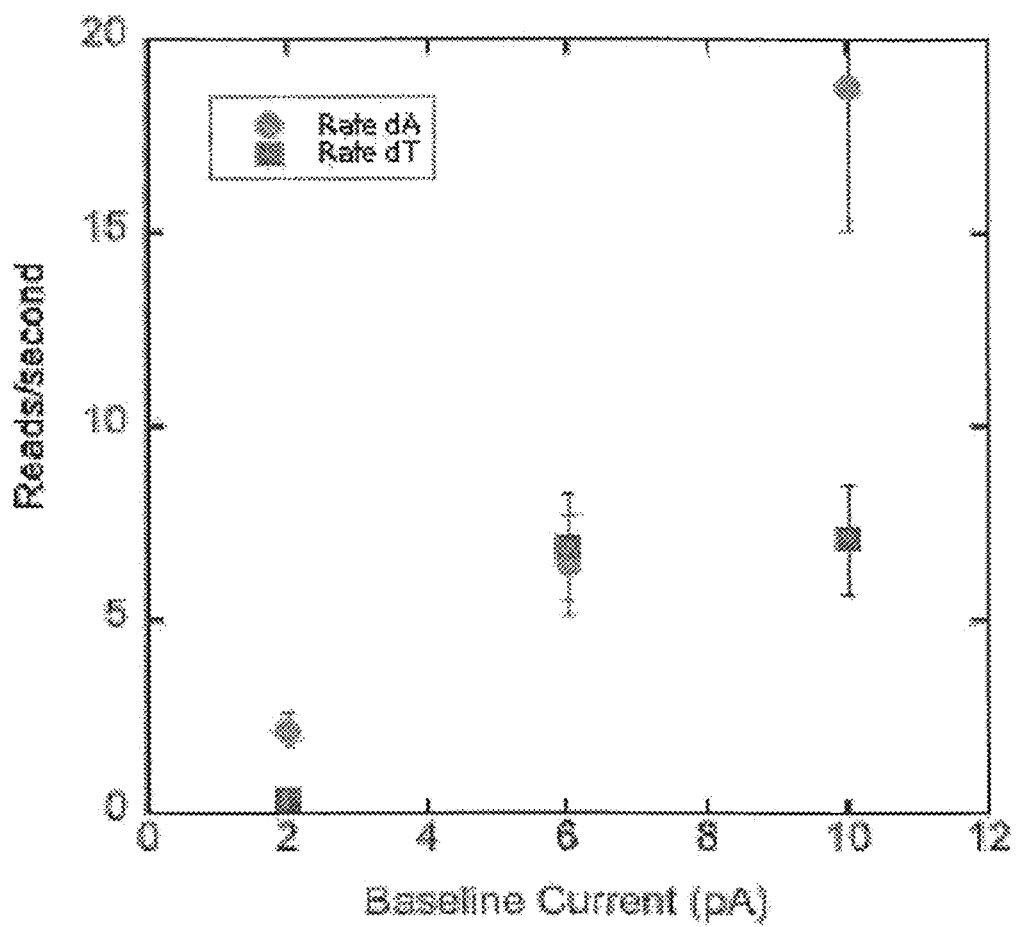
FIG. 24 shows exemplary reads per second with functionalized probes obtained by averaging data obtained over 180 s for dA (circle) and dT (squares) as a function of the baseline tunneling current. These data are somewhat dependent on probe geometry, an effect reflected in error bars obtained by comparing data taken with two different probes.
Figure 25:
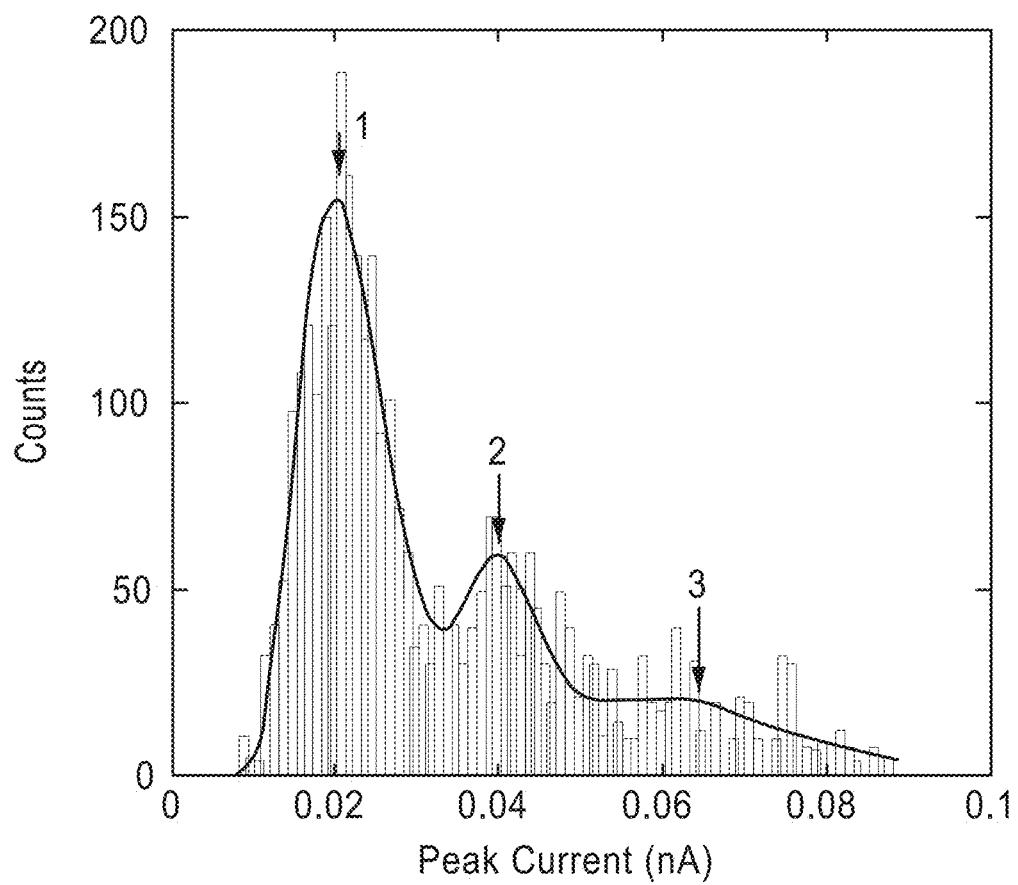
FIG. 25 shows exemplary current distribution (functionalized probes) obtained at $G_{b1}$=20 pS for dA showing evidence of 2 and even 3 molecule reads.

At a given bias, the absolute value of peak current is directly proportional to the baseline conductance of the gap (FIG. 7A), i.e., it increases exponentially as the gap is decreased, similar to what has been reported for other hydrogen-bonded systems in large tunnel gaps (S. Chang et al., *Nanotechnology* 20, 075102 (2009)). We found evidence of an interesting dependence of the peak currents on bias at a fixed gap size (i.e., gap conductance) (FIG. 22) indicating the possibility of a non-linear current-voltage dependence for molecules bound to both electrodes. The read frequency also increased as the gap was narrowed (FIG. 24). On the other hand, the fraction of multi-molecule reads increased rapidly in smaller gaps (FIG. 7A and FIG. 25) so 12 pS appears to be an optimal value for the baseline conductance at a bias of 0.5V.

Figure 26:
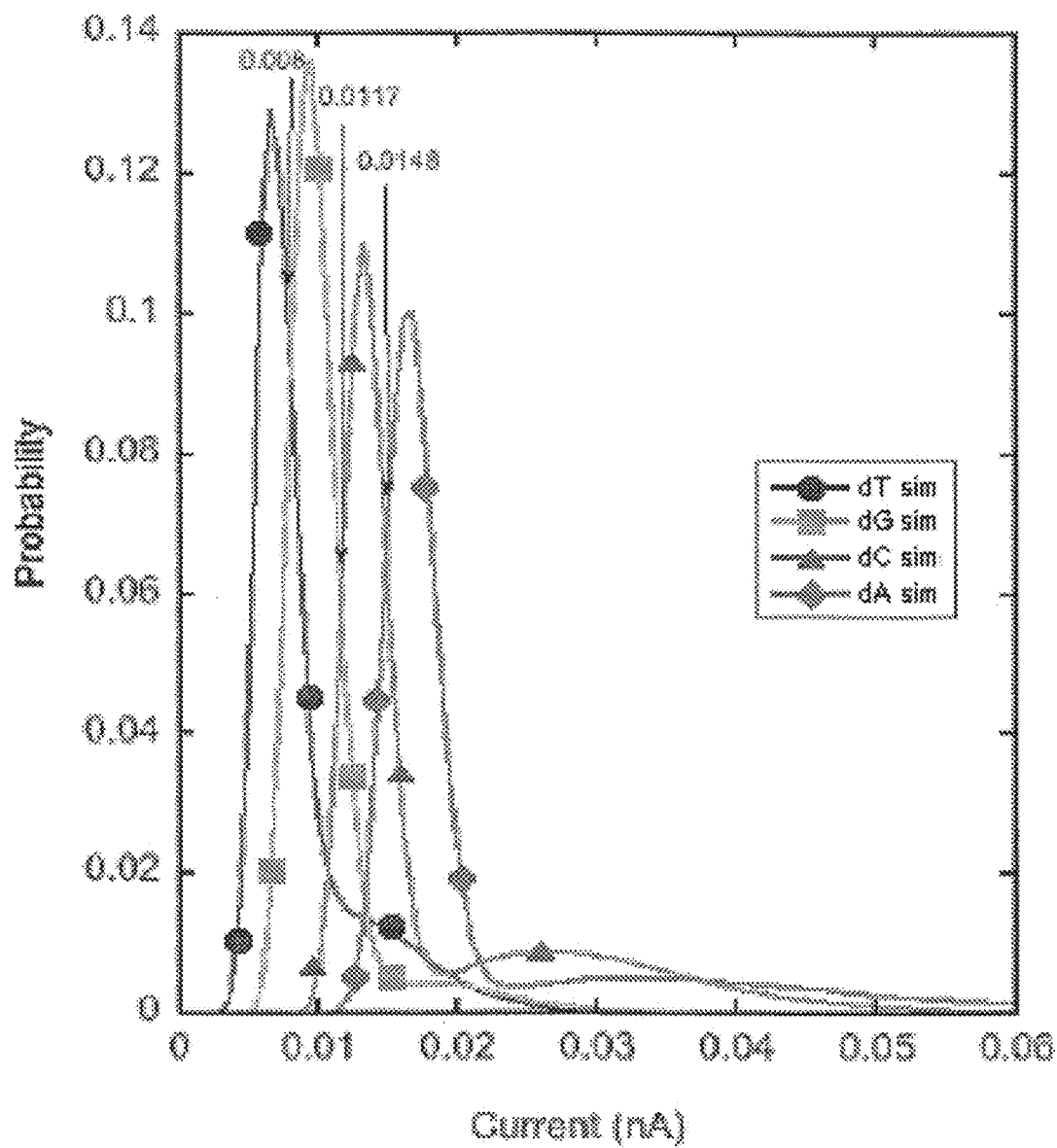
FIG. 26 shows exemplary fitted distributions to sets of experimental data (including the 2 molecule read peaks) for dT (circle), dG (square), dC (triangle) and dA (diamond) for $I_{b1}$=6 pA, V=0.5V. (peaks left to right: dT, dG, dC, dA). Setting discrimination levels at the values shown (8 pS, 11.7 pS and 14.8 pS) yields a 72% probability for dT if i<8 pA, 64% probability for dG (8 pA<i<11.7 pA), 61% for dC (11.7<i<14.8 pA) and 60% for A (i>14.8 pA).

Values for the peak currents measured at $I_{b1}$=6 pA, V=0.5V are summarized by the cross-hatched bars in FIG. 78. These are the results of three different runs (one carried out, from sample preparation to data analysis, by a different team) on each of the four nucleosides. The peaks for each nucleoside are separated by an amount comparable to the width of the distribution, allowing the fraction that are single-molecule reads with two "good" contacts to identify the base with p≥0.6 (FIG. 26).

Figure 7B:
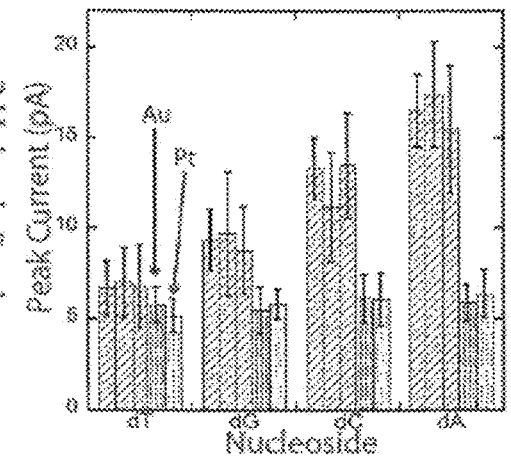
Figure 7C:
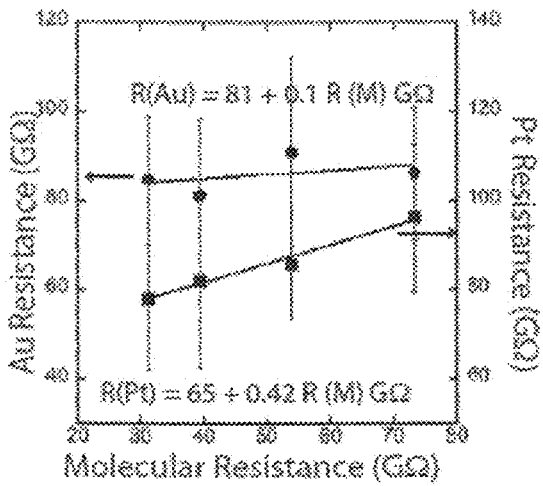

We also recorded data with a functionalized substrate and a bare Au (dark shaded bars) or bare Pt (light shaded bars) probe. The peak currents change little from nucleoside to nucleoside, an expected consequence of the resistance, $R_c$, associated with bare contacts (X. D. Cui et al., *Science* 294, 571 (2001)) although the lack of selectivity is not accounted for by contact resistance alone. If we assume that reads with two functionalized probes determine a resistance for a single molecule, $R_m$, then the resistance of a junction with one bare electrode should be given by $R_j=R_c+R_m$, FIG. 7 B shows that the signal with one bare gold electrode is insensitive to the molecular resistance, while a bare Pt electrode is about half as sensitive as the simple "resistors in series" model predicts, probably reflecting the way in which binding to the electrodes affects the position of molecular states (V. Meunier, P. S. Krstić, *J. Chem. Phys.* 128, 041103 (2008)).

At 12 pS conductance, we estimate the gap to be about 2.5 nm, using $G=G_0\exp(-\beta x)$ where $G_0$ is the quantum of conductance (77 μS) and $\beta=6.4$ nm$^{-1}$ (J. He, L. Lin, P. Zhang, S. M. Lindsay, *Nano Letters* 7, 3854 (2007)). FIGS. 1 A-D show what we believe to be the most likely hydrogen bonded (energy-minimized) structures for the four nucleosides in a gap with both electrodes functionalized. We carried out density functional calculations of the conductance of these four molecular junctions and the predicted conductances are listed below the measured values in Table 3. The predicted order of conductance agrees with experiment, though the absolute values are significantly lower, possibly because of an overestimate of the size of the tunnel gap. Lifetime data (FIG. 29) for dT show little change when both electrodes are functionalized, so the dT spikes may represent solvent-mediated tunneling at one electrode. Since solvent molcules are not included in the simulations, this additional tunneling contribution is absent from the predictions. Accordingly, a constant background should be added to each of the predicted currents, which would diminish the discrepancy between the range of predicted and measured currents.

Example 4: Synthesis of 4-Mercaptobenzamide

The synthesis of 4-mercaptobenzamide was carried out according to the following scheme:

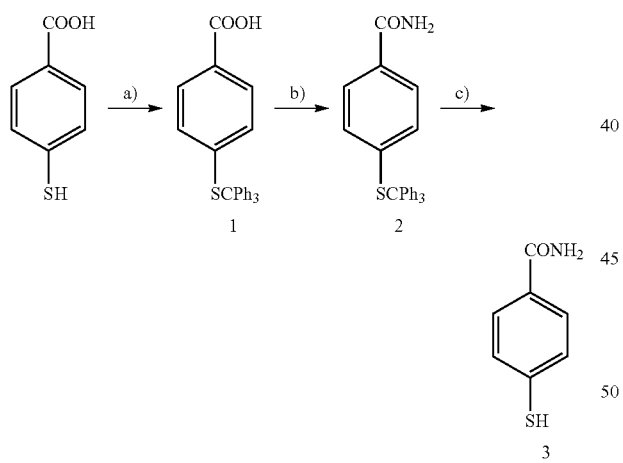

4.1 Materials and Methods

Proton NMR (1H) spectra were recorded at 400 MHz on a Varian 400 MHz spectrometer or at 500 MHz on a Varian 500 MHz spectrometer, and carbon NMR (13C) spectra were recorded at either 100 MHz on a Varian 400 MHz spectrometer or at 125 MHz on a Varian 500 MHz spectrometer. HRMS spectra were acquired using the atmospheric pressure chemical ionization (APCI) technique. Flash chromatography was performed in CombiFlash Rf (Teledyne Isco, Inc.). All reagents were purchased from Aldrich unless other\vise stated.

4.2 Step 1: 4-Tritylmercaptobenzoic acid

4-Mercaptobenzoic acid (1.54 g, 10 mmol) and trityl chloride (2.79 g, 10 mmol) were dissolved in DMF (25 mL) and stirred at an ambient temperature for 36 h. The solvent was removed under reduced pressure. The residue was dissolved in chloroform (50 mL), and washed with water (3×25 mL). The organic layer was dried over MgSO4, filtered, and concentrated. Compound 1 was obtained as a white solid (3.20 g, 81%). 1H NMR (500 MHz, CDCl3): 7.67 (d, 2H), 7.21-7.39 (m, 15H), 6.99 (d, 2H).

4.3 Step 2: 4-Tritylmercaptobenzamide

Ammonia (0.5 M in dioxane, 1 mmol) was added dropwise to a solution of compound 1 (198 mg, 0.5 mmol), 1-hydroxy-benzotriazole (HOBt) (68 mg, 0.5 mmol), and 1,3-dicyclohexylcarbodiimide (DCC) (103 mg, 0.5 mmol) in THF (5 mL) at 0° C. The resulting mixture was allowed to warm to room temperature, stirred for 24 h. After filtration, the filtrate was washed with saturated aqueous NaHCO3. The organic layer was dried over MgSO4, filtered, and concentrated. The residue was purified by flash chromatography (silica gel, Dichloromethane: Methanol gradient 100:0 to 100:3) to yield compound 2 as a white solid (154 mg, 78%). 1H NMR (400 MHz, CDCl3): 6.98-7.43 (m, 19H), 5.95 (brs, 1H), 5.75 (br s, 1H); HRMS (APCI+): found, 396.1442; calcd for C26H22NOS+H, 396.1422.

4.4 Step 3: 4-Mercaptobenzamide

Compound 2 (60 mg, 0.15 mmol) was dissolved in a mix of trifluoroacetic acid (TFA) (2 mL) and triethylsilane (TES) (2 mL), stirred for 2 hat room temperature. The solution was rotarily-evaporated to dryness under reduced pressure. The residue was crystallized from the mixture of hexanes and dichloromethane (v:v=1:1) to yield compound 3 as a white solid (12 mg, 52%). 1H NMR (500 MHz, CDCl3): 7.68 (d, 2H), 7.31 (d, 2H), 6.50 (br s, 1H), 6.29 (br s, 1H), 3.61 (s, 1H); 13C NMR (125 MHz, CDCl3): 169.9, 138.0, 129.4, 128.5, 128.2. 4 HRMS (APCI+): found, 154.0326; calcd for C7H7NOS+H, 154.0326.

Figure 30:
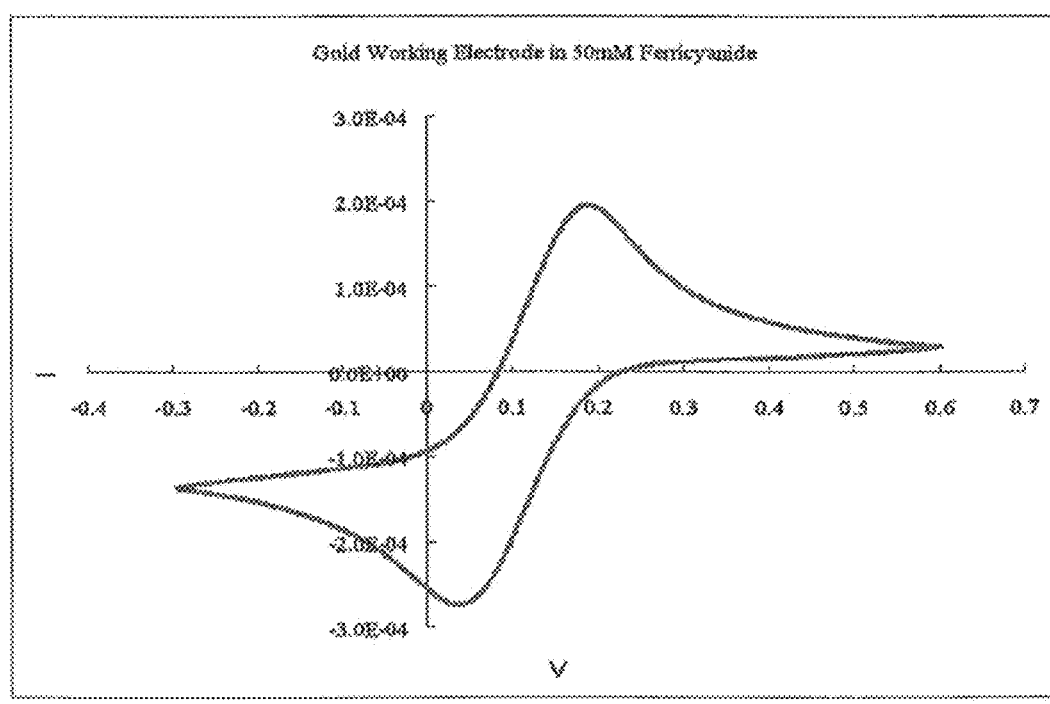
FIG. 30 illustrates cyclic voltammetry for an exemplary bare gold wire in 50 mM potassium ferricyanide (potential vs. Ag wire).
Figure 31:
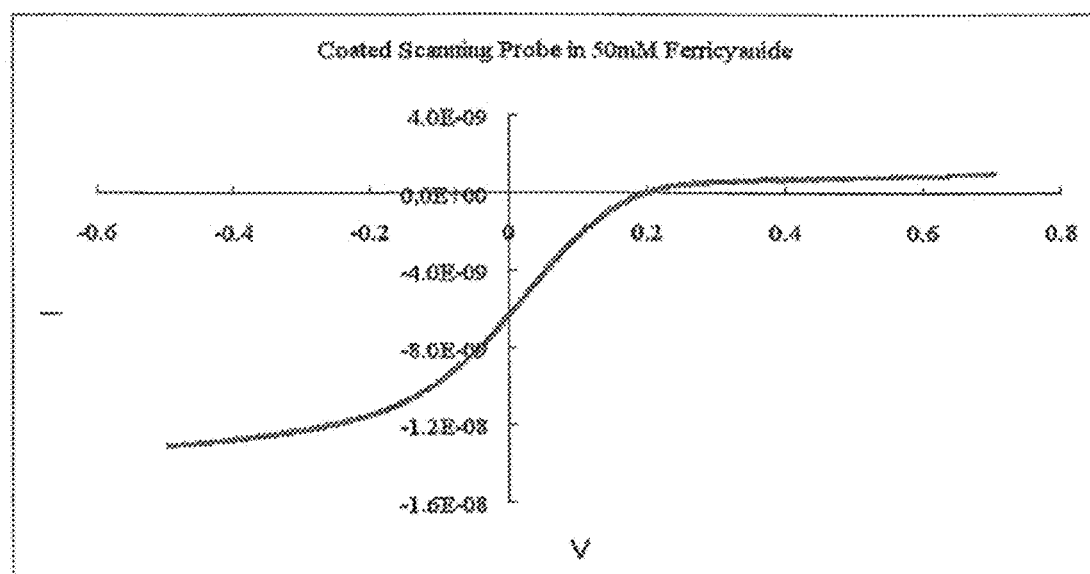
FIG. 31 illustrates cyclic voltammetry for an exemplary HOPE coated STM tip. Assuming a hemispherical exposed tip shape and using the formula $l_{max}=2\pi RnFCD$, the exposed surface area of coated scanning probes is on the order of $10^{-2}$ µm$^2$.

Example 5: Production, Functionalization, and Characterization of Electrodes 5.1 Electrode Production Gold tips were electrochemically etched from gold wires (Aesar 99.999% pure) using a mix of HCl and Ethanol (volume ratio 1:1). Only sharp tips (judged by optical microscopy with 300× magnification) were selected for the insulating process. High Density Polyethylene (HDPE) was used as insulation. Prior to insulation, gold tips were cleaned with piranha (mixture of oxygen peroxide and sulfuric acid, volume ratio of 1 to 3—Caution—this material can explode in reactions with organic materials) for 1 min to get rid of organic contaminations and rinsed with double distilled water, ethanol and blown dry with compressed nitrogen gas. During insulation, the HOPE was melted at 250 C° on a homemade tip coating instrument. Penetration through the melted HOPE will cover most area of the tip with the insulating material, leaving only the apex un-insulated. The exposed surface area of insulated tips was characterized by cyclic voltammetry in potassium ferricyanide. Insulated and un-insulated tips were tested for cyclic voltammetry. The insulated tip provided for a more consistent and regular electrode. FIGS. 30 and 31 illustrate these results. FIG. 30 shows cyclic voltammetry for a bare gold wire in 50 mM potassium ferricyanide (potential vs. Ag wire). FIG. 31 shows cyclic Voltammetry for a HOPE coated STM tip. Assuming a hemispherical exposed tip shape and using the formula Imax=2πRnFCD, the typical exposed surface area of the coated scanning probes is on the order of 10-2 μm.

5.2 Functionalization

Gold substrates were annealed in a hydrogen flame to get rid of contamination and form well ordered Au surfaces. 4-Mercaptobenzamide prepared according to Example 4 was dissolved (1 mM) in methanol and degassed using argon to avoid oxidation of thiols. The insulated tips treated substrates were immersed in this solution for >2 hours. This resulted in the formation of monolayers of benzamide on the surface. Extended functionalization times degraded insulation on the probes so treatment of probes was limited to 2 h. Functionalization of gold substrates was carried out for up to 20 hours.

The thickness of the molecule SAM after deposition was measured by ellipsometry (Gaertner, Skokie, Ill.) at a wavelength of 632.8 nm with an incident angle of 70 degrees. The optical constants of the freshly hydrogen-flamed bare gold substrate (200 nm thick on mica) were measured before deposition of molecules given n=0.2 and k=−3.53. The SAM optical constants were set to nf=1.45 and kf=0. The thickness of 4-mercaptobenzamide monolayer was measured as 0.70±0.17 nm.

Figure 32:
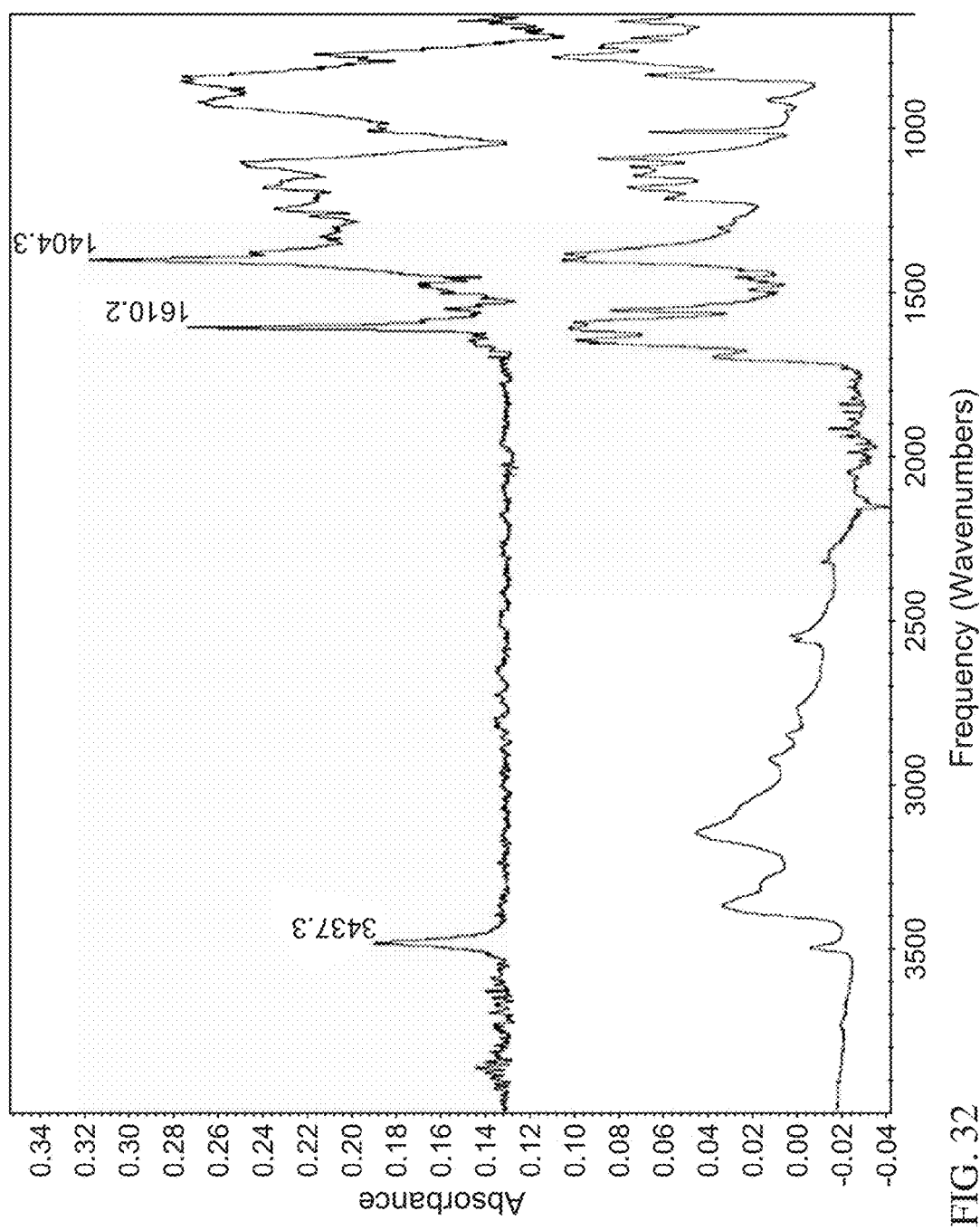
FIG. 32 illustrates exemplary FTIR spectra of 4-mercaptobenzamide monolayer (lower line) and powder (upper line).

Infrared absorption spectra of the SAM were recorded using the Smart Apertured Grazing Angle accessory on Thermo Nicolet 6700 FTIR (Thermo Fisher Scientific, MA). The spectrum of the powder sample was taken using Smart Orbit (a diamond single-bounce ATR accessory). FIG. 32 shows FTIR spectra of the 4-mercaptobenzamide monolayer (lower line) and powder (upper line). In the monolayer IR, absorption peaks at 3487 cm-1, 1610 cm-1, and 1404 cm-1 are assigned as N—H stretching of discrete NH2 (without hydrogen bonds), amide band I, and amide band II, respectively.

Figure 33:
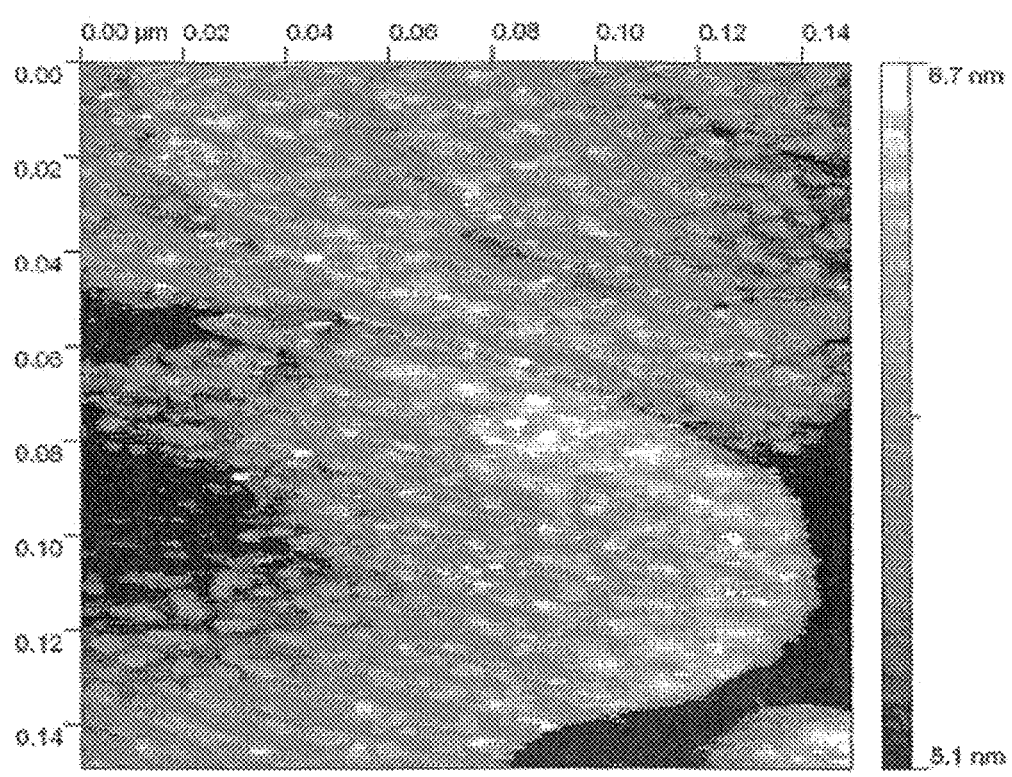
FIG. 33 is an STM image showing islands of mercaptobenzamide on an Au surface. Image in 1 mM PB buffer with a gold tip, 0.5 V tip bias with 10 pA set point.

The ellipsometry data suggested almost a full monolayer coverage, however, STM images showed (FIG. 33) that the coverage occurs in patches. The read rates recorded in the paper are for reads taken with the probe positioned over functionalized patches. In FIG. 33, the STM image shows islands of mercaptobenzamide on Au(111) surface. (Image in 1 mM PB buffer with a gold tip, 0.5 volts tip bias with 10 pA set point.)

5.3 Imaging the Electrodes

Figures 34A, 34B, 34C, 34D, 34E, 34F:
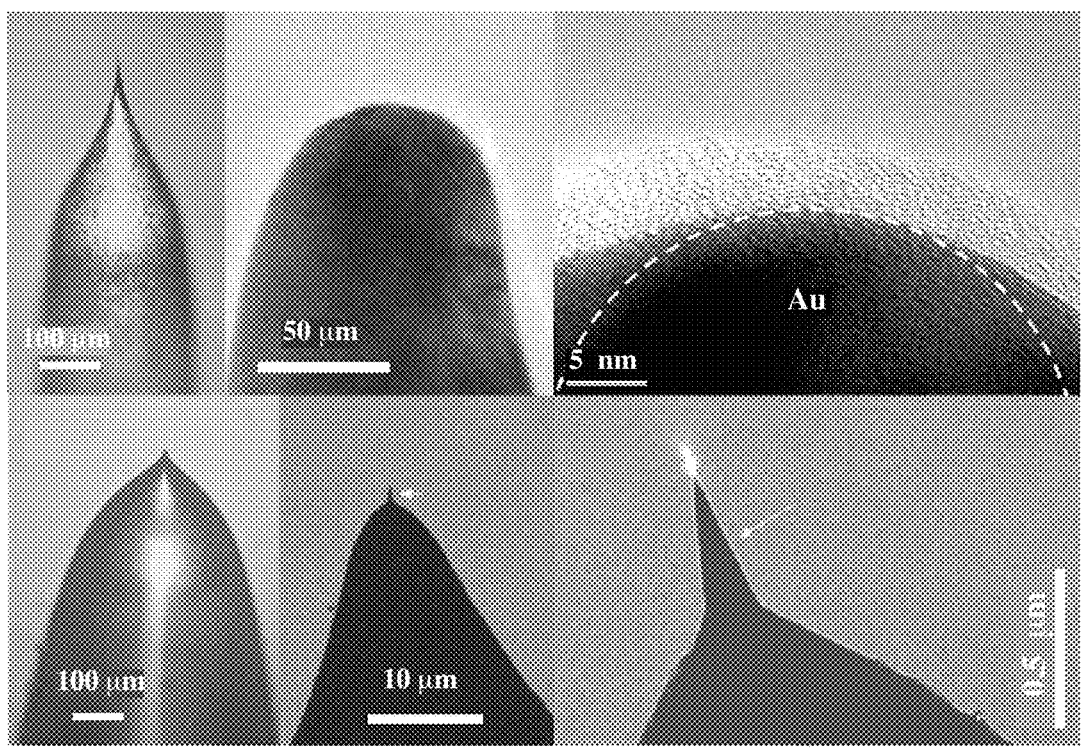
FIGS. 34A-34F shows optical and transmission electron microscope (TEM) images from exemplary electrodes.

The electrode was characterized by optical microscope and Transmission electron microscope (TEM) image. FIGS. 34*a-c* show a bare electrode and FIGS. 34*d-f* show a polyethylene coated tips. FIG. 34*a* shows an optical microscope image of a typical "good" tip. This tip was further characterized by transmission electron microscopy (TEM) as shown in FIGS. 34*b-c*. The tip radius in this case is about 16 nm (FIG. 34*c*). The carbon layer (the white layer covering the gold tip) was deposited during TEM imaging. The dashed arc has a radius of 16 nm. The measured radii typically spanned the range from 5 to 20 nm. The tip surface is normally smooth, but bumps (1-2 nm in height) are observed sometimes. It is, at first sight, surprising that such "blunt" probes could yield single molecule resolution, but the adsorption of molecules onto the surface generates local high points capable of single molecule resolution (and even better as illustrated by the resolution of internal molecular structure with functionalized AFM probes).

An optical microscope image of a typical insulated tip is shown in FIG. 34*d*. This tip showed no leakage current (below the measurement limit-1 pA) and about 8 pA (peak to peak, i.e. 4 pA above the baseline) 120 Hz noise in experiments. The TEM images of the same tip are shown in FIGS. 34*d-f*. The arrows in FIGS. 34*e-f* indicate the exposed gold (high resolution imaging is not possible owing to charging of the coating).

Example 6: Characterization of the Tunnel Gap 6.1 Water and Buffer

A tunnel gap with electrodes as described in Example 5 was characterized using doubly distilled water and 0.1 mM phosphate butter (PB-pH=7.4). Small signals were observed from the buffer alone with bare electrodes, but they were much rarer when both electrodes were functionalized and the tunnel gap conductance set to 20 pS or less. See FIG. 55. The tunnel decay was much more rapid (decay constant, $\beta=14.2\pm3.2$ nm$^{-1}$) with both electrodes functionalized than is the case in water alone ($\beta\sim6.1\pm0.7$ nm$^{-1-11}$). See Example 6.2 below. It is estimated the tunnel gap at i=10 pA and V=+0.5V is a little over the length of two benzamide molecules (i.e. a little greater than 2 nm).

6.2 Background Water Signals

Figure 35:
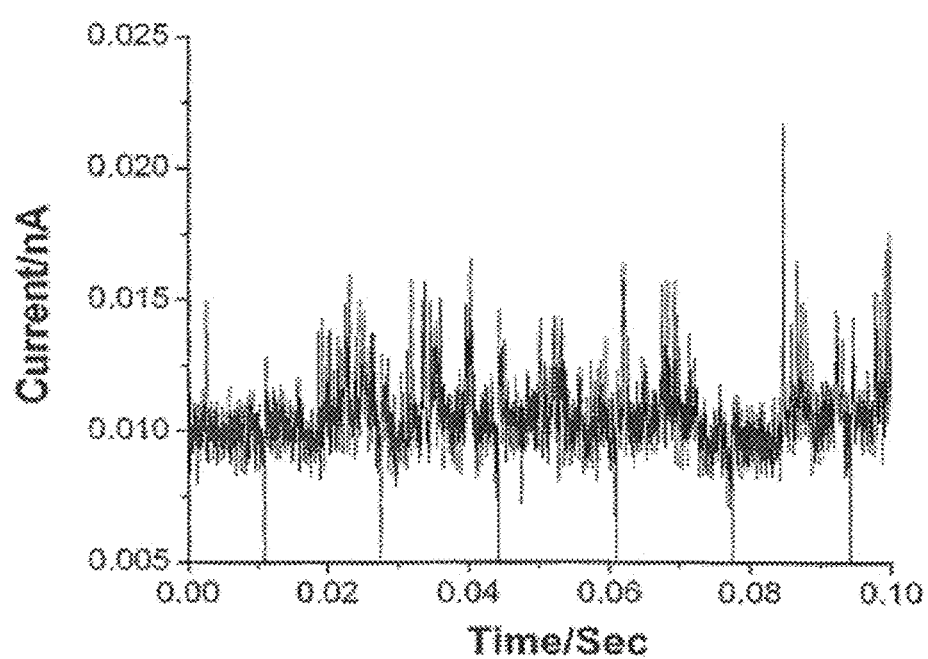
FIG. 35 illustrate telegraph noise in water with a bare electrode probe and a functionalized electrode surface. Similar signals were seen when both the probe and surface were bare and also in PB when either surface and/or probe was bare.

With a gap size of 20 pS at 0.5 volts, control experiment with bare electrodes on a functionalized substrate in doubly distilled water give background telegraph noise signals of a small amplitude (around 6 pA at 0.5 volts bias—FIG. 35). However, with functionalized tips on functionalized substrate, such signals are generally not observed (occasional observations of signals may originate with incomplete coverage of 4-mercatobenzamide on the surface of either the tip or the substrate). These background signals can be excluded by a threshold value in the data analysis since they are smaller in magnitude and less frequent than the DNA signals.

6.3 Tunneling Decay Curves

Figures 36A, 36B, 36C:
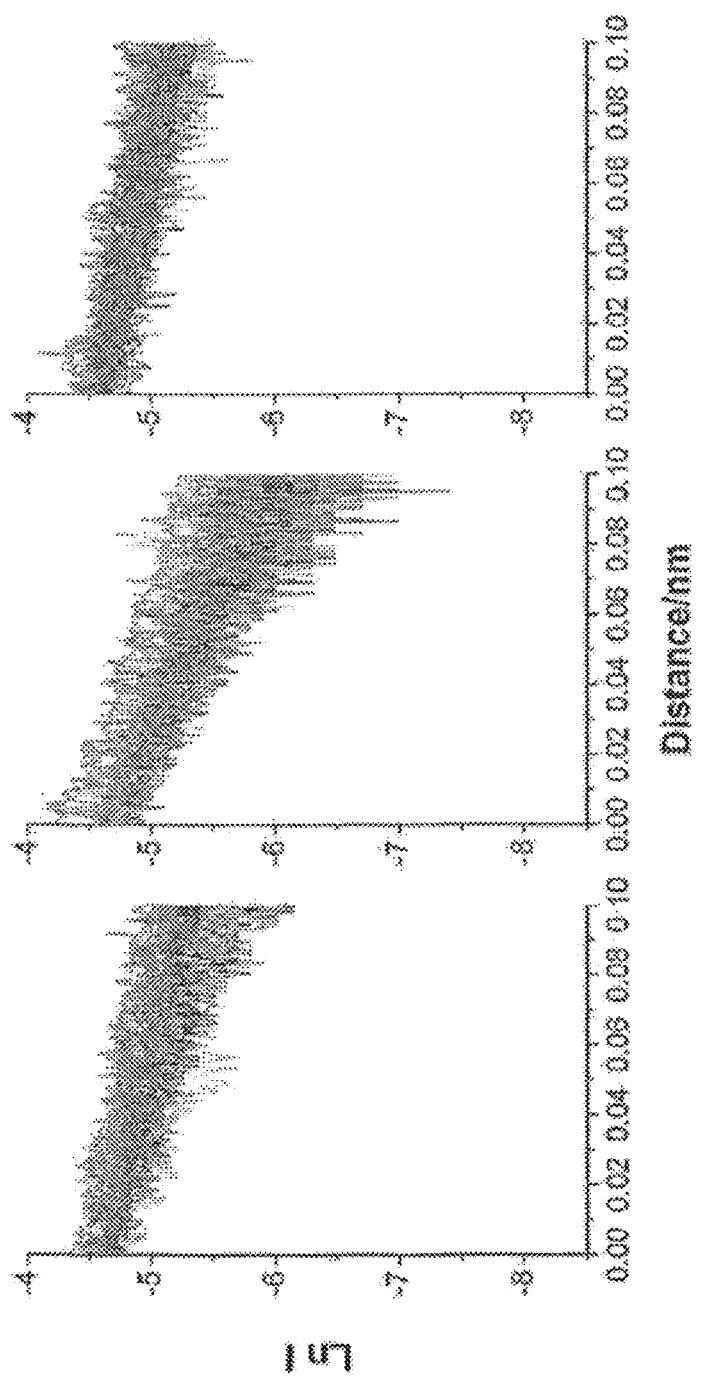
FIGS. 36A-36C show tunnel current decay curves in pure $H_2O$ (multiple curves are plotted in each case) for bare gold electrodes (FIG. 36A), functionalized electrodes (FIG. 36B), and one bare and one functionalize electrode (FIG. 36C).

Decay curves were measured in doubly-distilled water with a combination of functionalized and non-functionalized electrodes. The decay constant (13) was calculated from the slope of a linear fit of a plot of Ln (I) vs. distance (FIG. 36). FIG. 36 shows tunnel current decay curves in pure H20 (multiple curves are plotted in each case). FIG. 36*a* shows bare gold electrodes. FIG. 36*b* shows both electrodes functionalized. FIG. 36*c* shows one electrode bare and the other functionalized. A significant increase in 0 is detected for functionalized electrodes at large distances indicating a change of gap composition that we take to be a transition from the region where the benzamides interact to one where they do not. The distributions of measured vales of $\beta$ are shown in FIG. 37. FIG. 37 shows histograms of beta in pure water for (a) bare gold electrodes; (b) both electrodes functionalized with mercaptobenzamide; and (c) one electrode functionalized and the other bare. Gaussian fits (mean±SD) yield: (a) 6.11±0.68 nm$^{-1}$ (b) 14.16±3.20 nm$^{-1}$ (c) 6.84±0.92 nm$^{-1}$.

Example 7: Analyzing DNA Nucleotides in a Tunnel Gap

DNA nucleotides (10 μM in PB) were introduced into a tunnel gap created using electrodes as described in Example 5 in an aqueous electrolyte solution. These nucleotides yielded characteristic noise spikes as shown in FIGS. 56*c-f*. The signal count rate (defined in FIG. 57) varied considerably from 25 count/s (5-methyl-deoxycytidine 5'-monophophate, dmCMP) to less than 1 c/s (deoxycytidine 5'-monophophate, dCMP). No signals were recorded at all with thymidine 5'-monophophate (dTMP), the signal looking exactly like the control (FIG. 55). STM images suggest that this nucleotide binds to the surface (and presumably the probe) very strongly, blocking interactions in which a single molecule spans the junction.

The current occurs in bursts of spikes (longer signal runs are shown hereafter) and distributions of the spike heights were quite well fitted with two Gaussians distributions of the logarithm as shown in FIGS. 56g-j (the fitting parameters are described in Example 8 below). These histograms were generated by counting only pulses that exceeded 1.5× the SD of the local noise background—i.e., typically pulses above 6 pA (a full description of the analysis procedure is given by Chang et el.).

dCMP generates the highest signals and the lowest count rate while deoxyadenosine 5'-monophophate (dAMP) and dmCMP produce the smallest signals and the highest count rate. Little difference was found between cytidine and 5-methylcytidine in organic solvent as discussed Example 9 below. The three bases with narrower pulse height distributions (dAMP, dmCMP and GMP) often show bursts of "telegraph-noise" characteristic of sources that fluctuate between two levels (particularly marked for dAMP). Such a two-level distribution is a strong indication that the tunneling signals are generated by a single molecule trapped in the tunnel junction. The characteristics of the tunneling noise from the nucleotides are summarized in Table 4.

TABLE 4

Nucleotide tunneling noise characteristics.
Parameters are defined in FIG. 57.

| Nucleotide | dAMP | ctGMP | dCMP | dmCMP |
|---|---|---|---|---|
| Burst Duration ($T_B$, s) | 0.19 ± 0.05* | 0.13 ± 0.02* | 0.12 ± 0.02* | 0.06 ± 0.01* |
| Burst Frequency ($f_B$, Hz) | 732 ± 82§ | 574 ± 67§ | 306 ± 23§ | 1305 ± 100§ |
| Fraction of reads > 0.1 nA | 0.02 | 0.001 | 0.02 | 0.01 |
| $\tau_{on}$ (ms) | 0.38 ± 0.01* | 0.48 ± 0.02* | 0.42 ± 0.02* | 0.31 ± 0.09* |
| $\tau_{off}$ (ms) | 0.35 ± 0.01* | 0.56 ± 0.04* | 0.71 ± 0.06* | 0.41 ± 0.11* |
| $\tau_{on}/T_{off}$ | ~1 | 0.9 | 0.6 | 0.8 |
| ΔG (kT units) | 0 | 0.1 | 0.51 | 0.22 |

*Error in fit to exponential distribution.
§Standard error dAMP signals are well-separated from dCMP signals, and dmCMP signals are well separated from dCMP signals in spike amplitude and in the time distribution of their signals (Table 4 and discussed hereafter). For this reason, DNA oligomers composed of A, C and mC bases were further investigated below in Example 11.

Example 8: Gaussian Fits to Current Distributions

Peaks generated from the data of Example 7 were fitted with a Gaussian distribution in the logarithm of the tunnel current, a model that assumes a random distribution of tunnel geometries is sampled exponentially. For the present data in water, two peaks were required, implying two binding geometries:

$$N(i) = N_1 \exp\left(-\frac{[\ln(i) - \ln(i_{01})]^2}{[\ln(w_1)]^2}\right) + N_2 \exp\left(-\frac{[\ln(i) - \ln(i_{02})]^2}{[\ln(w_2)]^2}\right).$$

Equation S1

Fitting parameters are listed in TableS1.

TABLE S1

Intensity Distribution Fitting Parameters

| Sample | $i_{01}$ | $W_1$ | $I_{02}$ | $W_2$ | $N_2/N_1$ |
|---|---|---|---|---|---|
| damp | 0.014 | 0.712 | 0.022 | 0.491 | 0.45 |
| d(A)$_5$ | 0.013 | 0.727 | 0.022 | 0.531 | 0.43 |
| dCMP | 0.032 | 0.880 | 0.042 | 0.709 | 0.64 |
| d(C)$_5$ | 0.028 | 0.787 | 0.044 | 0.835 | 0.32 |
| d$^m$CMP | 0.017 | 0.771 | 0.024 | 0.627 | 0.62 |
| D($^m$C)$_5$ | 0.013 | 0.723 | 0.019 | 0.443 | 0.35 |
| dGMP | 0.016 | 0.852 | 0.022 | 0.596 | 2.01 |

Example 9: Current Distributions for Cytidine and 5Methylcytidine in Organic Solvent Data for mC measured in organic solvent with electrodes and 4-mercaptobenzamide readers according to Examples 4-5 are included here to show that the overlap between the signals from these two bases is much greater in organic solvent, which demonstrates that water molecules play a role in generating different signals from C and meC in the present work. FIG. 40 shows current distributions measured for cytidine (solid) and $^{5me}$cytidine (hashed) using benzoic acid readers in trichlorobenzene solvent.

Example 10: Analyzing Single Base within a Heteropolymer 10.1 Reading a Single Base within a Heteropolymer A d(CCACC) oligomer was analyzed by a two electrodes, a probe and a substrate both functionalized with 4-mercaptobenzamide as described above in Examples 4-5. Characteristic bursts of current were observed, and an example of which is shown in FIG. 54b (the spike labeled "*" is non-specific and rejected from the analysis). The background tunnel current is 10 pA, bias+0.5V. As shown below, the low frequency, large amplitude pulses indicate a C, while the high frequency, small amplitude pulses signal an A. FIG. 54c shows a sliding average of the spike amplitudes (0.25 s window, 0.125 s steps). Values below the straight line identify an A base unambiguously. FIG. 54d shows a sliding average over the pulse frequencies (as defined for each adjacent pair of spikes)—the low frequency regions at each end enhance the confidence with which those, regions can be assigned to a C base. C bases generate a negligible number of spikes below 0.015 nA (red line). The probability of an assignment to A or C is shown in FIG. 54e. Calculation of these probabilities is based on studies of nucleotides, homopolymers and heteropolymers as described herein. This example clearly shows that a single A base can be identified with high confidence when flanked by C bases in an intact DNA molecule.

10.2 Current Traces Showing Bursts for Nucleotides and Longtime Traces for d(CCACC)

FIG. 38 shows a sample of tunneling noise generated over a 10 s period as the probe drifts over a surface covered with d(CCACC). FIG. 39 shows typical "bursts" of signal from each of the nucleotides. In FIG. 38, a typical 10 s time trace for d(CCACC) is shown. Note the preponderance of A signals. The current spike distribution (inset) is almost completely dominated by "A" signals with the C component in the fit (see curve smaller box) being 7% or less. This shows that the probe spends more time bound to the minority of A bases. In FIG. 39, there are longer time traces for the nucleotides showing typical bursts of data. Each of these examples is surrounded by spike-free regions of current.

Example 11: Analyzing DNA Oligomers with 4-Mercaptobenzamide-Functionalized Electrodes FIGS. 58*a,c* and *e* show representative tunneling noise traces for d(A)5, d(C)5 and d(mC)5 with the corresponding current peak distributions shown in FIGS. 58*b, d* and *f* Comparing FIG. 58*b* (d(A)5) with FIG. 56*g* (dAMP), FIG. 58*d* (d(C)5) with FIG. 56*h* (dCMP) and FIG. 58*f* (d(mC)5) with FIG. 56*i* (dmCMP) demonstrates that surprisingly, most of the polymer binding events in the tunnel junction generate signals that resemble those generated by single nucleotides. This finding suggests that (1) that single bases are being read and (2) that steric constraints owing to the polymer backbone do not prevent base-binding events from dominating the signals.

There are some (small) differences between nucleotide and oligomer signals, these are: (1) Peak positions, widths and relative intensities are somewhat altered. (2) Almost all of the signals generated by nucleotides are less than 0.1 nA at 0.5V bias (Table 4). In contrast, 20% of the total signals generated by d(A)5 and d(mG)5 are larger than 0.1 nA at this bias (Table 5 (discussed below)—this is not obvious in FIGS. 56 G-J where distributions are plotted only up to 0.1 nA). These high current (>0.1 nA) features in d(A)S and d(C)S are continuously distributed so they do not represent parallel reads of more than one base at a time (where currents would be distributed in multiples of the single molecule values). Rather, they are new features associated with the presence of the polymeric structure in the tunnel gap. Such a non-specific, large amplitude spike is labeled by an asterisk in FIG. 54*b*.

Features at I>0.1 nA appear much less frequently in oligomers of mixed sequence, suggesting that they are associated with base-stacking in the homopolymers. FIG. 58*h* shows a current distribution for d(ACACA) where 95% of events are below 0.1 nA. FIG. 58*j* shows a current distribution for d(CmCCmCC) where 99% of events are below 0.1 nA. The solid red lines are the sums of the distributions measured for the homopolymers corresponding to the constituents with, scaling aside, only one fitting parameter. This parameter is the ratio, rfit, of the A/C (rfit=0.48) or mC/C (rfit=0.66) contributions. These values differ from the known composition ratios (0.6 for ACACA and 0.4 for CmCCmCC) but are surprising in as much as the spike rate for dCMP alone is very small, yet C appears to be quite well represented in the mixed sequence oligomer data. This suggests that Cs surrounded by As are read more frequently, possibly because the C-containing oligomer is better attached to the substrate than the isolated dCMP.

Importantly, mixed oligomers generate signals that are largely described as the sum of the individual base signals. (Some intermediate current reads, labeled "1" in FIGS. 58*h* and *j*, and a small number of additional high current features—labeled "2"—. show that sequence context plays a small role.)

In these experiments, the probe drifts randomly over the samples, so the sequence is not "read" deterministically. Nonetheless traces in which the signals alternate between "A-like" and "C-like" (FIG. 58*g*) and "mC-like" and "C-like" (FIG. 58*i*) may be readily found. The duration of these "bursts" (see FIG. 57 and Example 11) of signals is long (0.14±0.02 s in ACACA and 0.15±0.02 s in CmCC-mCC). Similar bursts are seen in the homopolymers (Table 5) and the nucleotides (Table 4).

TABLE 5

Oligomer tunneling noise characteristics. Parameters are defined in FIG. 57.

| Oligomer | D(A)$_5$ | D(C)$_5$ | D($^m$C)$_5$ |
|---|---|---|---|
| Burst Duration (T$_B$,s) | 0.14 ± 0.02* | 0.15 ± 0.03* | 0.41 ± 0.03* |
| Burst Frequency (f$_B$ Hz) | 738 ± 100$^§$ | 320 ± 85$^§$ | 662 ± 116$^§$ |
| Fraction of reads > 0.1 nA | 0.20 | 0.0 | 0.23 |
| τ$_{on}$ (ms) | 0.33 ± 0.01* | 0.34 ± 0.02* | 0.26 ± 0.01* |
| τ$_{off}$ (ms) | 0.52 ± 0.02* | 0.42 ± 0.01* | 0.47 ± 0.01* |
| τ$_{on}$/T$_{off}$ | 0.6 | 0.8 | 0.6 |
| ΔG (kT units) | 0.51 | 0.22 | 0.51 |

*Error in fit to exponential distribution.
$^§$Standard error

This leads to another unexpected finding, namely that the lifetime of the bound complex in the tunnel gap is very long (fraction of a second) compared to either the interval between noise spikes (ms) or the lifetime of the bound-state in solution (very short).

Example 12: Distributions of t$_{on}$ and t$_{off}$ of Example 11

Current spikes with durations of <0.1 ms are distorted by the slow (10 kHz) response of the current to voltage converter, while pulses of more than a few ms duration are affected by the feedback used to maintain the tunnel gap. The distributions of t$_{on}$ are shown for monomers in FIG. 41 and oligomers in FIG. 42. Distributions of t$_{off}$ are shown for monomers in FIG. 43 and oligomers in FIG. 44. The solid lines are fits to an exponential decay:

$$N(t) = \exp\left(\frac{-t}{\tau}\right)$$

giving the τ$_{on}$ and τ$_{off}$ values listed in Tables 4 and 5.

FIG. 41 shows the distribution of on times for dGMP, dCMP, dAMP, and dmCMP. Solid lines are exponential fits (from the top: 1$^{st}$ line is GMP, 2$^{nd}$ line is CMP, 3$^{rd}$ line is AMP, and 4$^{th}$ line is 5meC). FIG. 42 shows the distribution of on times for d(C)5, d(A)5 and d(mC)5. Solid lines are exponential fits (from the top: 1$^{st}$ line is CCCC, 2$^{nd}$ line is AAA, and 3$^{rd}$ line is 5mCCC). Distributions are less well separated than in the monomers. FIG. 43 shows the distribution of off times for dGMP, dCMP, dAMP and dmCMP. Solid lines are exponential fits (from the top: 1$^{st}$ line is CMP, 2$^{nd}$ line is GMP, 3$^{rd}$ line is 5meC, and 4$^{th}$ line is AMP). FIG. 44 shows the distribution of off times for d(C)s, d(A)s and d(mCMP)5. Solid lines are exponential fits (from the top: 1$^{st}$ line is AAAAA, 2$^{nd}$ line is 5mCCCC, and 3$^{rd}$ line is CCC). Again, distributions are less well separated than in the monomers.

Example 13: Testing the Long Lifetime of the Complex

Dynamic force spectroscopy was used as an independent test of the unexpectedly long lifetime of the 4-mercaptobenzamide-base-4-mercaptobenzamide complex confined to a nanoscale gap prepared according to Examples 4-5. In these measurements (FIG. 59a) one of the recognition molecules was bound to an AFM probe via a 34 nm long polyethyleneglycol (PEG) linker while the other formed a monolayer on an Au(111) substrate. dAMP was used as the target analyte to bridge the gap. In the absence of dAMP, adhesion between probe and substrate was extremely small, presumably because the hydrogen bonding sites on the benzamide recognition molecules were stably bound by water molecules. Adhesion features were observed in the presence of a small amount of dAMP, falling as the concentration of dAMP increased {resulting in binding of both probe and substrate by dAMP). Stretching of the PEG tether generated a characteristic signal that permitted multiple binding events (FIG. 59b (i)) to be separated from single molecule events (FIG. 59b (ii)) so that only single-molecule bond-breaking events were analyzed. Single molecule bond-breaking forces as a function of pulling speed are summarized in FIG. 59c (solid lines are maximum likelihood fits to a heterogeneous bond model) and the bond survival probability as a function of bond-breaking force is shown in FIG. 59d. The solid lines are fits to the same heterogeneous bond model. They yield an off-rate at zero force:

$$K_{off}^0 = 028 \ s^{-1}$$

Thus, the intrinsic (zeroforce) survival time of this complex is on the order of seconds, not milliseconds. The analysis also yields the distance to the transition state for dissociation, $\alpha=0.78$ nm (as well as its variance, $\sigma=0.19$ nm). Its thus concluded that each base resides in the tunnel junction for a significant fraction of a second, while generating tunneling signals at kHz rates. Thus the entire cluster of signals that occur in one burst (burst durations are listed in Tables 4 and 5) can be used to characterize a base.

Long-bound-state life-times accompanied by rapid fluctuations in electronic signatures have been reported previously in STM images and in the effect of single-molecule reactions on transport in carbon nanotubes. The origin of this noise is unclear, save that it appears to be very temperature sensitive, indicative of small energy barriers to the motion that causes the noise. The distribution of "on" and "off" times were analyzed (see FIG. 57). In a limited time range of times, determined by the amplifier response at one end, and the servo response time at the other, these distributions are exponential (as expected for a Poisson source) and the 1/e times ($\tau_{on}$ and $\tau_{off}$) are listed in Tables 4 and 5. They do not differ much, and calculating an energy difference, G, between the on and off states from:

$$\Delta G = kT_B \ln(\tau_{off}/\tau_{on})$$

yields the values listed in Tables 4 and 5 (in units of thermal energy, $k_B T$ at 300K). These values are all a fraction of $k_B T$. Thus the "switching" cannot represent thermal activation over a significant barrier (the normal source of two-level noise). One possible explanation is Brownian motion in a bound state sampled by an exponentially-sensitive matrix element.

The "on" and "off" times are so broadly distributed that they are not very useful for identifying base-signals. However, the frequency within a burst (fs Tables 4 and 5) is a much simpler parameter. FIGS. 49 and 50 show the current distributions and frequency distributions for the three homopolymers, normalized so that the area under each curve is unity. The frequency distribution for d(mC)5 is bimodal, with many reads in the "C" frequency range and a number at the very fast rate (ca. 1300 Hz) observed for mC MP alone (labeled f(mCMP) on the figure). This suggests that the binding modes of mC are altered significantly in a polymer context (consistent with the larger shift of the polymer signal compared to the nucleotide signal, FIG. 58f) so we chose to analyze oligomers containing A and C, in particular the d(CCACC) sequence previously analyzed.

Figure 52:
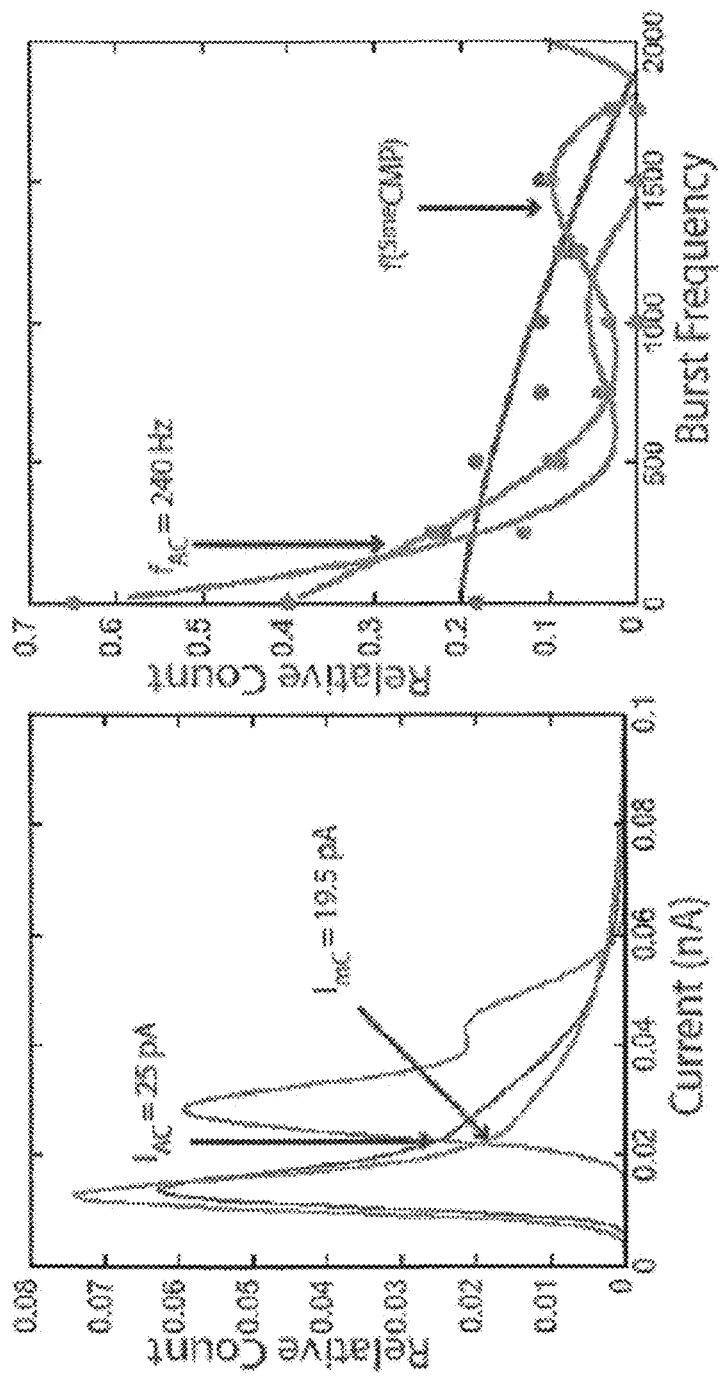

Given an average current in a burst, $\langle f \rangle$ and frequency, $\langle f \rangle$ the distributions shown in FIGS. 52a-b, $$I_{A,C}(\langle i \rangle)(\text{FIG. 52}a) \text{ and } F_{A,C}(\langle f \rangle)(\text{FIG. 52}b)$$

determine independent probabilities that a base is an A or a C:

$$P_{A,C}^i = \frac{I_{A,C}(\langle i \rangle)}{I_A(\langle i \rangle) + I_C(\langle i \rangle)} \text{ and } P_{A,C}^f = \frac{F_{A,C}(\langle f \rangle)}{F_A(\langle f \rangle) + F_C(\langle f \rangle)}$$

The current distribution from d(CCACC) (inset in FIG. 38) is almost completely dominated by A spikes (the component of the C distribution in this fit is 7% or less). This is a surprising result, that more C's in the sequence give a smaller number of C spikes. But it is consistent with our hypothesis that the frequency of C reads is increased when the base is flanked by A's (c.f. the increase in C reads in d(ACACA compared to the dCMP vs. dAMP count rate). Armed with our analysis of the burst signals, quantitative assignments of mixed signals may be made (this was done "by eye" in FIGS. 58g and i). d(C)5 produces no signals below 0.015 nA, so bursts of current below this level (but above the noise) can be unambiguously assigned to A. For larger amplitude signals both the frequency and amplitude data were used. The result is the pair of curves shown in FIG. 54e. Using this approach to sequence DNA requires several further developments. Firstly, the polymer must be pulled through a tunnel junction at a controlled speed, particularly if homopolymer runs are to be read. Since DNA passes through unfunctionalized nanopores too rapidly to be read the long residence time of bases in a functionalized tunnel junction is an asset. At present, movement from one site to another is driven by uncontrolled mechanical drift that generates unknown forces on the reading complex. Our force spectroscopy data can be used to give a crude estimate of the "pulling" force that would be needed to achieve a given read rate (assuming the measured off-rate for dAMP to be representative for all bases). The Bell equation gives the off rate at a force F as:

$$K_{off} = K_{off}^0 \exp\left(\frac{F\alpha}{k_B T}\right)$$

with $K_{off}^0 = 0.28 \ s^{-1}$ and $\alpha = 0.78$ nm, 19 pN would result in passage of 10 bases per second. A rate of 10 bases $s^{-1}$ gives about 30 data spikes (on average) for a "C" read, enough to generate an assignment with a reasonable level of confidence. A force of 19 pN can be generated by a bias of just 80 m V across a nanopore 17 so read rates of 10 bases per second per tunnel junction seem feasible.

Example 14: High Current Tails in the Current Distributions

FIG. 45 shows that distribution of counts for spikes>0.1 nA for d(A)5 for 4-mercaptobenzamide-functionalized electrodes. These are about 20% of the total and are not observed in dNTPs or d(C5). FIG. 46 shows that distribution of counts for spikes>0.1 nA for d(mC)5. These are about 20% of the total and are not observed in dNTPs or d(C5).

Example 15: SPR Estimation of Interactions of Nucleoside Monophosphates with 4-Mercaptobenzamide on a Gold Substrate and Bound State Lifetime in Solution Surface Plasmon Resonance (SPR) sensorgrams were recorded on a B 1-2000 SPR system (Biosensing Instrument, Tempe, Ariz.) that is equipped with a two-channel flow cell consisting of a polyaryletheretherketone (PEEK) cell block and a polydimethylsiloxane (PDMS) gasket. The wavelength of the incident light is 635 nm. Before each experiment, the flow cell was cleaned with ethanol and doubly distilled water.

The SPR sensor chip was fabricated by sequentially coating a 2 nm-thick chromium film and a 47 nm-thick gold film on a BK7 glass cover slide (VWR#48366067) in a sputter coater (Quorum Emitech Corporation, model K675XD). The gold substrate was cleaned with deionized water, absolute ethanol, nitrogen blowing, and then hydrogen flame annealing before use. A monolayer of benzamide was formed by on line injecting an ethanolic solution of 1-mercaptobenzamide to the gold chip placed on the SPR instrument using the serial channel mode. With molecules bonding to the gold surface, the SPR signal increases and eventually reaches a steady response, indicating a maximal coverage of the monolayer. The interactions of four naturally occurring nucleoside-5'-monophosphates with the benzamide surface were measured using a single channel mode on the SPR instrument. The sample solution injected via an injection valve flowed through one channel, while a PBS buffer (pH 7.4, 10 mM phosphate and 150 mM NaCl) flowed through the other one. The measurements were carried out at a flow rate of 60 μL min$^{-1}$ with concentration of nucleoside monophosphates at 1 mM in the PBS buffer.

The data analysis was carried out in the software provide by the vendor. All data sets were fit to a simple 1:1 interaction model.

The data do not determine $K_{off}$ but the very large values for $K_D$ (several mM) imply a rapid off rate. For example, assuming a (small) value of $K_{on}$=10$^6$ M$^{-1}$ s$^{-1}$, a mM $K_D$ yields $K_{off}$=$K_D K_{on}$=103 or ms timescales for the bound state lifetime.

FIG. 47 shows SPR sensorgrams of nucleoside-5'-monophosphates (A, C, G, T, R) interacting with the benzamide surface (R: 2-Deoxyribose 5-phosphate sodium salt containing no DNA base). Red lines are fitted curves modeled to describe a 1:1 binding event. Table 6 shows the rate constants and dissociation constants derived from the 1:1 binding kinetic analysis.

TABLE 6

|   | ka | kd | KD (mM) | RSD |
|---|---|---|---|---|
| A | 43 (3) | 0.159 (2) | 3.7 (3) | 1.914 |
| C | 60 (4) | 0.181 (3) | 3.0 (3) | 1.845 |
| G | 32 (4) | 0.172 (2) | 5.3 (6) | 1.675 |
| T | 68.6 (6) | 0.195 (4) | 2.9 (3) | 2.829 |

Example 16: Frequency of Bond Breaking Reads in Force Spectroscopy

After testing for interactions in the presence of buffer alone (FIG. 48a-shows the only detected adhesion events out of 1 024 pulls), 1 μM dAMP was added to the liquid cell configured with 4-mercaptobenzamide-functionalized electrodes and then force curves were taken as a function of the number of rinses of substrate and tip with 0.1 mM PB.

The data show an initial increase as excess dAMP is removed, followed by a decrease with continued rinsing (FIG. 48b-e). Specifically, FIG. 48 shows (a) control curves taken in the absence of dAMP showed almost no adhesion events between the benzamide molecules, presumably because they were blocked by water. Addition of dAMP led to a number of adhesion events that increased as excess dAMP was rinsed out of the system (b,c) decreasing as the rinsing continued (d,e).

Example 17: Noise Model

The purpose of this example is to outline a possible origin of the signals that are used to identify bases. As shown in example 13, the intrinsic life time of the bound comple in the tunnel junction is long—on the order of seconds. So the base is generally bound for all the time that it is adjacent to a functionalized electrode or probe if the electrode or probe is translated such that even a few bases are read per second. What is the origin of the current spikes that repeat on ms timescales? The distributions of "on" and "off" times given in example 12 can be used to compute an energy difference between the "on" and "off" states. This is listed as Gin Table 5. It is a fraction of thermal energy at 300K (the units are kT at 300K). Thus the spikes cannot be a consequence of the molecule jumping between a set of distinct thermally stable states. Here, we investigate the possibility that continuous Brownian motion can appear "spiky" when sampled in an exponential way (i.e., by tunneling which is exponentially sensitive to distance). Note that this model underlies the choice of an exponential distribution of the logarithm of currents (equation S1 in example 8). Brownian motion was simulated with a 1-D random walker driven by Gaussian (i.e., thermal) noise. The displacement was exponentiated to simulate the effect of a tunnel current readout of position. The following MatLab program was used:

for $x$=2: 10000

$z$=randn(1);

$y(x)$=correlation*$y(x-1)$+0.1*$z$;

end $a$=exp(beta*$y$);

plot$yy(t,y,t,a)$

The variable "correlation" describes how much of the position on one step is retained in the next step. Plots are shown for various values of the parameter "correlation" in FIGS. 49-51. A value close to 1 was required to obtain noise spikes that resemble the observed noise. The Intensity distribution was well fitted with a Gaussian in the logarithm of current (c.f., equation S1) and the time intervals between spikes was exponentially distributed. FIGS. 49-51 show simulated displacement (upper reads) and current (lower reads) vs. timesteps for three values of correlation, C.

Example 18: Probability Calculations

FIG. 52 shows normalized distributions for signals obtained from homopolymers in a device with 4-mercaptobenzamide-functionalized electrodes. FIG. 52A fits to normalized current distributions (from left to right: 1st peak=mC, 2nd peak=A, 3rd peak=C). FIG. 52B shows normalized spike frequencies (fS—see FIG. 57) in a signal burst, measured and fitted with polynomials (line beginning at about 0.2=A, line beginning at about 0.65=C, line beginning at about 0.4=mC). The fits to the distributions are used to assign the probability that a particular noise burst originates from an A or a C (if the average currents and frequencies lie above or below the crossover points, labeled "$I_{AC}$" and "$f_{AC}$"). Current distributions for C and mC are separated (crossover="$I_{mC}$") but frequency distributions overlap.

Values of:

$$I_A(\langle i \rangle) \text{ and } I_C(\langle i \rangle)$$

are taken from FIG. 52a. Since there are essentially no current spikes for C below 0.015 nA, bursts with average intensities smaller than 0.015 nA can be assigned to A reads. For bursts with intensities>0.015 nA, we use the values of:

$$F_A(\langle f \rangle) \text{ and } F_C(\langle f \rangle)$$

taken from the normalized distributions FIG. 52b, calculating the probability of an A read from the following:

$$1 - P_C^i P_C^f$$

and the probability of a C read from the following:

$$1 - P_A^i P_A^f$$

Example 19: Synthesis of Imidazole-2-Carboxamide

A short co-functionalized alkyl is needed to attach imidazole-2-carboxamide to electrodes. Because a variety of 4(5)-alkylated imidazoles are reported in literature or are commercially available, a general method to synthesize imidazole-2-carboxamides by amidation on the imidazole ring was developed. As delineated in the below Scheme, 4(5)-(2-thioethyl)imidazole-2-carboxamide (5a) and 4(5)-(2-aminoethyl)imidazole-2-carboxamide (Sb) were synthesized by amidating 4(5)-(2-(benzylthio)ethyl)imidazole (1a) and N-[2-(4-Imidazolyl)ethyl]phthalimide (1b) respectively. The thiol and amine function as anchor groups for attaching the molecule to metal and/or carbon electrodes. In the same way, 4(5)-(tert-butyldimethylsilyloxymethyl)imidazole-2-carboxamide (5c) was synthesized from 4(5)-(tert-butyldimethylsilyloxymethyl)imidazole (1c), which was used for NMR studies in organic solvents (vide infra).

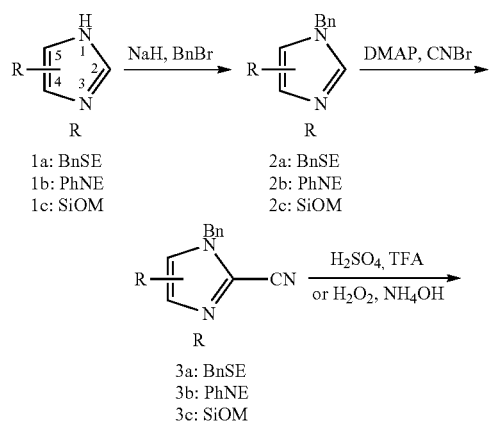

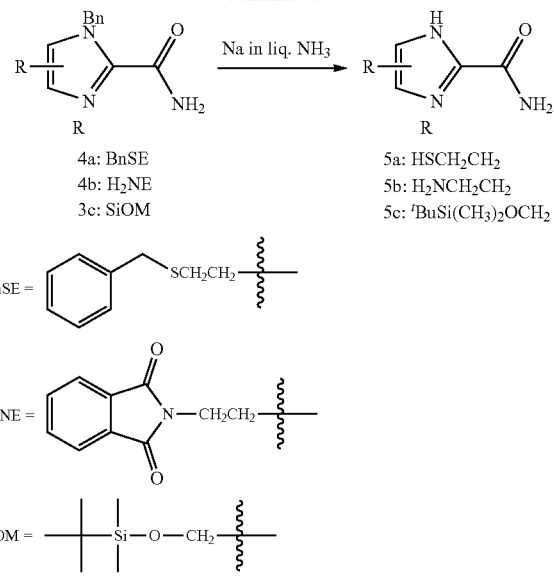

BnBr = Benzyl bromide; DMAP = 4-(Dimethylamino)pyridine; TFA = Trifluoroacetic acid Two routes to synthesizing these imidazole-2-carboxamides were explored. The 2-position of imidazole can be substituted with formate ester [15] or a cyano group, [16] both of which can readily be converted into amide. It was found that the cyano route gave us the best results. First, compound 1a, 1c and 1b were converted into the 1H nitrogen protected products (2a, 2b, 2c) in good yields by reacting with benzyl bromide. NMR confirms that each of them is a mixture of two isomers. The cyano group was introduced into the 2-position of the imidazole ring of 2a, 2b, and 2c by treating them with 1-cyano-4-(dimethylamino)pyridinium bromide (CAP). CPA was in situ generated by mixing equivalent amounts of cyanogens bromide and 4-(dimethylamino)pyridine in diemthyl formamide (DMF) at 0° C. A 2.5 fold of CAP resulted in the best yield. The cyano group of 3a, 3b, and 3c was converted into amide (4a, 4b, 4c) in fair yields by hydrolysis in sulfuric acid (20% by volume) and trifluoroacetic acid (18% by volume). We have tested the basic condition in the presence of hydrogen peroxide, but it failed to furnish the desired products. Final products of 5a, 5b, and 5c were obtained by removing the protecting groups with sodium in liquid ammonia. It is worth noting that the tert-butyldimethylsilyloxymethyl group was stable under the deprotecting condition. The desired compound 5c was seperated in a good yield.

Example 20: Analyzing DNA with Imidazole-2-Carboxyamide-Functionalized Electrodes Electrodes were prepared and functionalized with Imidazole-2-carboxyamide. A fixed tunnel gap was configured and deoxy-nucleotides were analyzed with baseline tunneling conditions of 6 pA, 0.5V. The control group showed almost no signals. FIGS. 62A and B show current distributions for $^mC$, A, T, C, and G. As is apparent, the current signatures for each of the nucleotides are distinct, thus demonstrating the effectiveness of imidazole-2-carboxyamide as a reagent.

Example 21: Analyzing DNA Oligomers with Imidazole-2-Carboxyamide-Functionalized Electrodes The electrodes of Example 20 were used to analyze the several homo- and hetero-oligomers. One electrode was configured to translate over an electrode surface at a constant gap as illustrated in FIG. 63. The typical speed of translation was about 8.6 nm/s, which simulates DNA being pulled through, for example, a nanopore.

FIG. 64 shows exemplary current distributions for d(CCCCC) (FIG. 64A) and d(AAAAA) (FIG. 648). The results of sequential reads for homopolymers are summarized in FIGS. 65-68 (AAAAA-FIG. 65; CCCCC—FIG. 66; d($^m$C)s—FIG. 67; and d(CCCCC) (FIG. 68)), plotting the current (nA) by time (s). The reads display consistent signals for the homopolymers.

The results of sequential reads for heteropolymers are summarized in FIGS. 70-75 (ACACA-FIG. 70; CCACC—FIG. 71; C$^m$CC$^m$CC—FIG. 72; d(ACACA)—FIG. 73; d(C$^m$CC$^m$CC)—FIG. 74); and d(GTCGTCGTC)—FIG. 75), plotting the current (nA) by time (s). The reads display consistent signals for the heteropolymers.

Thus, the above tests verify that imidazole-2-carboxyamide is an effective reagent for analyzing oligomers.

Example 22: Synthesis of 4-Carbamonylphenyldithiocarbamate

To a solution of 4-aminobenzamide (2 m mol, 272 mg) in DMF (1 mL), NaH (60% in mineral oil, 1.2 eq, 9.6 mg) and cs$_2$ (1.5 eq., 181.3 uL) were successively added at 0° C. as shown below.

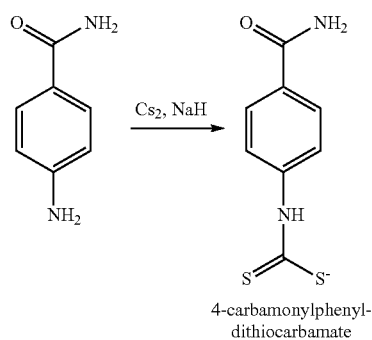 [SMILES: NC(=O)c1ccc(N)cc1 ; NC(=O)c1ccc(NC(=S)[S-])cc1]

4-carbamonylphenyl-dithiocarbamate

After 30 min at 0° C., the reaction mixture was warmed to room temperature and stirred for 84 h, and then warmed to 60° C. and stirred for 4 h. After cooling to room temperature, the reaction mixture was diluted with ether (20 mL), filtered, washed with ether to give a yellowish powder 183 mg (yield 39%).

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A device for analyzing a polymer, said device comprising
   (a) a first and second electrode that form a tunnel gap through which the polymer can pass; and
   (b) a first reagent attached to the first electrode and a second reagent attached to the second electrode wherein the first and second reagents are each capable of forming a transient bond to a unit of the polymer, wherein the first and second reagents are the same, and wherein a detectable signal is produced when the transient bond forms.

2. The device of claim 1, wherein the first and second reagents are selected from the group consisting of mercaptobenzoic acid, 4-mercaptobenzcarbamide, imidazole-2-carboxide, and 4-carbamonylphenyldithiocarbamate.

3. The device of claim 1, wherein the first and second reagents and a width of the tunnel gap are configured to produce a specific detectable signal for each monomer of the polymer when the first and second reagents form the transient bond to the unit of the polymer.

4. The device of claim 1, wherein the first and/or second electrode comprises gold, carbon, platinum, graphene, or titanium nitride.

5. The device of claim 1, wherein the detectable signal produced is caused by the binding of only one unit of the polymer in the tunnel gap.

6. The device of claim 1, wherein the tunnel gap has a width of about 1 nm to about 4 nm.

7. The device of claim 1, wherein the transient bond is a hydrogen bond.

8. The device of claim 1, wherein the first and second reagents comprise at least one hydrogen bond donor and at least one hydrogen bond acceptor in an aqueous solution.

9. The device of claim 1, wherein the polymer is DNA or RNA and the unit is a nucleotide.

10. The device of claim 1, wherein the unit is selected from the group consisting of A, C, T, G, and $^m$C.

11. The device of claim 1, further comprising
    c) a first fluid reservoir and a second fluid reservoir separated by at least one nanopore through which the polymer may flow.

12. The device of claim 11, further comprising a first driving electrode and a second driving electrode to apply an electrophoretic bias between the first fluid reservoir and the second fluid reservoir.

13. The device of claim 1, wherein the first and second electrodes comprise carbon nanotubes.

14. The device of claim 1, wherein the transient bond is pi-stacking between aromatic groups in the reader molecule and aromatic groups in the analyte.

* * * * *

UNITED STATES PATENT AND TRADEMARK OFFICE
CERTIFICATE OF CORRECTION

Page 1 of 1

PATENT NO. : 10,444,220 B2
APPLICATION NO. : 15/712552
DATED : October 15, 2019
INVENTOR(S) : Stuart Lindsay et al.

It is certified that error appears in the above-identified patent and that said Letters Patent is hereby corrected as shown below:

In the Specification

In Column 1, Line 18:
Delete the following paragraph:
"GOVERNMENT RIGHTS
This invention was made with government support under R01 HG006323 awarded by the National Institutes of Health. The government has certain rights in the invention."

Insert the following paragraph:
-- GOVERNMENT SUPPORT CLAUSE
This invention was made with government support under R21 HG004770 and HG004378 awarded by the National Institutes of Health. The government has certain rights in the invention. --

Signed and Sealed this
Twenty-first Day of January, 2020

Andrei Iancu
*Director of the United States Patent and Trademark Office*